US012618048B2

(12) United States Patent
Choulika et al.

(10) Patent No.: US 12,618,048 B2
(45) Date of Patent: May 5, 2026

(54) DUAL CAR-T CELLS

(71) Applicant: CELLECTIS S.A., Paris (FR)

(72) Inventors: André Choulika, Paris (FR); Laurent Poirot, Paris (FR); Beatriz Aranda Orgilles, Paris (FR); Philippe Duchateau, Paris (FR)

(73) Assignee: Cellectis S.A., Paris (FR)

( * ) Notice: Subject to any disclaimer, the term of this patent is extended or adjusted under 35 U.S.C. 154(b) by 553 days.

(21) Appl. No.: 18/016,972

(22) PCT Filed: Jul. 30, 2021

(86) PCT No.: PCT/EP2021/071400
§ 371 (c)(1),
(2) Date: Jan. 19, 2023

(87) PCT Pub. No.: WO2022/023529
PCT Pub. Date: Feb. 3, 2022

(65) Prior Publication Data
US 2023/0279350 A1 Sep. 7, 2023

(30) Foreign Application Priority Data

Jul. 31, 2020 (DK) .............................. PA202070509

(51) Int. Cl.
| | |
|---|---|
| *A61K 40/31* | (2025.01) |
| *A61K 40/11* | (2025.01) |
| *A61K 40/42* | (2025.01) |
| *A61P 35/00* | (2006.01) |
| *C07K 16/28* | (2006.01) |
| *C12N 5/0783* | (2010.01) |

(52) U.S. Cl.
CPC ............ *C12N 5/0636* (2013.01); *A61K 40/11* (2025.01); *A61K 40/31* (2025.01); *A61K 40/4212* (2025.01); *A61K 40/4221* (2025.01); *A61P 35/00* (2018.01); *C07K 16/2887* (2013.01); *C07K 16/2896* (2013.01); *A61K 2239/29* (2023.05); *A61K 2239/31* (2023.05); *A61K 2239/38* (2023.05); *A61K 2239/48* (2023.05); *C07K 2317/53* (2013.01); *C07K 2317/565* (2013.01); *C07K 2319/03* (2013.01)

(58) Field of Classification Search
CPC .............. C12N 5/0636; A61K 40/4212; A61K 40/4221; A61K 40/31
See application file for complete search history.

(56) References Cited

U.S. PATENT DOCUMENTS

| | | | |
|---|---|---|---|
| 4,683,195 A | 7/1987 | Mullis et al. | |
| 2017/0296623 A1* | 10/2017 | Juillerat et al. | ........ A61K 38/17 |

FOREIGN PATENT DOCUMENTS

| | | | | |
|---|---|---|---|---|
| WO | WO 2013/176915 | 11/2013 | | |
| WO | WO 2014/039523 | 3/2014 | | |
| WO | WO 2014/184744 | 11/2014 | | |
| WO | WO 2015/075195 | 5/2015 | | |
| WO | WO 2015/136001 | 9/2015 | | |
| WO | WO 2018/067992 | 4/2018 | | |
| WO | WO2018067992 A1 * | 4/2018 | ............ | C07K 16/28 |
| WO | WO 2018/178378 | 10/2018 | | |
| WO | WO2018178377 A1 * | 10/2018 | ............ | A61K 39/00 |

OTHER PUBLICATIONS

Aranda-Orgilles et al. (2023) "Preclinical evidence of an allogeneic dual CD20xCD22 CAR to target a broad spectrum of patients with B-cell Malignancies" Cancer Immunology Research, 11(7), 946-961. (Year: 2023).*

Huang, He (Feb. 21, 2020) "A Study of CD20/CD22 Targeted CAR T-cell Therapy for Relapsed or Refractory Lymphoid Malignancies" ClinicalTrials.gov, NCT04283006, version 1. (Year: 2020).*

Fousek et al. (Mar. 24, 2020) "CAR T-cells that target acute B-lineage leukemia irrespective of CD19 expression" Leukemia, 35:75-89. (Year: 2020).*

Chung et al., "Human Embryonic Stem Cell lines generated without embryo destruction," Cell Stem Cell, Feb. 2008, 2(2):113-117.

ClinicalTrials.gov [online], "A Study of CD20/CD22 Targeted CAR T-cell Therapy for Relapsed or Refractory Lymphoid Malignancies," NCT04283006, last updated Aug. 21, 2020, retrieved on Sep. 20, 2023, retrieved from URL<https://classic.clinicaltrials.gov/ct2/show/NCT04283006>, 9 pages.

Fousek et al., "Abstract A50: Trivalent CAR T cells mitigate CD 19-negative relapse and improve tumor control in primary pre-B cell acute lymphoblastic leukemia (B-ALL) ," Presented at Proceedings of the AACR Special Conference on Tumor Immunology and Immunotherapy, Oct. 1-4, 2017, Boston, MA, Cancer Immunol. Res., Sep. 2018, 6(9_Supplement):A50.

Fousek et al., "CAR T-cells that target acute B-lineage leukemia irrespective of CD19 expression," Leukemia, Jan. 2021, 35(1):75-89.

Fousek et al., "Targeting Primary Pre-B Cell Acute Lymphoblastic Leukemia and CD19-Negative Relapses Using Trivalent CAR T Cells," Blood, Dec. 2017, 130(Supplement 1):4614.

Gait, "Oligonucleotide Synthesis. A Practical Approach," FEBS Letters, Aug. 1985, 188(1):166-167.

GenBank Accession No. NM_001185099.1, "*Homo sapiens* CD22 molecule (CD22), transcript variant 2, mRNA," dated Dec. 10, 2018, 5 pages.

GenBank Accession No. NM_001185100.1, "*Homo sapiens* CD22 molecule (CD22), transcript variant 3, mRNA," dated Feb. 22, 2019, 6 pages.

(Continued)

*Primary Examiner* — James Joseph Graber

(74) *Attorney, Agent, or Firm* — Fish & Richardson P.C.

(57) ABSTRACT

The present invention concerns new engineered immune cells expressing two CARs directed against two different targets, polynucleotides for preparing said immune cells, pharmaceutical compositions comprising said immune cells, and the use of said immune cells in the treatment of cancers.

26 Claims, 8 Drawing Sheets

Specification includes a Sequence Listing.

(56) References Cited

OTHER PUBLICATIONS

GenBank Accession No. NM_001185101.1, "*Homo sapiens* CD22 molecule (CD22), transcript variant 4, mRNA," dated Jun. 8, 2019, 4 pages.

GenBank Accession No. NM_001278417.1, "*Homo sapiens* CD22 molecule (CD22), transcript variant 5, mRNA," dated Dec. 16, 2018, 4 pages.

GenBank Accession No. NM_001771.3, "*Homo sapiens* CD22 molecule (CD22), transcript variant 1, mRNA," dated Oct. 21, 2018, 6 pages.

GenBank Accession No. NM_021950.3, "*Homo sapiens* membrane spanning 4-domains A1 (MS4A1), transcript variant 3, mRNA," dated Jul. 6, 2019, 5 pages.

GenBank Accession No. NM_152866.2, "*Homo sapiens* membrane spanning 4-domains Al (MS4A1), transcript variant 1, mRNA," dated May 4, 2019, 5 pages.

GenPept Accession No. NP_001172028.1, "B-cell receptor CD22 isoform 2 precursor [*Homo sapiens*]," dated Jul. 7, 2019, 6 pages.

GenPept Accession No. NP_001172029.1, "B-cell receptor CD22 isoform 3 precursor [*Homo sapiens*]," dated Jul. 7, 2019, 7 pages.

GenPept Accession No. NP_001172030.1, "B-cell receptor CD22 isoform 4 precursor [*Homo sapiens*]," dated Jul. 6, 2019, 5 pages.

GenPept Accession No. NP_001265346.1, "B-cell receptor CD22 isoform 5 [*Homo sapiens*]," dated Jul. 7, 2019, 4 pages.

GenPept Accession No. NP_001762.2, "B-cell receptor CD22 isoform 1 precursor [*Homo sapiens*]," dated Jul. 6, 2019, 8 pages.

GenPept Accession No. NP_068769.2, "B-lymphocyte antigen CD20 [*Homo sapiens*]," dated Jul. 6, 2019, 4 pages.

GenPept Accession No. NP_690605.1, "B-lymphocyte antigen CD20 [*Homo sapiens*]," dated May 4, 2019, 4 pages.

Guedan et al., "Engineering and Design of Chimeric Antigen Receptors," Mol. Ther. Methods Clin. Dev., Dec. 2018, 12:145-156.

Holstein et al, "CAR T-Cell Therapy in Hematologic Malignancies: A Voyage in Progress," Clin. Pharmacol. Ther., Jan. 2020, 107(1):112-122.

International Search Report and Written Opinion in International Appln. No. PCT/EP2021/071400, mailed on Nov. 10, 2021, 17 pages.

Jena et al., "Redirecting T-cell specificity by introducing a tumor-specific chimeric antigen receptor," Blood, Aug. 2010, 116(7):1035-1044.

Liu et al., "CRISPR-Cas9-mediated multiplex gene editing in CAR-T cells," Cell Res., Jan. 2017, 27(1):154-157.

Loh et al., "Reprogramming of T cells from human peripheral blood," Cell Stem Cell, Jul. 2010, 7(1):15-19.

Okita et al., "Generation of Mouse Induced Pluripotent Stem Cells Without Viral Vectors," Science, Nov. 2008, 322(5903):949-953.

Poirot et al., "Multiplex Genome-Edited T-cell Manufacturing Platform for "Off-the-Shelf" Adoptive T-cell Immunotherapies," Cancer. Res., Sep. 2015, 75(18):3853-3864.

Qasim et al., "Molecular remission of infant B-ALL after infusion of universal TALEN gene-edited CAR T cells," Sci. Transl. Med., Jan. 2017, 9(374):eaaj2013, 8 pages.

Rossi et al., "Multivalent Anti-CD20/Anti-CD22 Bispecific Antibody Fusion Proteins Made by the DNL Method Show Potent Lymphoma Cytotoxicity," Blood, Nov. 2006, 108(11):2495.

Schwartz et al., "Guidelines on the use of therapeutic apheresis in clinical practice-evidence-based approach from the Writing Committee of the American Society for Apheresis: the Sixth Special Issue," J. Clin. Apher., Jul. 2013, 28(3):145-284.

Staerk et al, "Reprogramming of human peripheral blood cells to induced pluripotent stem cells," Cell Stem Cell, Jul. 2010, 7(1):20-24.

Tuscano et al., "The Bs20x22 anti-CD20-CD22 bispecific antibody has more lymphomacidal activity than do the parent antibodies alone," Cancer Immunol. Immunother., Feb. 2011, 60(6):771-780.

* cited by examiner

SEQUENCE LISTING

<160> NUMBER OF SEQ ID NOS: 52

<210> SEQ ID NO 1
<211> LENGTH: 21
<212> TYPE: PRT
<213> ORGANISM: artificial
<220> FEATURE:
<223> OTHER INFORMATION: CD8 alpha signal peptide

<400> SEQUENCE: 1

Met Ala Leu Pro Val Thr Ala Leu Leu Leu Pro Leu Ala Leu Leu Leu
1               5                   10                  15

His Ala Ala Arg Pro
            20

<210> SEQ ID NO 2
<211> LENGTH: 20
<212> TYPE: PRT
<213> ORGANISM: artificial
<220> FEATURE:
<223> OTHER INFORMATION: Alternative signal peptide

<400> SEQUENCE: 2

Met Glu Thr Asp Thr Leu Leu Leu Trp Val Leu Leu Leu Trp Val Pro
1               5                   10                  15

Gly Ser Thr Gly
            20

<210> SEQ ID NO 3
<211> LENGTH: 16
<212> TYPE: PRT
<213> ORGANISM: artificial
<220> FEATURE:
<223> OTHER INFORMATION: Fc gamma RIII alpha hinge

<400> SEQUENCE: 3

Gly Leu Ala Val Ser Thr Ile Ser Ser Phe Phe Pro Pro Gly Tyr Gln
1               5                   10                  15

<210> SEQ ID NO 4
<211> LENGTH: 45
<212> TYPE: PRT
<213> ORGANISM: artificial
<220> FEATURE:
<223> OTHER INFORMATION: CD8 alpha hinge

<400> SEQUENCE: 4

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
            35                  40                  45

<210> SEQ ID NO 5
<211> LENGTH: 231
<212> TYPE: PRT
<213> ORGANISM: artificial
<220> FEATURE:
<223> OTHER INFORMATION: IgG1 hinge

<400> SEQUENCE: 5

Glu Pro Lys Ser Pro Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ala Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

```
Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
        130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
            195                 200                 205

Cys Ser Val Met His Glu Ala Leu His Asn His Tyr Thr Gln Lys Ser
        210                 215                 220

Leu Ser Leu Ser Pro Gly Lys
225                 230

<210> SEQ ID NO 6
<211> LENGTH: 24
<212> TYPE: PRT
<213> ORGANISM: artificial
<220> FEATURE:
<223> OTHER INFORMATION: CD8 alpha transmembrane domain

<400> SEQUENCE: 6

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 7
<211> LENGTH: 27
<212> TYPE: PRT
<213> ORGANISM: artificial
<220> FEATURE:
<223> OTHER INFORMATION: 4-1BB transmembrane domain

<400> SEQUENCE: 7

Ile Ile Ser Phe Phe Leu Ala Leu Thr Ser Thr Ala Leu Leu Phe Leu
1               5                   10                  15

Leu Phe Phe Leu Thr Leu Arg Phe Ser Val Val
            20                  25

<210> SEQ ID NO 8
<211> LENGTH: 42
<212> TYPE: PRT
<213> ORGANISM: artificial
<220> FEATURE:
<223> OTHER INFORMATION: 4-1BB stimulatory domain

<400> SEQUENCE: 8

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
```

-continued

```
               20              25               30

Pro Glu Glu Glu Glu Gly Gly Cys Glu Leu
        35              40

<210> SEQ ID NO 9
<211> LENGTH: 112
<212> TYPE: PRT
<213> ORGANISM: artificial
<220> FEATURE:
<223> OTHER INFORMATION: CD3 zeta signalling domain

<400> SEQUENCE: 9

Arg Val Lys Phe Ser Arg Ser Ala Asp Ala Pro Ala Tyr Gln Gln Gly
1               5               10              15

Gln Asn Gln Leu Tyr Asn Glu Leu Asn Leu Gly Arg Arg Glu Glu Tyr
        20              25              30

Asp Val Leu Asp Lys Arg Arg Gly Arg Asp Pro Glu Met Gly Gly Lys
        35              40              45

Pro Arg Arg Lys Asn Pro Gln Glu Gly Leu Tyr Asn Glu Leu Gln Lys
        50              55              60

Asp Lys Met Ala Glu Ala Tyr Ser Glu Ile Gly Met Lys Gly Glu Arg
65              70              75              80

Arg Arg Gly Lys Gly His Asp Gly Leu Tyr Gln Gly Leu Ser Thr Ala
                85              90              95

Thr Lys Asp Thr Tyr Asp Ala Leu His Met Gln Ala Leu Pro Pro Arg
        100             105             110

<210> SEQ ID NO 10
<211> LENGTH: 15
<212> TYPE: PRT
<213> ORGANISM: artificial
<220> FEATURE:
<223> OTHER INFORMATION: Linker

<400> SEQUENCE: 10

Gly Gly Gly Gly Ser Gly Gly Gly Gly Ser Gly Gly Gly Gly Ser
1               5               10              15

<210> SEQ ID NO 11
<211> LENGTH: 124
<212> TYPE: PRT
<213> ORGANISM: artificial
<220> FEATURE:
<223> OTHER INFORMATION: CAR22 VH

<400> SEQUENCE: 11

Gln Val Gln Leu Gln Gln Ser Gly Pro Gly Leu Val Lys Pro Ser Gln
1               5               10              15

Thr Leu Ser Leu Thr Cys Ala Ile Ser Gly Asp Ser Val Ser Ser Asn
        20              25              30

Ser Ala Ala Trp Asn Trp Ile Arg Gln Ser Pro Ser Arg Gly Leu Glu
        35              40              45

Trp Leu Gly Arg Thr Tyr Tyr Arg Ser Lys Trp Tyr Asn Asp Tyr Ala
        50              55              60

Val Ser Val Lys Ser Arg Ile Thr Ile Asn Pro Asp Thr Ser Lys Asn
65              70              75              80

Gln Phe Ser Leu Gln Leu Asn Ser Val Thr Pro Glu Asp Thr Ala Val
                85              90              95

Tyr Tyr Cys Ala Arg Glu Val Thr Gly Asp Leu Glu Asp Ala Phe Asp
        100             105             110
```

```
Ile Trp Gly Gln Gly Thr Met Val Thr Val Ser Ser
        115                 120

<210> SEQ ID NO 12
<211> LENGTH: 107
<212> TYPE: PRT
<213> ORGANISM: artificial
<220> FEATURE:
<223> OTHER INFORMATION: CAR22 VL

<400> SEQUENCE: 12

Asp Ile Gln Met Thr Gln Ser Pro Ser Ser Leu Ser Ala Ser Val Gly
1                 5                 10                  15

Asp Arg Val Thr Ile Thr Cys Arg Ala Ser Gln Thr Ile Trp Ser Tyr
            20                  25                  30

Leu Asn Trp Tyr Gln Gln Arg Pro Gly Lys Ala Pro Asn Leu Leu Ile
            35                  40                  45

Tyr Ala Ala Ser Ser Leu Gln Ser Gly Val Pro Ser Arg Phe Ser Gly
        50                  55                  60

Arg Gly Ser Gly Thr Asp Phe Thr Leu Thr Ile Ser Ser Leu Gln Ala
65                  70                  75                  80

Glu Asp Phe Ala Thr Tyr Tyr Cys Gln Gln Ser Tyr Ser Ile Pro Gln
                85                  90                  95

Thr Phe Gly Gln Gly Thr Lys Leu Glu Ile Lys
            100                 105

<210> SEQ ID NO 13
<211> LENGTH: 246
<212> TYPE: PRT
<213> ORGANISM: artificial
<220> FEATURE:
<223> OTHER INFORMATION: CAR22 scFv

<400> SEQUENCE: 13

Gln Val Gln Leu Gln Gln Ser Gly Pro Gly Leu Val Lys Pro Ser Gln
1                 5                 10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
        50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Val Thr Gly Asp Leu Glu Asp Ala Phe Asp
            100                 105                 110

Ile Trp Gly Gln Gly Thr Met Val Thr Val Ser Ser Gly Gly Gly Gly
            115                 120                 125

Ser Gly Gly Gly Gly Ser Gly Gly Gly Gly Ser Asp Ile Gln Met Thr
        130                 135                 140

Gln Ser Pro Ser Ser Leu Ser Ala Ser Val Gly Asp Arg Val Thr Ile
145                 150                 155                 160

Thr Cys Arg Ala Ser Gln Thr Ile Trp Ser Tyr Leu Asn Trp Tyr Gln
                165                 170                 175

Gln Arg Pro Gly Lys Ala Pro Asn Leu Leu Ile Tyr Ala Ala Ser Ser
```

-continued

```
                 180                 185                 190

Leu Gln Ser Gly Val Pro Ser Arg Phe Ser Gly Arg Gly Ser Gly Thr
            195                 200                 205

Asp Phe Thr Leu Thr Ile Ser Ser Leu Gln Ala Glu Asp Phe Ala Thr
        210                 215                 220

Tyr Tyr Cys Gln Gln Ser Tyr Ser Ile Pro Gln Thr Phe Gly Gln Gly
225                 230                 235                 240

Thr Lys Leu Glu Ile Lys
                245

<210> SEQ ID NO 14
<211> LENGTH: 490
<212> TYPE: PRT
<213> ORGANISM: artificial
<220> FEATURE:
<223> OTHER INFORMATION: CAR22 full

<400> SEQUENCE: 14

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Pro Gly Leu
            20                  25                  30

Val Lys Pro Ser Gln Thr Leu Ser Leu Thr Cys Ala Ile Ser Gly Asp
        35                  40                  45

Ser Val Ser Ser Asn Ser Ala Ala Trp Asn Trp Ile Arg Gln Ser Pro
        50                  55                  60

Ser Arg Gly Leu Glu Trp Leu Gly Arg Thr Tyr Tyr Arg Ser Lys Trp
65                  70                  75                  80

Tyr Asn Asp Tyr Ala Val Ser Val Lys Ser Arg Ile Thr Ile Asn Pro
                85                  90                  95

Asp Thr Ser Lys Asn Gln Phe Ser Leu Gln Leu Asn Ser Val Thr Pro
            100                 105                 110

Glu Asp Thr Ala Val Tyr Tyr Cys Ala Arg Glu Val Thr Gly Asp Leu
            115                 120                 125

Glu Asp Ala Phe Asp Ile Trp Gly Gln Gly Thr Met Val Thr Val Ser
        130                 135                 140

Ser Gly Gly Gly Gly Ser Gly Gly Gly Gly Ser Gly Gly Gly Gly Ser
145                 150                 155                 160

Asp Ile Gln Met Thr Gln Ser Pro Ser Ser Leu Ser Ala Ser Val Gly
                165                 170                 175

Asp Arg Val Thr Ile Thr Cys Arg Ala Ser Gln Thr Ile Trp Ser Tyr
            180                 185                 190

Leu Asn Trp Tyr Gln Gln Arg Pro Gly Lys Ala Pro Asn Leu Leu Ile
            195                 200                 205

Tyr Ala Ala Ser Ser Leu Gln Ser Gly Val Pro Ser Arg Phe Ser Gly
        210                 215                 220

Arg Gly Ser Gly Thr Asp Phe Thr Leu Thr Ile Ser Ser Leu Gln Ala
225                 230                 235                 240

Glu Asp Phe Ala Thr Tyr Tyr Cys Gln Gln Ser Tyr Ser Ile Pro Gln
                245                 250                 255

Thr Phe Gly Gln Gly Thr Lys Leu Glu Ile Lys Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
```

-continued

```
        290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
                340                 345                 350

Arg Pro Val Gln Thr Thr Gln Glu Glu Asp Gly Cys Ser Cys Arg Phe
            355                 360                 365

Pro Glu Glu Glu Glu Gly Gly Cys Glu Leu Arg Val Lys Phe Ser Arg
    370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
                420                 425                 430

Gln Glu Gly Leu Tyr Asn Glu Leu Gln Lys Asp Lys Met Ala Glu Ala
            435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490
```

```
<210> SEQ ID NO 15
<211> LENGTH: 122
<212> TYPE: PRT
<213> ORGANISM: artificial
<220> FEATURE:
<223> OTHER INFORMATION: CAR20 VH

<400> SEQUENCE: 15

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
                20                  25                  30

Ala Met His Trp Val Arg Gln Ala Pro Gly Lys Gly Leu Glu Trp Val
            35                  40                  45

Ser Thr Ile Ser Trp Asn Ser Gly Ser Ile Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp
                100                 105                 110

Gly Gln Gly Thr Thr Val Thr Val Ser Ser
        115                 120
```

```
<210> SEQ ID NO 16
<211> LENGTH: 107
<212> TYPE: PRT
<213> ORGANISM: artificial
<220> FEATURE:
<223> OTHER INFORMATION: CAR20 VL
```

-continued

<400> SEQUENCE: 16

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
            100                 105

<210> SEQ ID NO 17
<211> LENGTH: 244
<212> TYPE: PRT
<213> ORGANISM: artificial
<220> FEATURE:
<223> OTHER INFORMATION: CAR20scFv

<400> SEQUENCE: 17

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
            20                  25                  30

Ala Met His Trp Val Arg Gln Ala Pro Gly Lys Gly Leu Glu Trp Val
        35                  40                  45

Ser Thr Ile Ser Trp Asn Ser Gly Ser Ile Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp
            100                 105                 110

Gly Gln Gly Thr Thr Val Thr Val Ser Ser Gly Gly Gly Gly Ser Gly
            115                 120                 125

Gly Gly Gly Ser Gly Gly Gly Ser Glu Ile Val Leu Thr Gln Ser
            130                 135                 140

Pro Ala Thr Leu Ser Leu Ser Pro Gly Glu Arg Ala Thr Leu Ser Cys
145                 150                 155                 160

Arg Ala Ser Gln Ser Val Ser Ser Tyr Leu Ala Trp Tyr Gln Gln Lys
                165                 170                 175

Pro Gly Gln Ala Pro Arg Leu Leu Ile Tyr Asp Ala Ser Asn Arg Ala
            180                 185                 190

Thr Gly Ile Pro Ala Arg Phe Ser Gly Ser Gly Ser Gly Thr Asp Phe
            195                 200                 205

Thr Leu Thr Ile Ser Ser Leu Glu Pro Glu Asp Phe Ala Val Tyr Tyr
    210                 215                 220

Cys Gln Gln Arg Ser Asn Trp Pro Ile Thr Phe Gly Gln Gly Thr Arg
225                 230                 235                 240

-continued

```
Leu Glu Ile Lys

<210> SEQ ID NO 18
<211> LENGTH: 488
<212> TYPE: PRT
<213> ORGANISM: artificial
<220> FEATURE:
<223> OTHER INFORMATION: CAR20 full

<400> SEQUENCE: 18

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Arg Ser Leu Arg Leu Ser Cys Ala Ala Ser Gly Phe
        35                  40                  45

Thr Phe Asn Asp Tyr Ala Met His Trp Val Arg Gln Ala Pro Gly Lys
    50                  55                  60

Gly Leu Glu Trp Val Ser Thr Ile Ser Trp Asn Ser Gly Ser Ile Gly
65                  70                  75                  80

Tyr Ala Asp Ser Val Lys Gly Arg Phe Thr Ile Ser Arg Asp Asn Ala
                85                  90                  95

Lys Lys Ser Leu Tyr Leu Gln Met Asn Ser Leu Arg Ala Glu Asp Thr
            100                 105                 110

Ala Leu Tyr Tyr Cys Ala Lys Asp Ile Gln Tyr Gly Asn Tyr Tyr Tyr
            115                 120                 125

Gly Met Asp Val Trp Gly Gln Gly Thr Thr Val Thr Val Ser Ser Gly
        130                 135                 140

Gly Gly Gly Ser Gly Gly Gly Gly Ser Gly Gly Gly Gly Ser Glu Ile
145                 150                 155                 160

Val Leu Thr Gln Ser Pro Ala Thr Leu Ser Leu Ser Pro Gly Glu Arg
                165                 170                 175

Ala Thr Leu Ser Cys Arg Ala Ser Gln Ser Val Ser Ser Tyr Leu Ala
            180                 185                 190

Trp Tyr Gln Gln Lys Pro Gly Gln Ala Pro Arg Leu Leu Ile Tyr Asp
            195                 200                 205

Ala Ser Asn Arg Ala Thr Gly Ile Pro Ala Arg Phe Ser Gly Ser Gly
        210                 215                 220

Ser Gly Thr Asp Phe Thr Leu Thr Ile Ser Ser Leu Glu Pro Glu Asp
225                 230                 235                 240

Phe Ala Val Tyr Tyr Cys Gln Gln Arg Ser Asn Trp Pro Ile Thr Phe
                245                 250                 255

Gly Gln Gly Thr Arg Leu Glu Ile Lys Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
        290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
            340                 345                 350

Val Gln Thr Thr Gln Glu Glu Asp Gly Cys Ser Cys Arg Phe Pro Glu
```

-continued

```
             355             360             365

Glu Glu Glu Gly Gly Cys Glu Leu Arg Val Lys Phe Ser Arg Ser Ala
        370             375             380

Asp Ala Pro Ala Tyr Gln Gln Gly Gln Asn Gln Leu Tyr Asn Glu Leu
385             390             395             400

Asn Leu Gly Arg Arg Glu Glu Tyr Asp Val Leu Asp Lys Arg Arg Gly
                405             410             415

Arg Asp Pro Glu Met Gly Gly Lys Pro Arg Arg Lys Asn Pro Gln Glu
            420             425             430

Gly Leu Tyr Asn Glu Leu Gln Lys Asp Lys Met Ala Glu Ala Tyr Ser
            435             440             445

Glu Ile Gly Met Lys Gly Glu Arg Arg Arg Gly Lys Gly His Asp Gly
        450             455             460

Leu Tyr Gln Gly Leu Ser Thr Ala Thr Lys Asp Thr Tyr Asp Ala Leu
465             470             475             480

His Met Gln Ala Leu Pro Pro Arg
                485
```

<210> SEQ ID NO 19
<211> LENGTH: 22
<212> TYPE: PRT
<213> ORGANISM: artificial
<220> FEATURE:
<223> OTHER INFORMATION: P2A peptide

<400> SEQUENCE: 19

```
Gly Ser Gly Ala Thr Asn Phe Ser Leu Leu Lys Gln Ala Gly Asp Val
1               5               10              15

Glu Glu Asn Pro Gly Pro
            20
```

<210> SEQ ID NO 20
<211> LENGTH: 317
<212> TYPE: PRT
<213> ORGANISM: artificial
<220> FEATURE:
<223> OTHER INFORMATION: CD20-6His

<400> SEQUENCE: 20

```
Met Thr Thr Pro Arg Asn Ser Val Asn Gly Thr Phe Pro Ala Glu Pro
1               5               10              15

Met Lys Gly Pro Ile Ala Met Gln Ser Gly Pro Lys Pro Leu Phe Arg
            20              25              30

Arg Met Ser Ser Leu Val Gly Pro Thr Gln Ser Phe Phe Met Arg Glu
            35              40              45

Ser Lys Thr Leu Gly Ala Val Gln Ile Met Asn Gly Leu Phe His Ile
        50              55              60

Ala Leu Gly Gly Leu Leu Met Ile Pro Ala Gly Ile Tyr Ala Pro Ile
65              70              75              80

Cys Val Thr Val Trp Tyr Pro Leu Trp Gly Gly Ile Met Tyr Ile Ile
                85              90              95

Ser Gly Ser Leu Leu Ala Ala Thr Glu Lys Asn Ser Arg Lys Cys Leu
            100             105             110

Val Lys Gly Lys Met Ile Met Asn Ser Leu Ser Leu Phe Ala Ala Ile
            115             120             125

Ser Gly Met Ile Leu Ser Ile Met Asp Ile Leu Asn Ile Lys Ile Ser
        130             135             140
```

```
His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
            195                 200                 205

Ala Gly Ile Val Glu Asn Glu Trp Lys Arg Thr Cys Ser Arg Pro Lys
        210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
            275                 280                 285

Ser Pro Ile Glu Asn Asp Ser Ser Pro Gly Gly Gly Ser Gly Gly Gly
        290                 295                 300

Ser His His His His His His His His His His His
305                 310                 315
```

```
<210> SEQ ID NO 21
<211> LENGTH: 916
<212> TYPE: PRT
<213> ORGANISM: artificial
<220> FEATURE:
<223> OTHER INFORMATION: CD22-Fc

<400> SEQUENCE: 21
```

```
Met Glu Trp Ser Trp Val Phe Leu Phe Phe Leu Ser Val Thr Thr Gly
1               5                   10                  15

Val His Ser Asp Ser Ser Lys Trp Val Phe Glu His Pro Glu Thr Leu
            20                  25                  30

Tyr Ala Trp Glu Gly Ala Cys Val Trp Ile Pro Cys Thr Tyr Arg Ala
        35                  40                  45

Leu Asp Gly Asp Leu Glu Ser Phe Ile Leu Phe His Asn Pro Glu Tyr
    50                  55                  60

Asn Lys Asn Thr Ser Lys Phe Asp Gly Thr Arg Leu Tyr Glu Ser Thr
65                  70                  75                  80

Lys Asp Gly Lys Val Pro Ser Glu Gln Lys Arg Val Gln Phe Leu Gly
                85                  90                  95

Asp Lys Asn Lys Asn Cys Thr Leu Ser Ile His Pro Val His Leu Asn
            100                 105                 110

Asp Ser Gly Gln Leu Gly Leu Arg Met Glu Ser Lys Thr Glu Lys Trp
        115                 120                 125

Met Glu Arg Ile His Leu Asn Val Ser Glu Arg Pro Phe Pro Pro His
        130                 135                 140

Ile Gln Leu Pro Pro Glu Ile Gln Glu Ser Gln Glu Val Thr Leu Thr
145                 150                 155                 160

Cys Leu Leu Asn Phe Ser Cys Tyr Gly Tyr Pro Ile Gln Leu Gln Trp
                165                 170                 175

Leu Leu Glu Gly Val Pro Met Arg Gln Ala Ala Val Thr Ser Thr Ser
            180                 185                 190
```

-continued

```
Leu Thr Ile Lys Ser Val Phe Thr Arg Ser Glu Leu Lys Phe Ser Pro
        195                 200                 205

Gln Trp Ser His His Gly Lys Ile Val Thr Cys Gln Leu Gln Asp Ala
    210                 215                 220

Asp Gly Lys Phe Leu Ser Asn Asp Thr Val Gln Leu Asn Val Lys His
225                 230                 235                 240

Thr Pro Lys Leu Glu Ile Lys Val Thr Pro Ser Asp Ala Ile Val Arg
                245                 250                 255

Glu Gly Asp Ser Val Thr Met Thr Cys Glu Val Ser Ser Ser Asn Pro
                260                 265                 270

Glu Tyr Thr Thr Val Ser Trp Leu Lys Asp Gly Thr Ser Leu Lys Lys
            275                 280                 285

Gln Asn Thr Phe Thr Leu Asn Leu Arg Glu Val Thr Lys Asp Gln Ser
    290                 295                 300

Gly Lys Tyr Cys Cys Gln Val Ser Asn Asp Val Gly Pro Gly Arg Ser
305                 310                 315                 320

Glu Glu Val Phe Leu Gln Val Gln Tyr Ala Pro Glu Pro Ser Thr Val
                325                 330                 335

Gln Ile Leu His Ser Pro Ala Val Glu Gly Ser Gln Val Glu Phe Leu
            340                 345                 350

Cys Met Ser Leu Ala Asn Pro Leu Pro Thr Asn Tyr Thr Trp Tyr His
            355                 360                 365

Asn Gly Lys Glu Met Gln Gly Arg Thr Glu Glu Lys Val His Ile Pro
    370                 375                 380

Lys Ile Leu Pro Trp His Ala Gly Thr Tyr Ser Cys Val Ala Glu Asn
385                 390                 395                 400

Ile Leu Gly Thr Gly Gln Arg Gly Pro Gly Ala Glu Leu Asp Val Gln
                405                 410                 415

Tyr Pro Pro Lys Lys Val Thr Thr Val Ile Gln Asn Pro Met Pro Ile
                420                 425                 430

Arg Glu Gly Asp Thr Val Thr Leu Ser Cys Asn Tyr Asn Ser Ser Asn
            435                 440                 445

Pro Ser Val Thr Arg Tyr Glu Trp Lys Pro His Gly Ala Trp Glu Glu
    450                 455                 460

Pro Ser Leu Gly Val Leu Lys Ile Gln Asn Val Gly Trp Asp Asn Thr
465                 470                 475                 480

Thr Ile Ala Cys Ala Ala Cys Asn Ser Trp Cys Ser Trp Ala Ser Pro
            485                 490                 495

Val Ala Leu Asn Val Gln Tyr Ala Pro Arg Asp Val Arg Val Arg Lys
            500                 505                 510

Ile Lys Pro Leu Ser Glu Ile His Ser Gly Asn Ser Val Ser Leu Gln
            515                 520                 525

Cys Asp Phe Ser Ser Ser His Pro Lys Glu Val Gln Phe Phe Trp Glu
    530                 535                 540

Lys Asn Gly Arg Leu Leu Gly Lys Glu Ser Gln Leu Asn Phe Asp Ser
545                 550                 555                 560

Ile Ser Pro Glu Asp Ala Gly Ser Tyr Ser Cys Trp Val Asn Asn Ser
                565                 570                 575

Ile Gly Gln Thr Ala Ser Lys Ala Trp Thr Leu Glu Val Leu Tyr Ala
            580                 585                 590

Pro Arg Arg Leu Arg Val Ser Met Ser Pro Gly Asp Gln Val Met Glu
            595                 600                 605

Gly Lys Ser Ala Thr Leu Thr Cys Glu Ser Asp Ala Asn Pro Pro Val
```

-continued

```
            610                 615                 620

Ser His Tyr Thr Trp Phe Asp Trp Asn Asn Gln Ser Leu Pro Tyr His
625                 630                 635                 640

Ser Gln Lys Leu Arg Leu Glu Pro Val Lys Val Gln His Ser Gly Ala
                645                 650                 655

Tyr Trp Cys Gln Gly Thr Asn Ser Val Gly Lys Gly Arg Ser Pro Leu
                660                 665                 670

Ser Thr Leu Thr Val Tyr Tyr Ser Pro Glu Thr Ile Gly Arg Arg Gly
                675                 680                 685

Gly Gly Gly Ala Gly Gly Gly Gly Cys Lys Pro Cys Ile Cys Thr Val
                690                 695                 700

Pro Glu Val Ser Ser Val Phe Ile Phe Pro Pro Lys Pro Lys Asp Val
705                 710                 715                 720

Leu Thr Ile Thr Leu Thr Pro Lys Val Thr Cys Val Val Val Asp Ile
                725                 730                 735

Ser Lys Asp Asp Pro Glu Val Gln Phe Ser Trp Phe Val Asp Asp Val
                740                 745                 750

Glu Val His Thr Ala Gln Thr Gln Pro Arg Glu Glu Gln Phe Asn Ser
                755                 760                 765

Thr Phe Arg Ser Val Ser Glu Leu Pro Ile Met His Gln Asp Trp Leu
                770                 775                 780

Asn Gly Lys Glu Phe Lys Cys Arg Val Asn Ser Ala Ala Phe Pro Ala
785                 790                 795                 800

Pro Ile Glu Lys Thr Ile Ser Lys Thr Lys Gly Arg Pro Lys Ala Pro
                805                 810                 815

Gln Val Tyr Thr Ile Pro Pro Pro Lys Glu Gln Met Ala Asp Lys Val
                820                 825                 830

Ser Leu Thr Cys Met Ile Thr Asp Phe Phe Pro Glu Asp Ile Thr Val
                835                 840                 845

Glu Trp Gln Trp Asn Gly Gln Pro Ala Glu Asn Tyr Lys Asn Thr Gln
                850                 855                 860

Pro Ile Met Asp Thr Asp Gly Ser Tyr Phe Val Tyr Ser Lys Leu Asn
865                 870                 875                 880

Val Gln Lys Ser Asn Trp Glu Ala Gly Asn Thr Phe Thr Cys Ser Val
                885                 890                 895

Leu His Glu Gly Leu His Asn His His Thr Glu Lys Ser Leu Ser His
                900                 905                 910

Ser Pro Gly Lys
        915

<210> SEQ ID NO 22
<211> LENGTH: 9
<212> TYPE: PRT
<213> ORGANISM: artificial
<220> FEATURE:
<223> OTHER INFORMATION: rituximab-specific epitope

<400> SEQUENCE: 22

Cys Pro Tyr Ser Asn Pro Ser Leu Cys
1               5

<210> SEQ ID NO 23
<211> LENGTH: 925
<212> TYPE: PRT
<213> ORGANISM: artificial
<220> FEATURE:
<223> OTHER INFORMATION: TRAC_T01-L
```

```
<400> SEQUENCE: 23

Met Gly Asp Pro Lys Lys Lys Arg Lys Val Ile Asp Ile Ala Asp Leu
1               5                  10                  15

Arg Thr Leu Gly Tyr Ser Gln Gln Gln Glu Lys Ile Lys Pro Lys
            20                  25                  30

Val Arg Ser Thr Val Ala Gln His His Glu Ala Leu Val Gly His Gly
        35                  40                  45

Phe Thr His Ala His Ile Val Ala Leu Ser Gln His Pro Ala Ala Leu
    50                  55                  60

Gly Thr Val Ala Val Lys Tyr Gln Asp Met Ile Ala Ala Leu Pro Glu
65                  70                  75                  80

Ala Thr His Glu Ala Ile Val Gly Val Gly Lys Gln Trp Ser Gly Ala
                85                  90                  95

Arg Ala Leu Glu Ala Leu Leu Thr Val Ala Gly Glu Leu Arg Gly Pro
            100                 105                 110

Pro Leu Gln Leu Asp Thr Gly Gln Leu Leu Lys Ile Ala Lys Arg Gly
            115                 120                 125

Gly Val Thr Ala Val Glu Ala Val His Ala Trp Arg Asn Ala Leu Thr
    130                 135                 140

Gly Ala Pro Leu Asn Leu Thr Pro Gln Gln Val Val Ala Ile Ala Ser
145                 150                 155                 160

Asn Gly Gly Gly Lys Gln Ala Leu Glu Thr Val Gln Arg Leu Leu Pro
                165                 170                 175

Val Leu Cys Gln Ala His Gly Leu Thr Pro Gln Gln Val Val Ala Ile
            180                 185                 190

Ala Ser Asn Asn Gly Gly Lys Gln Ala Leu Glu Thr Val Gln Arg Leu
    195                 200                 205

Leu Pro Val Leu Cys Gln Ala His Gly Leu Thr Pro Gln Gln Val Val
    210                 215                 220

Ala Ile Ala Ser Asn Gly Gly Gly Lys Gln Ala Leu Glu Thr Val Gln
225                 230                 235                 240

Arg Leu Leu Pro Val Leu Cys Gln Ala His Gly Leu Thr Pro Glu Gln
            245                 250                 255

Val Val Ala Ile Ala Ser His Asp Gly Gly Lys Gln Ala Leu Glu Thr
            260                 265                 270

Val Gln Arg Leu Leu Pro Val Leu Cys Gln Ala His Gly Leu Thr Pro
    275                 280                 285

Glu Gln Val Val Ala Ile Ala Ser His Asp Gly Gly Lys Gln Ala Leu
    290                 295                 300

Glu Thr Val Gln Arg Leu Leu Pro Val Leu Cys Gln Ala His Gly Leu
305                 310                 315                 320

Thr Pro Glu Gln Val Val Ala Ile Ala Ser His Asp Gly Gly Lys Gln
            325                 330                 335

Ala Leu Glu Thr Val Gln Arg Leu Leu Pro Val Leu Cys Gln Ala His
            340                 345                 350

Gly Leu Thr Pro Glu Gln Val Val Ala Ile Ala Ser Asn Ile Gly Gly
            355                 360                 365

Lys Gln Ala Leu Glu Thr Val Gln Ala Leu Leu Pro Val Leu Cys Gln
    370                 375                 380

Ala His Gly Leu Thr Pro Glu Gln Val Val Ala Ile Ala Ser His Asp
385                 390                 395                 400

Gly Gly Lys Gln Ala Leu Glu Thr Val Gln Arg Leu Leu Pro Val Leu
```

-continued

```
                   405              410              415

Cys Gln Ala His Gly Leu Thr Pro Glu Gln Val Val Ala Ile Ala Ser
            420              425              430

Asn Ile Gly Gly Lys Gln Ala Leu Glu Thr Val Gln Ala Leu Leu Pro
            435              440              445

Val Leu Cys Gln Ala His Gly Leu Thr Pro Gln Gln Val Val Ala Ile
        450              455              460

Ala Ser Asn Asn Gly Gly Lys Gln Ala Leu Glu Thr Val Gln Arg Leu
465              470              475              480

Leu Pro Val Leu Cys Gln Ala His Gly Leu Thr Pro Glu Gln Val Val
            485              490              495

Ala Ile Ala Ser Asn Ile Gly Gly Lys Gln Ala Leu Glu Thr Val Gln
            500              505              510

Ala Leu Leu Pro Val Leu Cys Gln Ala His Gly Leu Thr Pro Gln Gln
            515              520              525

Val Val Ala Ile Ala Ser Asn Gly Gly Gly Lys Gln Ala Leu Glu Thr
            530              535              540

Val Gln Arg Leu Leu Pro Val Leu Cys Gln Ala His Gly Leu Thr Pro
545              550              555              560

Glu Gln Val Val Ala Ile Ala Ser Asn Ile Gly Gly Lys Gln Ala Leu
                565              570              575

Glu Thr Val Gln Ala Leu Leu Pro Val Leu Cys Gln Ala His Gly Leu
            580              585              590

Thr Pro Gln Gln Val Val Ala Ile Ala Ser Asn Gly Gly Gly Lys Gln
            595              600              605

Ala Leu Glu Thr Val Gln Arg Leu Leu Pro Val Leu Cys Gln Ala His
        610              615              620

Gly Leu Thr Pro Glu Gln Val Val Ala Ile Ala Ser His Asp Gly Gly
625              630              635              640

Lys Gln Ala Leu Glu Thr Val Gln Arg Leu Leu Pro Val Leu Cys Gln
            645              650              655

Ala His Gly Leu Thr Pro Gln Gln Val Val Ala Ile Ala Ser Asn Gly
            660              665              670

Gly Gly Arg Pro Ala Leu Glu Ser Ile Val Ala Gln Leu Ser Arg Pro
            675              680              685

Asp Pro Ala Leu Ala Ala Leu Thr Asn Asp His Leu Val Ala Leu Ala
        690              695              700

Cys Leu Gly Gly Arg Pro Ala Leu Asp Ala Val Lys Lys Gly Leu Gly
705              710              715              720

Asp Pro Ile Ser Arg Ser Gln Leu Val Lys Ser Glu Leu Glu Glu Lys
                725              730              735

Lys Ser Glu Leu Arg His Lys Leu Lys Tyr Val Pro His Glu Tyr Ile
            740              745              750

Glu Leu Ile Glu Ile Ala Arg Asn Ser Thr Gln Asp Arg Ile Leu Glu
            755              760              765

Met Lys Val Met Glu Phe Phe Met Lys Val Tyr Gly Tyr Arg Gly Lys
            770              775              780

His Leu Gly Gly Ser Arg Lys Pro Asp Gly Ala Ile Tyr Thr Val Gly
785              790              795              800

Ser Pro Ile Asp Tyr Gly Val Ile Val Asp Thr Lys Ala Tyr Ser Gly
                805              810              815

Gly Tyr Asn Leu Pro Ile Gly Gln Ala Asp Glu Met Gln Arg Tyr Val
            820              825              830
```

```
Glu Glu Asn Gln Thr Arg Asn Lys His Ile Asn Pro Asn Glu Trp Trp
        835                 840                 845

Lys Val Tyr Pro Ser Ser Val Thr Glu Phe Lys Phe Leu Phe Val Ser
        850                 855                 860

Gly His Phe Lys Gly Asn Tyr Lys Ala Gln Leu Thr Arg Leu Asn His
865                 870                 875                 880

Ile Thr Asn Cys Asn Gly Ala Val Leu Ser Val Glu Glu Leu Leu Ile
            885                 890                 895

Gly Gly Glu Met Ile Lys Ala Gly Thr Leu Thr Leu Glu Glu Val Arg
            900                 905                 910

Arg Lys Phe Asn Asn Gly Glu Ile Asn Phe Ala Ala Asp
        915                 920                 925

<210> SEQ ID NO 24
<211> LENGTH: 925
<212> TYPE: PRT
<213> ORGANISM: artificial
<220> FEATURE:
<223> OTHER INFORMATION: TRAC_T01-R

<400> SEQUENCE: 24

Met Gly Asp Pro Lys Lys Lys Arg Lys Val Ile Asp Ile Ala Asp Leu
1               5                   10                  15

Arg Thr Leu Gly Tyr Ser Gln Gln Gln Glu Lys Ile Lys Pro Lys
        20                  25                  30

Val Arg Ser Thr Val Ala Gln His His Glu Ala Leu Val Gly His Gly
        35                  40                  45

Phe Thr His Ala His Ile Val Ala Leu Ser Gln His Pro Ala Ala Leu
        50                  55                  60

Gly Thr Val Ala Val Lys Tyr Gln Asp Met Ile Ala Ala Leu Pro Glu
65                  70                  75                  80

Ala Thr His Glu Ala Ile Val Gly Val Gly Lys Gln Trp Ser Gly Ala
            85                  90                  95

Arg Ala Leu Glu Ala Leu Leu Thr Val Ala Gly Glu Leu Arg Gly Pro
        100                 105                 110

Pro Leu Gln Leu Asp Thr Gly Gln Leu Leu Lys Ile Ala Lys Arg Gly
        115                 120                 125

Gly Val Thr Ala Val Glu Ala Val His Ala Trp Arg Asn Ala Leu Thr
        130                 135                 140

Gly Ala Pro Leu Asn Leu Thr Pro Glu Gln Val Val Ala Ile Ala Ser
145                 150                 155                 160

His Asp Gly Gly Lys Gln Ala Leu Glu Thr Val Gln Arg Leu Leu Pro
            165                 170                 175

Val Leu Cys Gln Ala His Gly Leu Thr Pro Gln Gln Val Val Ala Ile
        180                 185                 190

Ala Ser Asn Gly Gly Gly Lys Gln Ala Leu Glu Thr Val Gln Arg Leu
        195                 200                 205

Leu Pro Val Leu Cys Gln Ala His Gly Leu Thr Pro Glu Gln Val Val
        210                 215                 220

Ala Ile Ala Ser His Asp Gly Gly Lys Gln Ala Leu Glu Thr Val Gln
225                 230                 235                 240

Arg Leu Leu Pro Val Leu Cys Gln Ala His Gly Leu Thr Pro Glu Gln
            245                 250                 255

Val Val Ala Ile Ala Ser Asn Ile Gly Gly Lys Gln Ala Leu Glu Thr
            260                 265                 270
```

-continued

```
Val Gln Ala Leu Leu Pro Val Leu Cys Gln Ala His Gly Leu Thr Pro
    275                 280                 285

Gln Gln Val Val Ala Ile Ala Ser Asn Asn Gly Gly Lys Gln Ala Leu
    290                 295                 300

Glu Thr Val Gln Arg Leu Leu Pro Val Leu Cys Gln Ala His Gly Leu
305                 310                 315                 320

Thr Pro Glu Gln Val Val Ala Ile Ala Ser His Asp Gly Gly Lys Gln
                325                 330                 335

Ala Leu Glu Thr Val Gln Arg Leu Leu Pro Val Leu Cys Gln Ala His
                340                 345                 350

Gly Leu Thr Pro Gln Gln Val Val Ala Ile Ala Ser Asn Gly Gly Gly
                355                 360                 365

Lys Gln Ala Leu Glu Thr Val Gln Arg Leu Leu Pro Val Leu Cys Gln
    370                 375                 380

Ala His Gly Leu Thr Pro Gln Gln Val Val Ala Ile Ala Ser Asn Asn
385                 390                 395                 400

Gly Gly Lys Gln Ala Leu Glu Thr Val Gln Arg Leu Leu Pro Val Leu
                405                 410                 415

Cys Gln Ala His Gly Leu Thr Pro Gln Gln Val Val Ala Ile Ala Ser
                420                 425                 430

Asn Asn Gly Gly Lys Gln Ala Leu Glu Thr Val Gln Arg Leu Leu Pro
                435                 440                 445

Val Leu Cys Gln Ala His Gly Leu Thr Pro Gln Gln Val Val Ala Ile
    450                 455                 460

Ala Ser Asn Gly Gly Gly Lys Gln Ala Leu Glu Thr Val Gln Arg Leu
465                 470                 475                 480

Leu Pro Val Leu Cys Gln Ala His Gly Leu Thr Pro Glu Gln Val Val
                485                 490                 495

Ala Ile Ala Ser Asn Ile Gly Gly Lys Gln Ala Leu Glu Thr Val Gln
                500                 505                 510

Ala Leu Leu Pro Val Leu Cys Gln Ala His Gly Leu Thr Pro Glu Gln
                515                 520                 525

Val Val Ala Ile Ala Ser His Asp Gly Gly Lys Gln Ala Leu Glu Thr
    530                 535                 540

Val Gln Arg Leu Leu Pro Val Leu Cys Gln Ala His Gly Leu Thr Pro
545                 550                 555                 560

Glu Gln Val Val Ala Ile Ala Ser Asn Ile Gly Gly Lys Gln Ala Leu
                565                 570                 575

Glu Thr Val Gln Ala Leu Leu Pro Val Leu Cys Gln Ala His Gly Leu
                580                 585                 590

Thr Pro Glu Gln Val Val Ala Ile Ala Ser His Asp Gly Gly Lys Gln
                595                 600                 605

Ala Leu Glu Thr Val Gln Arg Leu Leu Pro Val Leu Cys Gln Ala His
    610                 615                 620

Gly Leu Thr Pro Gln Gln Val Val Ala Ile Ala Ser Asn Asn Gly Gly
625                 630                 635                 640

Lys Gln Ala Leu Glu Thr Val Gln Arg Leu Leu Pro Val Leu Cys Gln
                645                 650                 655

Ala His Gly Leu Thr Pro Gln Gln Val Val Ala Ile Ala Ser Asn Gly
                660                 665                 670

Gly Gly Arg Pro Ala Leu Glu Ser Ile Val Ala Gln Leu Ser Arg Pro
                675                 680                 685
```

-continued

```
Asp Pro Ala Leu Ala Ala Leu Thr Asn Asp His Leu Val Ala Leu Ala
    690                 695                 700

Cys Leu Gly Gly Arg Pro Ala Leu Asp Ala Val Lys Lys Gly Leu Gly
705                 710                 715                 720

Asp Pro Ile Ser Arg Ser Gln Leu Val Lys Ser Glu Leu Glu Glu Lys
                725                 730                 735

Lys Ser Glu Leu Arg His Lys Leu Lys Tyr Val Pro His Glu Tyr Ile
            740                 745                 750

Glu Leu Ile Glu Ile Ala Arg Asn Ser Thr Gln Asp Arg Ile Leu Glu
            755                 760                 765

Met Lys Val Met Glu Phe Phe Met Lys Val Tyr Gly Tyr Arg Gly Lys
    770                 775                 780

His Leu Gly Gly Ser Arg Lys Pro Asp Gly Ala Ile Tyr Thr Val Gly
785                 790                 795                 800

Ser Pro Ile Asp Tyr Gly Val Ile Val Asp Thr Lys Ala Tyr Ser Gly
                805                 810                 815

Gly Tyr Asn Leu Pro Ile Gly Gln Ala Asp Glu Met Gln Arg Tyr Val
            820                 825                 830

Glu Glu Asn Gln Thr Arg Asn Lys His Ile Asn Pro Asn Glu Trp Trp
        835                 840                 845

Lys Val Tyr Pro Ser Ser Val Thr Glu Phe Lys Phe Leu Phe Val Ser
    850                 855                 860

Gly His Phe Lys Gly Asn Tyr Lys Ala Gln Leu Thr Arg Leu Asn His
865                 870                 875                 880

Ile Thr Asn Cys Asn Gly Ala Val Leu Ser Val Glu Glu Leu Leu Ile
                885                 890                 895

Gly Gly Glu Met Ile Lys Ala Gly Thr Leu Thr Leu Glu Glu Val Arg
            900                 905                 910

Arg Lys Phe Asn Asn Gly Glu Ile Asn Phe Ala Ala Asp
            915                 920                 925
```

```
<210> SEQ ID NO 25
<211> LENGTH: 925
<212> TYPE: PRT
<213> ORGANISM: artificial
<220> FEATURE:
<223> OTHER INFORMATION: CD52_T01-L

<400> SEQUENCE: 25
```

```
Met Gly Asp Pro Lys Lys Lys Arg Lys Val Ile Asp Ile Ala Asp Leu
1               5                   10                  15

Arg Thr Leu Gly Tyr Ser Gln Gln Gln Glu Lys Ile Lys Pro Lys
            20                  25                  30

Val Arg Ser Thr Val Ala Gln His His Glu Ala Leu Val Gly His Gly
        35                  40                  45

Phe Thr His Ala His Ile Val Ala Leu Ser Gln His Pro Ala Ala Leu
    50                  55                  60

Gly Thr Val Ala Val Lys Tyr Gln Asp Met Ile Ala Ala Leu Pro Glu
65                  70                  75                  80

Ala Thr His Glu Ala Ile Val Gly Val Gly Lys Gln Trp Ser Gly Ala
                85                  90                  95

Arg Ala Leu Glu Ala Leu Leu Thr Val Ala Gly Glu Leu Arg Gly Pro
            100                 105                 110

Pro Leu Gln Leu Asp Thr Gly Gln Leu Leu Lys Ile Ala Lys Arg Gly
        115                 120                 125
```

-continued

```
Gly Val Thr Ala Val Glu Ala Val His Ala Trp Arg Asn Ala Leu Thr
    130                 135                 140

Gly Ala Pro Leu Asn Leu Thr Pro Gln Gln Val Val Ala Ile Ala Ser
145                 150                 155                 160

Asn Gly Gly Gly Lys Gln Ala Leu Glu Thr Val Gln Arg Leu Leu Pro
                165                 170                 175

Val Leu Cys Gln Ala His Gly Leu Thr Pro Glu Gln Val Val Ala Ile
                180                 185                 190

Ala Ser His Asp Gly Gly Lys Gln Ala Leu Glu Thr Val Gln Arg Leu
            195                 200                 205

Leu Pro Val Leu Cys Gln Ala His Gly Leu Thr Pro Glu Gln Val Val
    210                 215                 220

Ala Ile Ala Ser His Asp Gly Gly Lys Gln Ala Leu Glu Thr Val Gln
225                 230                 235                 240

Arg Leu Leu Pro Val Leu Cys Gln Ala His Gly Leu Thr Pro Gln Gln
                245                 250                 255

Val Val Ala Ile Ala Ser Asn Gly Gly Gly Lys Gln Ala Leu Glu Thr
                260                 265                 270

Val Gln Arg Leu Leu Pro Val Leu Cys Gln Ala His Gly Leu Thr Pro
        275                 280                 285

Glu Gln Val Val Ala Ile Ala Ser His Asp Gly Gly Lys Gln Ala Leu
    290                 295                 300

Glu Thr Val Gln Arg Leu Leu Pro Val Leu Cys Gln Ala His Gly Leu
305                 310                 315                 320

Thr Pro Glu Gln Val Val Ala Ile Ala Ser His Asp Gly Gly Lys Gln
                325                 330                 335

Ala Leu Glu Thr Val Gln Arg Leu Leu Pro Val Leu Cys Gln Ala His
                340                 345                 350

Gly Leu Thr Pro Gln Gln Val Val Ala Ile Ala Ser Asn Gly Gly Gly
            355                 360                 365

Lys Gln Ala Leu Glu Thr Val Gln Arg Leu Leu Pro Val Leu Cys Gln
    370                 375                 380

Ala His Gly Leu Thr Pro Glu Gln Val Val Ala Ile Ala Ser Asn Ile
385                 390                 395                 400

Gly Gly Lys Gln Ala Leu Glu Thr Val Gln Ala Leu Leu Pro Val Leu
                405                 410                 415

Cys Gln Ala His Gly Leu Thr Pro Glu Gln Val Val Ala Ile Ala Ser
                420                 425                 430

His Asp Gly Gly Lys Gln Ala Leu Glu Thr Val Gln Arg Leu Leu Pro
            435                 440                 445

Val Leu Cys Gln Ala His Gly Leu Thr Pro Gln Gln Val Val Ala Ile
    450                 455                 460

Ala Ser Asn Gly Gly Gly Lys Gln Ala Leu Glu Thr Val Gln Arg Leu
465                 470                 475                 480

Leu Pro Val Leu Cys Gln Ala His Gly Leu Thr Pro Glu Gln Val Val
                485                 490                 495

Ala Ile Ala Ser His Asp Gly Gly Lys Gln Ala Leu Glu Thr Val Gln
                500                 505                 510

Arg Leu Leu Pro Val Leu Cys Gln Ala His Gly Leu Thr Pro Glu Gln
            515                 520                 525

Val Val Ala Ile Ala Ser Asn Ile Gly Gly Lys Gln Ala Leu Glu Thr
    530                 535                 540

Val Gln Ala Leu Leu Pro Val Leu Cys Gln Ala His Gly Leu Thr Pro
```

```
545             550             555             560
Glu Gln Val Val Ala Ile Ala Ser His Asp Gly Gly Lys Gln Ala Leu
                565             570             575

Glu Thr Val Gln Arg Leu Leu Pro Val Leu Cys Gln Ala His Gly Leu
            580             585             590

Thr Pro Glu Gln Val Val Ala Ile Ala Ser His Asp Gly Gly Lys Gln
            595             600             605

Ala Leu Glu Thr Val Gln Arg Leu Leu Pro Val Leu Cys Gln Ala His
        610             615             620

Gly Leu Thr Pro Glu Gln Val Val Ala Ile Ala Ser Asn Ile Gly Gly
    625             630             635             640

Lys Gln Ala Leu Glu Thr Val Gln Ala Leu Leu Pro Val Leu Cys Gln
                645             650             655

Ala His Gly Leu Thr Pro Gln Gln Val Val Ala Ile Ala Ser Asn Gly
            660             665             670

Gly Gly Arg Pro Ala Leu Glu Ser Ile Val Ala Gln Leu Ser Arg Pro
            675             680             685

Asp Pro Ala Leu Ala Ala Leu Thr Asn Asp His Leu Val Ala Leu Ala
        690             695             700

Cys Leu Gly Gly Arg Pro Ala Leu Asp Ala Val Lys Lys Gly Leu Gly
705             710             715             720

Asp Pro Ile Ser Arg Ser Gln Leu Val Lys Ser Glu Leu Glu Glu Lys
            725             730             735

Lys Ser Glu Leu Arg His Lys Leu Lys Tyr Val Pro His Glu Tyr Ile
            740             745             750

Glu Leu Ile Glu Ile Ala Arg Asn Ser Thr Gln Asp Arg Ile Leu Glu
            755             760             765

Met Lys Val Met Glu Phe Phe Met Lys Val Tyr Gly Tyr Arg Gly Lys
            770             775             780

His Leu Gly Gly Ser Arg Lys Pro Asp Gly Ala Ile Tyr Thr Val Gly
785             790             795             800

Ser Pro Ile Asp Tyr Gly Val Ile Val Asp Thr Lys Ala Tyr Ser Gly
            805             810             815

Gly Tyr Asn Leu Pro Ile Gly Gln Ala Asp Glu Met Gln Arg Tyr Val
            820             825             830

Glu Glu Asn Gln Thr Arg Asn Lys His Ile Asn Pro Asn Glu Trp Trp
            835             840             845

Lys Val Tyr Pro Ser Ser Val Thr Glu Phe Lys Phe Leu Phe Val Ser
        850             855             860

Gly His Phe Lys Gly Asn Tyr Lys Ala Gln Leu Thr Arg Leu Asn His
865             870             875             880

Ile Thr Asn Cys Asn Gly Ala Val Leu Ser Val Glu Glu Leu Leu Ile
            885             890             895

Gly Gly Glu Met Ile Lys Ala Gly Thr Leu Thr Leu Glu Glu Val Arg
            900             905             910

Arg Lys Phe Asn Asn Gly Glu Ile Asn Phe Ala Ala Asp
            915             920             925
```

<210> SEQ ID NO 26
<211> LENGTH: 925
<212> TYPE: PRT
<213> ORGANISM: artificial
<220> FEATURE:
<223> OTHER INFORMATION: CD52_T01-R -continued

<400> SEQUENCE: 26

```
Met Gly Asp Pro Lys Lys Lys Arg Lys Val Ile Asp Ile Ala Asp Leu
1               5                   10                  15

Arg Thr Leu Gly Tyr Ser Gln Gln Gln Glu Lys Ile Lys Pro Lys
            20                  25                  30

Val Arg Ser Thr Val Ala Gln His His Glu Ala Leu Val Gly His Gly
        35                  40                  45

Phe Thr His Ala His Ile Val Ala Leu Ser Gln His Pro Ala Ala Leu
    50                  55                  60

Gly Thr Val Ala Val Lys Tyr Gln Asp Met Ile Ala Ala Leu Pro Glu
65                  70                  75                  80

Ala Thr His Glu Ala Ile Val Gly Val Gly Lys Gln Trp Ser Gly Ala
                85                  90                  95

Arg Ala Leu Glu Ala Leu Leu Thr Val Ala Gly Glu Leu Arg Gly Pro
            100                 105                 110

Pro Leu Gln Leu Asp Thr Gly Gln Leu Leu Lys Ile Ala Lys Arg Gly
            115                 120                 125

Gly Val Thr Ala Val Glu Ala Val His Ala Trp Arg Asn Ala Leu Thr
    130                 135                 140

Gly Ala Pro Leu Asn Leu Thr Pro Gln Gln Val Val Ala Ile Ala Ser
145                 150                 155                 160

Asn Gly Gly Gly Lys Gln Ala Leu Glu Thr Val Gln Arg Leu Leu Pro
                165                 170                 175

Val Leu Cys Gln Ala His Gly Leu Thr Pro Gln Gln Val Val Ala Ile
            180                 185                 190

Ala Ser Asn Asn Gly Gly Lys Gln Ala Leu Glu Thr Val Gln Arg Leu
            195                 200                 205

Leu Pro Val Leu Cys Gln Ala His Gly Leu Thr Pro Glu Gln Val Val
    210                 215                 220

Ala Ile Ala Ser His Asp Gly Gly Lys Gln Ala Leu Glu Thr Val Gln
225                 230                 235                 240

Arg Leu Leu Pro Val Leu Cys Gln Ala His Gly Leu Thr Pro Gln Gln
            245                 250                 255

Val Val Ala Ile Ala Ser Asn Gly Gly Gly Lys Gln Ala Leu Glu Thr
            260                 265                 270

Val Gln Arg Leu Leu Pro Val Leu Cys Gln Ala His Gly Leu Thr Pro
            275                 280                 285

Glu Gln Val Val Ala Ile Ala Ser His Asp Gly Gly Lys Gln Ala Leu
    290                 295                 300

Glu Thr Val Gln Arg Leu Leu Pro Val Leu Cys Gln Ala His Gly Leu
305                 310                 315                 320

Thr Pro Gln Gln Val Val Ala Ile Ala Ser Asn Gly Gly Gly Lys Gln
            325                 330                 335

Ala Leu Glu Thr Val Gln Arg Leu Leu Pro Val Leu Cys Gln Ala His
            340                 345                 350

Gly Leu Thr Pro Gln Gln Val Val Ala Ile Ala Ser Asn Gly Gly Gly
            355                 360                 365

Lys Gln Ala Leu Glu Thr Val Gln Arg Leu Leu Pro Val Leu Cys Gln
            370                 375                 380

Ala His Gly Leu Thr Pro Glu Gln Val Val Ala Ile Ala Ser Asn Ile
385                 390                 395                 400

Gly Gly Lys Gln Ala Leu Glu Thr Val Gln Ala Leu Leu Pro Val Leu
            405                 410                 415
```

```
Cys Gln Ala His Gly Leu Thr Pro Glu Gln Val Val Ala Ile Ala Ser
            420                 425                 430

His Asp Gly Gly Lys Gln Ala Leu Glu Thr Val Gln Arg Leu Leu Pro
            435                 440                 445

Val Leu Cys Gln Ala His Gly Leu Thr Pro Glu Gln Val Val Ala Ile
    450                 455                 460

Ala Ser His Asp Gly Gly Lys Gln Ala Leu Glu Thr Val Gln Arg Leu
465                 470                 475                 480

Leu Pro Val Leu Cys Gln Ala His Gly Leu Thr Pro Gln Gln Val Val
                485                 490                 495

Ala Ile Ala Ser Asn Gly Gly Lys Gln Ala Leu Glu Thr Val Gln
            500                 505                 510

Arg Leu Leu Pro Val Leu Cys Gln Ala His Gly Leu Thr Pro Gln Gln
            515                 520                 525

Val Val Ala Ile Ala Ser Asn Gly Gly Lys Gln Ala Leu Glu Thr
    530                 535                 540

Val Gln Arg Leu Leu Pro Val Leu Cys Gln Ala His Gly Leu Thr Pro
545                 550                 555                 560

Gln Gln Val Val Ala Ile Ala Ser Asn Gly Gly Lys Gln Ala Leu
            565                 570                 575

Glu Thr Val Gln Arg Leu Leu Pro Val Leu Cys Gln Ala His Gly Leu
            580                 585                 590

Thr Pro Glu Gln Val Val Ala Ile Ala Ser Asn Ile Gly Gly Lys Gln
            595                 600                 605

Ala Leu Glu Thr Val Gln Ala Leu Leu Pro Val Leu Cys Gln Ala His
    610                 615                 620

Gly Leu Thr Pro Glu Gln Val Val Ala Ile Ala Ser His Asp Gly Gly
625                 630                 635                 640

Lys Gln Ala Leu Glu Thr Val Gln Arg Leu Leu Pro Val Leu Cys Gln
            645                 650                 655

Ala His Gly Leu Thr Pro Gln Gln Val Val Ala Ile Ala Ser Asn Gly
            660                 665                 670

Gly Gly Arg Pro Ala Leu Glu Ser Ile Val Ala Gln Leu Ser Arg Pro
            675                 680                 685

Asp Pro Ala Leu Ala Ala Leu Thr Asn Asp His Leu Val Ala Leu Ala
    690                 695                 700

Cys Leu Gly Gly Arg Pro Ala Leu Asp Ala Val Lys Lys Gly Leu Gly
705                 710                 715                 720

Asp Pro Ile Ser Arg Ser Gln Leu Val Lys Ser Glu Leu Glu Glu Lys
            725                 730                 735

Lys Ser Glu Leu Arg His Lys Leu Lys Tyr Val Pro His Glu Tyr Ile
            740                 745                 750

Glu Leu Ile Glu Ile Ala Arg Asn Ser Thr Gln Asp Arg Ile Leu Glu
            755                 760                 765

Met Lys Val Met Glu Phe Phe Met Lys Val Tyr Gly Tyr Arg Gly Lys
            770                 775                 780

His Leu Gly Gly Ser Arg Lys Pro Asp Gly Ala Ile Tyr Thr Val Gly
785                 790                 795                 800

Ser Pro Ile Asp Tyr Gly Val Ile Val Asp Thr Lys Ala Tyr Ser Gly
            805                 810                 815

Gly Tyr Asn Leu Pro Ile Gly Gln Ala Asp Glu Met Gln Arg Tyr Val
            820                 825                 830
```

-continued

```
Glu Glu Asn Gln Thr Arg Asn Lys His Ile Asn Pro Asn Glu Trp Trp
        835                 840                 845

Lys Val Tyr Pro Ser Ser Val Thr Glu Phe Lys Phe Leu Phe Val Ser
        850                 855                 860

Gly His Phe Lys Gly Asn Tyr Lys Ala Gln Leu Thr Arg Leu Asn His
865                 870                 875                 880

Ile Thr Asn Cys Asn Gly Ala Val Leu Ser Val Glu Glu Leu Leu Ile
                885                 890                 895

Gly Gly Glu Met Ile Lys Ala Gly Thr Leu Thr Leu Glu Glu Val Arg
                900                 905                 910

Arg Lys Phe Asn Asn Gly Glu Ile Asn Phe Ala Ala Asp
        915                 920                 925

<210> SEQ ID NO 27
<211> LENGTH: 925
<212> TYPE: PRT
<213> ORGANISM: artificial
<220> FEATURE:
<223> OTHER INFORMATION: CD22_T01-L

<400> SEQUENCE: 27

Met Gly Asp Pro Lys Lys Lys Arg Lys Val Ile Asp Ile Ala Asp Leu
1                 5                   10                  15

Arg Thr Leu Gly Tyr Ser Gln Gln Gln Glu Lys Ile Lys Pro Lys
                20                  25                  30

Val Arg Ser Thr Val Ala Gln His His Glu Ala Leu Val Gly His Gly
        35                  40                  45

Phe Thr His Ala His Ile Val Ala Leu Ser Gln His Pro Ala Ala Leu
        50                  55                  60

Gly Thr Val Ala Val Lys Tyr Gln Asp Met Ile Ala Ala Leu Pro Glu
65                  70                  75                  80

Ala Thr His Glu Ala Ile Val Gly Val Gly Lys Gln Trp Ser Gly Ala
                85                  90                  95

Arg Ala Leu Glu Ala Leu Leu Thr Val Ala Gly Glu Leu Arg Gly Pro
                100                 105                 110

Pro Leu Gln Leu Asp Thr Gly Gln Leu Leu Lys Ile Ala Lys Arg Gly
        115                 120                 125

Gly Val Thr Ala Val Glu Ala Val His Ala Trp Arg Asn Ala Leu Thr
        130                 135                 140

Gly Ala Pro Leu Asn Leu Thr Pro Glu Gln Val Val Ala Ile Ala Ser
145                 150                 155                 160

His Asp Gly Gly Lys Gln Ala Leu Glu Thr Val Gln Arg Leu Leu Pro
                165                 170                 175

Val Leu Cys Gln Ala His Gly Leu Thr Pro Gln Gln Val Val Ala Ile
                180                 185                 190

Ala Ser Asn Gly Gly Gly Lys Gln Ala Leu Glu Thr Val Gln Arg Leu
        195                 200                 205

Leu Pro Val Leu Cys Gln Ala His Gly Leu Thr Pro Gln Gln Val Val
        210                 215                 220

Ala Ile Ala Ser Asn Asn Gly Gly Lys Gln Ala Leu Glu Thr Val Gln
225                 230                 235                 240

Arg Leu Leu Pro Val Leu Cys Gln Ala His Gly Leu Thr Pro Gln Gln
                245                 250                 255

Val Val Ala Ile Ala Ser Asn Asn Gly Gly Lys Gln Ala Leu Glu Thr
                260                 265                 270
```

-continued

```
Val Gln Arg Leu Leu Pro Val Leu Cys Gln Ala His Gly Leu Thr Pro
    275                 280                 285

Gln Gln Val Val Ala Ile Ala Ser Asn Gly Gly Gly Lys Gln Ala Leu
    290                 295                 300

Glu Thr Val Gln Arg Leu Leu Pro Val Leu Cys Gln Ala His Gly Leu
305                 310                 315                 320

Thr Pro Gln Gln Val Val Ala Ile Ala Ser Asn Gly Gly Gly Lys Gln
                325                 330                 335

Ala Leu Glu Thr Val Gln Arg Leu Leu Pro Val Leu Cys Gln Ala His
                340                 345                 350

Gly Leu Thr Pro Gln Gln Val Val Ala Ile Ala Ser Asn Gly Gly Gly
                355                 360                 365

Lys Gln Ala Leu Glu Thr Val Gln Arg Leu Leu Pro Val Leu Cys Gln
    370                 375                 380

Ala His Gly Leu Thr Pro Gln Gln Val Val Ala Ile Ala Ser Asn Gly
385                 390                 395                 400

Gly Gly Lys Gln Ala Leu Glu Thr Val Gln Arg Leu Leu Pro Val Leu
                405                 410                 415

Cys Gln Ala His Gly Leu Thr Pro Glu Gln Val Val Ala Ile Ala Ser
                420                 425                 430

His Asp Gly Gly Lys Gln Ala Leu Glu Thr Val Gln Arg Leu Leu Pro
                435                 440                 445

Val Leu Cys Gln Ala His Gly Leu Thr Pro Gln Gln Val Val Ala Ile
    450                 455                 460

Ala Ser Asn Gly Gly Gly Lys Gln Ala Leu Glu Thr Val Gln Arg Leu
465                 470                 475                 480

Leu Pro Val Leu Cys Gln Ala His Gly Leu Thr Pro Gln Gln Val Val
                485                 490                 495

Ala Ile Ala Ser Asn Gly Gly Gly Lys Gln Ala Leu Glu Thr Val Gln
                500                 505                 510

Arg Leu Leu Pro Val Leu Cys Gln Ala His Gly Leu Thr Pro Glu Gln
                515                 520                 525

Val Val Ala Ile Ala Ser His Asp Gly Gly Lys Gln Ala Leu Glu Thr
    530                 535                 540

Val Gln Arg Leu Leu Pro Val Leu Cys Gln Ala His Gly Leu Thr Pro
545                 550                 555                 560

Glu Gln Val Val Ala Ile Ala Ser His Asp Gly Gly Lys Gln Ala Leu
                565                 570                 575

Glu Thr Val Gln Arg Leu Leu Pro Val Leu Cys Gln Ala His Gly Leu
                580                 585                 590

Thr Pro Glu Gln Val Val Ala Ile Ala Ser Asn Ile Gly Gly Lys Gln
                595                 600                 605

Ala Leu Glu Thr Val Gln Ala Leu Leu Pro Val Leu Cys Gln Ala His
    610                 615                 620

Gly Leu Thr Pro Gln Gln Val Val Ala Ile Ala Ser Asn Asn Gly Gly
625                 630                 635                 640

Lys Gln Ala Leu Glu Thr Val Gln Arg Leu Leu Pro Val Leu Cys Gln
                645                 650                 655

Ala His Gly Leu Thr Pro Gln Gln Val Val Ala Ile Ala Ser Asn Gly
                660                 665                 670

Gly Gly Arg Pro Ala Leu Glu Ser Ile Val Ala Gln Leu Ser Arg Pro
                675                 680                 685

Asp Pro Ala Leu Ala Ala Leu Thr Asn Asp His Leu Val Ala Leu Ala
```

-continued

```
        690                 695                 700

Cys Leu Gly Gly Arg Pro Ala Leu Asp Ala Val Lys Lys Gly Leu Gly
705                 710                 715                 720

Asp Pro Ile Ser Arg Ser Gln Leu Val Lys Ser Glu Leu Glu Glu Lys
                725                 730                 735

Lys Ser Glu Leu Arg His Lys Leu Lys Tyr Val Pro His Glu Tyr Ile
                740                 745                 750

Glu Leu Ile Glu Ile Ala Arg Asn Ser Thr Gln Asp Arg Ile Leu Glu
                755                 760                 765

Met Lys Val Met Glu Phe Phe Met Lys Val Tyr Gly Tyr Arg Gly Lys
                770                 775                 780

His Leu Gly Gly Ser Arg Lys Pro Asp Gly Ala Ile Tyr Thr Val Gly
785                 790                 795                 800

Ser Pro Ile Asp Tyr Gly Val Ile Val Asp Thr Lys Ala Tyr Ser Gly
                805                 810                 815

Gly Tyr Asn Leu Pro Ile Gly Gln Ala Asp Glu Met Gln Arg Tyr Val
                820                 825                 830

Glu Glu Asn Gln Thr Arg Asn Lys His Ile Asn Pro Asn Glu Trp Trp
                835                 840                 845

Lys Val Tyr Pro Ser Ser Val Thr Glu Phe Lys Phe Leu Phe Val Ser
                850                 855                 860

Gly His Phe Lys Gly Asn Tyr Lys Ala Gln Leu Thr Arg Leu Asn His
865                 870                 875                 880

Ile Thr Asn Cys Asn Gly Ala Val Leu Ser Val Glu Glu Leu Leu Ile
                885                 890                 895

Gly Gly Glu Met Ile Lys Ala Gly Thr Leu Thr Leu Glu Glu Val Arg
                900                 905                 910

Arg Lys Phe Asn Asn Gly Glu Ile Asn Phe Ala Ala Asp
                915                 920                 925

<210> SEQ ID NO 28
<211> LENGTH: 925
<212> TYPE: PRT
<213> ORGANISM: artificial
<220> FEATURE:
<223> OTHER INFORMATION: CD22_T01-R

<400> SEQUENCE: 28

Met Gly Asp Pro Lys Lys Lys Arg Lys Val Ile Asp Ile Ala Asp Leu
1               5                   10                  15

Arg Thr Leu Gly Tyr Ser Gln Gln Gln Glu Lys Ile Lys Pro Lys
                20                  25                  30

Val Arg Ser Thr Val Ala Gln His His Glu Ala Leu Val Gly His Gly
                35                  40                  45

Phe Thr His Ala His Ile Val Ala Leu Ser Gln His Pro Ala Ala Leu
        50                  55                  60

Gly Thr Val Ala Val Lys Tyr Gln Asp Met Ile Ala Ala Leu Pro Glu
65                  70                  75                  80

Ala Thr His Glu Ala Ile Val Gly Val Gly Lys Gln Trp Ser Gly Ala
                85                  90                  95

Arg Ala Leu Glu Ala Leu Leu Thr Val Ala Gly Glu Leu Arg Gly Pro
                100                 105                 110

Pro Leu Gln Leu Asp Thr Gly Gln Leu Leu Lys Ile Ala Lys Arg Gly
                115                 120                 125

Gly Val Thr Ala Val Glu Ala Val His Ala Trp Arg Asn Ala Leu Thr
```

```
      130                 135                 140

Gly Ala Pro Leu Asn Leu Thr Pro Gln Gln Val Val Ala Ile Ala Ser
145                 150                 155                 160

Asn Gly Gly Gly Lys Gln Ala Leu Glu Thr Val Gln Arg Leu Leu Pro
                165                 170                 175

Val Leu Cys Gln Ala His Gly Leu Thr Pro Gln Gln Val Val Ala Ile
                180                 185                 190

Ala Ser Asn Gly Gly Gly Lys Gln Ala Leu Glu Thr Val Gln Arg Leu
                195                 200                 205

Leu Pro Val Leu Cys Gln Ala His Gly Leu Thr Pro Gln Gln Val Val
        210                 215                 220

Ala Ile Ala Ser Asn Asn Gly Gly Lys Gln Ala Leu Glu Thr Val Gln
225                 230                 235                 240

Arg Leu Leu Pro Val Leu Cys Gln Ala His Gly Leu Thr Pro Glu Gln
                245                 250                 255

Val Val Ala Ile Ala Ser Asn Ile Gly Gly Lys Gln Ala Leu Glu Thr
                260                 265                 270

Val Gln Ala Leu Leu Pro Val Leu Cys Gln Ala His Gly Leu Thr Pro
                275                 280                 285

Glu Gln Val Val Ala Ile Ala Ser Asn Ile Gly Gly Lys Gln Ala Leu
        290                 295                 300

Glu Thr Val Gln Ala Leu Leu Pro Val Leu Cys Gln Ala His Gly Leu
305                 310                 315                 320

Thr Pro Gln Gln Val Val Ala Ile Ala Ser Asn Gly Gly Gly Lys Gln
                325                 330                 335

Ala Leu Glu Thr Val Gln Arg Leu Leu Pro Val Leu Cys Gln Ala His
                340                 345                 350

Gly Leu Thr Pro Glu Gln Val Val Ala Ile Ala Ser His Asp Gly Gly
                355                 360                 365

Lys Gln Ala Leu Glu Thr Val Gln Arg Leu Leu Pro Val Leu Cys Gln
        370                 375                 380

Ala His Gly Leu Thr Pro Glu Gln Val Val Ala Ile Ala Ser Asn Ile
385                 390                 395                 400

Gly Gly Lys Gln Ala Leu Glu Thr Val Gln Ala Leu Leu Pro Val Leu
                405                 410                 415

Cys Gln Ala His Gly Leu Thr Pro Glu Gln Val Val Ala Ile Ala Ser
                420                 425                 430

His Asp Gly Gly Lys Gln Ala Leu Glu Thr Val Gln Arg Leu Leu Pro
                435                 440                 445

Val Leu Cys Gln Ala His Gly Leu Thr Pro Gln Gln Val Val Ala Ile
        450                 455                 460

Ala Ser Asn Gly Gly Gly Lys Gln Ala Leu Glu Thr Val Gln Arg Leu
465                 470                 475                 480

Leu Pro Val Leu Cys Gln Ala His Gly Leu Thr Pro Gln Gln Val Val
                485                 490                 495

Ala Ile Ala Ser Asn Asn Gly Gly Lys Gln Ala Leu Glu Thr Val Gln
                500                 505                 510

Arg Leu Leu Pro Val Leu Cys Gln Ala His Gly Leu Thr Pro Gln Gln
                515                 520                 525

Val Val Ala Ile Ala Ser Asn Gly Gly Gly Lys Gln Ala Leu Glu Thr
        530                 535                 540

Val Gln Arg Leu Leu Pro Val Leu Cys Gln Ala His Gly Leu Thr Pro
545                 550                 555                 560
```

```
Gln Gln Val Val Ala Ile Ala Ser Asn Asn Gly Gly Lys Gln Ala Leu
            565             570             575

Glu Thr Val Gln Arg Leu Leu Pro Val Leu Cys Gln Ala His Gly Leu
            580             585             590

Thr Pro Gln Gln Val Val Ala Ile Ala Ser Asn Asn Gly Gly Lys Gln
        595             600             605

Ala Leu Glu Thr Val Gln Arg Leu Leu Pro Val Leu Cys Gln Ala His
        610             615             620

Gly Leu Thr Pro Gln Gln Val Val Ala Ile Ala Ser Asn Gly Gly Gly
    625             630             635             640

Lys Gln Ala Leu Glu Thr Val Gln Arg Leu Leu Pro Val Leu Cys Gln
            645             650             655

Ala His Gly Leu Thr Pro Gln Gln Val Val Ala Ile Ala Ser Asn Gly
            660             665             670

Gly Gly Arg Pro Ala Leu Glu Ser Ile Val Ala Gln Leu Ser Arg Pro
            675             680             685

Asp Pro Ala Leu Ala Ala Leu Thr Asn Asp His Leu Val Ala Leu Ala
        690             695             700

Cys Leu Gly Gly Arg Pro Ala Leu Asp Ala Val Lys Lys Gly Leu Gly
    705             710             715             720

Asp Pro Ile Ser Arg Ser Gln Leu Val Lys Ser Glu Leu Glu Glu Lys
            725             730             735

Lys Ser Glu Leu Arg His Lys Leu Lys Tyr Val Pro His Glu Tyr Ile
            740             745             750

Glu Leu Ile Glu Ile Ala Arg Asn Ser Thr Gln Asp Arg Ile Leu Glu
            755             760             765

Met Lys Val Met Glu Phe Phe Met Lys Val Tyr Gly Tyr Arg Gly Lys
    770             775             780

His Leu Gly Gly Ser Arg Lys Pro Asp Gly Ala Ile Tyr Thr Val Gly
785             790             795             800

Ser Pro Ile Asp Tyr Gly Val Ile Val Asp Thr Lys Ala Tyr Ser Gly
            805             810             815

Gly Tyr Asn Leu Pro Ile Gly Gln Ala Asp Glu Met Gln Arg Tyr Val
            820             825             830

Glu Glu Asn Gln Thr Arg Asn Lys His Ile Asn Pro Asn Glu Trp Trp
            835             840             845

Lys Val Tyr Pro Ser Ser Val Thr Glu Phe Lys Phe Leu Phe Val Ser
        850             855             860

Gly His Phe Lys Gly Asn Tyr Lys Ala Gln Leu Thr Arg Leu Asn His
865             870             875             880

Ile Thr Asn Cys Asn Gly Ala Val Leu Ser Val Glu Glu Leu Leu Ile
            885             890             895

Gly Gly Glu Met Ile Lys Ala Gly Thr Leu Thr Leu Glu Glu Val Arg
            900             905             910

Arg Lys Phe Asn Asn Gly Glu Ile Asn Phe Ala Ala Asp
        915             920             925
```

<210> SEQ ID NO 29
<211> LENGTH: 925
<212> TYPE: PRT
<213> ORGANISM: artificial
<220> FEATURE:
<223> OTHER INFORMATION: CD20_T01-L

<400> SEQUENCE: 29

-continued

```
Met Gly Asp Pro Lys Lys Lys Arg Lys Val Ile Asp Ile Ala Asp Leu
1               5                   10                  15

Arg Thr Leu Gly Tyr Ser Gln Gln Gln Glu Lys Ile Lys Pro Lys
            20                  25                  30

Val Arg Ser Thr Val Ala Gln His His Glu Ala Leu Val Gly His Gly
        35                  40                  45

Phe Thr His Ala His Ile Val Ala Leu Ser Gln His Pro Ala Ala Leu
    50                  55                  60

Gly Thr Val Ala Val Lys Tyr Gln Asp Met Ile Ala Ala Leu Pro Glu
65                  70                  75                  80

Ala Thr His Glu Ala Ile Val Gly Val Gly Lys Gln Trp Ser Gly Ala
                85                  90                  95

Arg Ala Leu Glu Ala Leu Leu Thr Val Ala Gly Glu Leu Arg Gly Pro
            100                 105                 110

Pro Leu Gln Leu Asp Thr Gly Gln Leu Leu Lys Ile Ala Lys Arg Gly
            115                 120                 125

Gly Val Thr Ala Val Glu Ala Val His Ala Trp Arg Asn Ala Leu Thr
        130                 135                 140

Gly Ala Pro Leu Asn Leu Thr Pro Gln Gln Val Val Ala Ile Ala Ser
145                 150                 155                 160

Asn Gly Gly Gly Lys Gln Ala Leu Glu Thr Val Gln Arg Leu Leu Pro
                165                 170                 175

Val Leu Cys Gln Ala His Gly Leu Thr Pro Gln Gln Val Val Ala Ile
            180                 185                 190

Ala Ser Asn Gly Gly Gly Lys Gln Ala Leu Glu Thr Val Gln Arg Leu
            195                 200                 205

Leu Pro Val Leu Cys Gln Ala His Gly Leu Thr Pro Gln Gln Val Val
    210                 215                 220

Ala Ile Ala Ser Asn Asn Gly Gly Lys Gln Ala Leu Glu Thr Val Gln
225                 230                 235                 240

Arg Leu Leu Pro Val Leu Cys Gln Ala His Gly Leu Thr Pro Glu Gln
            245                 250                 255

Val Val Ala Ile Ala Ser His Asp Gly Gly Lys Gln Ala Leu Glu Thr
            260                 265                 270

Val Gln Arg Leu Leu Pro Val Leu Cys Gln Ala His Gly Leu Thr Pro
    275                 280                 285

Gln Gln Val Val Ala Ile Ala Ser Asn Gly Gly Gly Lys Gln Ala Leu
    290                 295                 300

Glu Thr Val Gln Arg Leu Leu Pro Val Leu Cys Gln Ala His Gly Leu
305                 310                 315                 320

Thr Pro Gln Gln Val Val Ala Ile Ala Ser Asn Asn Gly Gly Lys Gln
            325                 330                 335

Ala Leu Glu Thr Val Gln Arg Leu Leu Pro Val Leu Cys Gln Ala His
            340                 345                 350

Gly Leu Thr Pro Glu Gln Val Val Ala Ile Ala Ser His Asp Gly Gly
        355                 360                 365

Lys Gln Ala Leu Glu Thr Val Gln Arg Leu Leu Pro Val Leu Cys Gln
    370                 375                 380

Ala His Gly Leu Thr Pro Glu Gln Val Val Ala Ile Ala Ser His Asp
385                 390                 395                 400

Gly Gly Lys Gln Ala Leu Glu Thr Val Gln Arg Leu Leu Pro Val Leu
            405                 410                 415
```

-continued

```
Cys Gln Ala His Gly Leu Thr Pro Glu Gln Val Val Ala Ile Ala Ser
            420                 425                 430

Asn Ile Gly Gly Lys Gln Ala Leu Glu Thr Val Gln Ala Leu Leu Pro
            435                 440                 445

Val Leu Cys Gln Ala His Gly Leu Thr Pro Gln Gln Val Val Ala Ile
            450                 455                 460

Ala Ser Asn Gly Gly Gly Lys Gln Ala Leu Glu Thr Val Gln Arg Leu
465                 470                 475                 480

Leu Pro Val Leu Cys Gln Ala His Gly Leu Thr Pro Gln Gln Val Val
                485                 490                 495

Ala Ile Ala Ser Asn Gly Gly Gly Lys Gln Ala Leu Glu Thr Val Gln
                500                 505                 510

Arg Leu Leu Pro Val Leu Cys Gln Ala His Gly Leu Thr Pro Gln Gln
            515                 520                 525

Val Val Ala Ile Ala Ser Asn Gly Gly Gly Lys Gln Ala Leu Glu Thr
            530                 535                 540

Val Gln Arg Leu Leu Pro Val Leu Cys Gln Ala His Gly Leu Thr Pro
545                 550                 555                 560

Glu Gln Val Val Ala Ile Ala Ser His Asp Gly Gly Lys Gln Ala Leu
                565                 570                 575

Glu Thr Val Gln Arg Leu Leu Pro Val Leu Cys Gln Ala His Gly Leu
            580                 585                 590

Thr Pro Gln Gln Val Val Ala Ile Ala Ser Asn Gly Gly Gly Lys Gln
            595                 600                 605

Ala Leu Glu Thr Val Gln Arg Leu Leu Pro Val Leu Cys Gln Ala His
            610                 615                 620

Gly Leu Thr Pro Gln Gln Val Val Ala Ile Ala Ser Asn Asn Gly Gly
625                 630                 635                 640

Lys Gln Ala Leu Glu Thr Val Gln Arg Leu Leu Pro Val Leu Cys Gln
                645                 650                 655

Ala His Gly Leu Thr Pro Gln Gln Val Val Ala Ile Ala Ser Asn Gly
                660                 665                 670

Gly Gly Arg Pro Ala Leu Glu Ser Ile Val Ala Gln Leu Ser Arg Pro
            675                 680                 685

Asp Pro Ala Leu Ala Ala Leu Thr Asn Asp His Leu Val Ala Leu Ala
            690                 695                 700

Cys Leu Gly Gly Arg Pro Ala Leu Asp Ala Val Lys Lys Gly Leu Gly
705                 710                 715                 720

Asp Pro Ile Ser Arg Ser Gln Leu Val Lys Ser Glu Leu Glu Glu Lys
                725                 730                 735

Lys Ser Glu Leu Arg His Lys Leu Lys Tyr Val Pro His Glu Tyr Ile
            740                 745                 750

Glu Leu Ile Glu Ile Ala Arg Asn Ser Thr Gln Asp Arg Ile Leu Glu
            755                 760                 765

Met Lys Val Met Glu Phe Phe Met Lys Val Tyr Gly Tyr Arg Gly Lys
            770                 775                 780

His Leu Gly Gly Ser Arg Lys Pro Asp Gly Ala Ile Tyr Thr Val Gly
785                 790                 795                 800

Ser Pro Ile Asp Tyr Gly Val Ile Val Asp Thr Lys Ala Tyr Ser Gly
                805                 810                 815

Gly Tyr Asn Leu Pro Ile Gly Gln Ala Asp Glu Met Gln Arg Tyr Val
                820                 825                 830

Glu Glu Asn Gln Thr Arg Asn Lys His Ile Asn Pro Asn Glu Trp Trp
```

-continued

```
              835                840                845

Lys Val Tyr Pro Ser Ser Val Thr Glu Phe Lys Phe Leu Phe Val Ser
    850                855                860

Gly His Phe Lys Gly Asn Tyr Lys Ala Gln Leu Thr Arg Leu Asn His
865                870                875                880

Ile Thr Asn Cys Asn Gly Ala Val Leu Ser Val Glu Glu Leu Leu Ile
                885                890                895

Gly Gly Glu Met Ile Lys Ala Gly Thr Leu Thr Leu Glu Glu Val Arg
                900                905                910

Arg Lys Phe Asn Asn Gly Glu Ile Asn Phe Ala Ala Asp
            915                920                925
```

<210> SEQ ID NO 30
<211> LENGTH: 925
<212> TYPE: PRT
<213> ORGANISM: artificial
<220> FEATURE:
<223> OTHER INFORMATION: CD20_T01-R

<400> SEQUENCE: 30

```
Met Gly Asp Pro Lys Lys Lys Arg Lys Val Ile Asp Ile Ala Asp Leu
1               5                10                15

Arg Thr Leu Gly Tyr Ser Gln Gln Gln Glu Lys Ile Lys Pro Lys
                20                25                30

Val Arg Ser Thr Val Ala Gln His His Glu Ala Leu Val Gly His Gly
            35                40                45

Phe Thr His Ala His Ile Val Ala Leu Ser Gln His Pro Ala Ala Leu
    50                55                60

Gly Thr Val Ala Val Lys Tyr Gln Asp Met Ile Ala Ala Leu Pro Glu
65                70                75                80

Ala Thr His Glu Ala Ile Val Gly Val Gly Lys Gln Trp Ser Gly Ala
                85                90                95

Arg Ala Leu Glu Ala Leu Leu Thr Val Ala Gly Glu Leu Arg Gly Pro
                100                105                110

Pro Leu Gln Leu Asp Thr Gly Gln Leu Leu Lys Ile Ala Lys Arg Gly
            115                120                125

Gly Val Thr Ala Val Glu Ala Val His Ala Trp Arg Asn Ala Leu Thr
    130                135                140

Gly Ala Pro Leu Asn Leu Thr Pro Glu Gln Val Val Ala Ile Ala Ser
145                150                155                160

Asn Ile Gly Gly Lys Gln Ala Leu Glu Thr Val Gln Ala Leu Leu Pro
                165                170                175

Val Leu Cys Gln Ala His Gly Leu Thr Pro Gln Gln Val Val Ala Ile
            180                185                190

Ala Ser Asn Gly Gly Gly Lys Gln Ala Leu Glu Thr Val Gln Arg Leu
            195                200                205

Leu Pro Val Leu Cys Gln Ala His Gly Leu Thr Pro Gln Gln Val Val
    210                215                220

Ala Ile Ala Ser Asn Gly Gly Gly Lys Gln Ala Leu Glu Thr Val Gln
225                230                235                240

Arg Leu Leu Pro Val Leu Cys Gln Ala His Gly Leu Thr Pro Glu Gln
                245                250                255

Val Val Ala Ile Ala Ser Asn Ile Gly Gly Lys Gln Ala Leu Glu Thr
            260                265                270

Val Gln Ala Leu Leu Pro Val Leu Cys Gln Ala His Gly Leu Thr Pro
```

-continued

```
              275                 280                 285
Glu Gln Val Val Ala Ile Ala Ser Asn Ile Gly Gly Lys Gln Ala Leu
    290                 295                 300

Glu Thr Val Gln Ala Leu Leu Pro Val Leu Cys Gln Ala His Gly Leu
305                 310                 315                 320

Thr Pro Gln Gln Val Val Ala Ile Ala Ser Asn Asn Gly Gly Lys Gln
                325                 330                 335

Ala Leu Glu Thr Val Gln Arg Leu Leu Pro Val Leu Cys Gln Ala His
            340                 345                 350

Gly Leu Thr Pro Gln Gln Val Val Ala Ile Ala Ser Asn Gly Gly Gly
            355                 360                 365

Lys Gln Ala Leu Glu Thr Val Gln Arg Leu Leu Pro Val Leu Cys Gln
    370                 375                 380

Ala His Gly Leu Thr Pro Glu Gln Val Val Ala Ile Ala Ser Asn Ile
385                 390                 395                 400

Gly Gly Lys Gln Ala Leu Glu Thr Val Gln Ala Leu Leu Pro Val Leu
                405                 410                 415

Cys Gln Ala His Gly Leu Thr Pro Gln Gln Val Val Ala Ile Ala Ser
            420                 425                 430

Asn Gly Gly Gly Lys Gln Ala Leu Glu Thr Val Gln Arg Leu Leu Pro
            435                 440                 445

Val Leu Cys Gln Ala His Gly Leu Thr Pro Gln Gln Val Val Ala Ile
            450                 455                 460

Ala Ser Asn Asn Gly Gly Lys Gln Ala Leu Glu Thr Val Gln Arg Leu
465                 470                 475                 480

Leu Pro Val Leu Cys Gln Ala His Gly Leu Thr Pro Gln Gln Val Val
                485                 490                 495

Ala Ile Ala Ser Asn Gly Gly Gly Lys Gln Ala Leu Glu Thr Val Gln
            500                 505                 510

Arg Leu Leu Pro Val Leu Cys Gln Ala His Gly Leu Thr Pro Glu Gln
            515                 520                 525

Val Val Ala Ile Ala Ser His Asp Gly Gly Lys Gln Ala Leu Glu Thr
    530                 535                 540

Val Gln Arg Leu Leu Pro Val Leu Cys Gln Ala His Gly Leu Thr Pro
545                 550                 555                 560

Glu Gln Val Val Ala Ile Ala Ser His Asp Gly Gly Lys Gln Ala Leu
                565                 570                 575

Glu Thr Val Gln Arg Leu Leu Pro Val Leu Cys Gln Ala His Gly Leu
            580                 585                 590

Thr Pro Glu Gln Val Val Ala Ile Ala Ser Asn Ile Gly Gly Lys Gln
            595                 600                 605

Ala Leu Glu Thr Val Gln Ala Leu Leu Pro Val Leu Cys Gln Ala His
    610                 615                 620

Gly Leu Thr Pro Gln Gln Val Val Ala Ile Ala Ser Asn Gly Gly Gly
625                 630                 635                 640

Lys Gln Ala Leu Glu Thr Val Gln Arg Leu Leu Pro Val Leu Cys Gln
                645                 650                 655

Ala His Gly Leu Thr Pro Gln Gln Val Val Ala Ile Ala Ser Asn Gly
            660                 665                 670

Gly Gly Arg Pro Ala Leu Glu Ser Ile Val Ala Gln Leu Ser Arg Pro
            675                 680                 685

Asp Pro Ala Leu Ala Ala Leu Thr Asn Asp His Leu Val Ala Leu Ala
    690                 695                 700
```

-continued

```
Cys Leu Gly Gly Arg Pro Ala Leu Asp Ala Val Lys Lys Gly Leu Gly
705                 710                 715                 720

Asp Pro Ile Ser Arg Ser Gln Leu Val Lys Ser Glu Leu Glu Glu Lys
                725                 730                 735

Lys Ser Glu Leu Arg His Lys Leu Lys Tyr Val Pro His Glu Tyr Ile
            740                 745                 750

Glu Leu Ile Glu Ile Ala Arg Asn Ser Thr Gln Asp Arg Ile Leu Glu
            755                 760                 765

Met Lys Val Met Glu Phe Phe Met Lys Val Tyr Gly Tyr Arg Gly Lys
        770                 775                 780

His Leu Gly Gly Ser Arg Lys Pro Asp Gly Ala Ile Tyr Thr Val Gly
785                 790                 795                 800

Ser Pro Ile Asp Tyr Gly Val Ile Val Asp Thr Lys Ala Tyr Ser Gly
                805                 810                 815

Gly Tyr Asn Leu Pro Ile Gly Gln Ala Asp Glu Met Gln Arg Tyr Val
                820                 825                 830

Glu Glu Asn Gln Thr Arg Asn Lys His Ile Asn Pro Asn Glu Trp Trp
            835                 840                 845

Lys Val Tyr Pro Ser Ser Val Thr Glu Phe Lys Phe Leu Phe Val Ser
        850                 855                 860

Gly His Phe Lys Gly Asn Tyr Lys Ala Gln Leu Thr Arg Leu Asn His
865                 870                 875                 880

Ile Thr Asn Cys Asn Gly Ala Val Leu Ser Val Glu Glu Leu Leu Ile
                885                 890                 895

Gly Gly Glu Met Ile Lys Ala Gly Thr Leu Thr Leu Glu Glu Val Arg
                900                 905                 910

Arg Lys Phe Asn Asn Gly Glu Ile Asn Phe Ala Ala Asp
        915                 920                 925

<210> SEQ ID NO 31
<211> LENGTH: 3003
<212> TYPE: DNA
<213> ORGANISM: artificial
<220> FEATURE:
<223> OTHER INFORMATION: nt seq CAR22xCAR20

<400> SEQUENCE: 31
atggctctgc ccgtcaccgc tctgctgctg ccactggccc tgctgctgca cgcagcaaga        60
ccacaggtgc agctgcagca gagcggccct ggcctggtga agccaagcca gacactgtcc       120
ctgacctgcg ccatcagcgg cgattccgtg agctccaact ccgccgcctg gaattggatc       180
aggcagtccc cttctcgggg cctggagtgg ctgggaagga catactatcg gtctaagtgg       240
tacaacgatt atgccgtgtc tgtgaagagc agaatcacaa tcaaccctga cacctccaag       300
aatcagttct ctctgcagct gaatagcgtg acaccagagg acaccgccgt gtactattgc       360
gccagggagg tgaccggcga cctggaggat gcctttgaca tctggggcca gggcacaatg       420
gtgaccgtgt ctagcggagg aggaggatcc ggaggaggag atctggcgg cggcggcagc       480 gatatccaga tgacacagtc cccatcctct ctgagcgcct ccgtgggcga cagagtgaca       540
atcacctgta gggcctccca gaccatctgg tcttacctga actggtatca gcagaggccc       600
ggcaaggccc ctaatctgct gatctacgca gcaagctccc tgcagagcgg agtgccatcc       660
agattctctg gcaggggctc cggcacagac ttcaccctga ccatctctag cctgcaggcc       720
gaggacttcg ccacctacta ttgccagcag tcttatagca tcccccagac atttggccag       780
```

```
ggcaccaagc tggagatcaa gaccacaacc ccagcaccaa ggccacctac acctgcacca        840
accatcgcct ctcagcccct gagcctgaga cctgaggcat gtaggccagc agcaggagga        900
gcagtccata caaggggtct ggattttgca tgcgacatct acatctgggc acctctggca        960
ggaacatgtg gcgtgctcct gctcagcctg gtcatcaccc tgtactgcaa gagaggcagg       1020
aagaagctgc tgtatatctt caagcagccc ttcatgcgcc ccgtgcagac aacccaggag       1080
gaggatggct gctcctgtag gttcccagaa gaggaggagg gaggatgtga gctgcgcgtg       1140 aagtttttccc ggtctgccga cgcacctgca taccagcagg gccagaacca gctgtataac       1200
gagctgaatc tgggccggag agaggagtac gatgtgctgg acaagaggcg cggcagagat       1260
ccagagatgg gcggcaagcc ccggagaaag aaccctcagg agggcctgta caatgagctg       1320
cagaaggata agatggccga ggcctattct gagatcggca tgaagggaga gaggcgccgg       1380
ggcaagggac acgacggact gtaccaggga ctgagcacag ccaccaagga tacctatgac       1440
gccctgcata tgcaggcact gcctccaagg ggaagcggag ctactaactt cagcctgctg       1500
aagcaggctg agacgtgga ggagaaccct ggacctatgg ctctgcctgt caccgctctg       1560
ctgctgcccc tggctctgct gctgcacgcc gcacgcccg aagtccagct ggtcgaatct       1620
gggggcgggc tggtgcagcc aggaagatca ctgaggctga gctgcgccgc ttccggcttc       1680
accttcaacg actatgccat gcactgggtg agacaggctc ccggaaaggg cctggagtgg       1740
gtctctacca tcagttggaa ttccgggtct attggatatg ccgacagcgt gaaaggccgc       1800
ttcacaatct ctcgagataa cgctaagaaa agtctgtacc tgcagatgaa ttcactgagg       1860
gcagaggaca ctgcctgta ctattgcgcc aaggatattc agtacggcaa ctactattac       1920
gggatggacg tctgggggca gggaaccaca gtgaccgtca gctccggagg aggaggatcc       1980
ggaggaggag gaagcggagg aggaggatcc gagatcgtgc tgacacagag cccagccact       2040
ctgagtctgt cacccggcga acgagctaca ctgtcctgtc gggcaagcca gtccgtctct       2100
agttatctgg cttggtacca gcagaagcca ggacaggcac cacgactgct gatctacgat       2160
gctagcaaca gagcaacagg gattcctgca aggttctctg gcagtgggtc aggaactgac       2220
tttacactga ctatctcaag cctggagcct gaagatttcg ccgtgtatta ctgccagcag       2280
cggtccaatt ggccaatcac ctttggccag gggacacgcc tggagatcaa gactaccaca       2340
cctgctccac gaccacctac tccagcacct accattgctt ctcagcccct gagtctgcgg       2400
cctgaagcat gtagaccagc agcaggagga gcagtgcata ccagaggact ggactttgcc       2460
tgcgatatct atatttgggc accactggct ggaacttgtg gagtgctgct gctgtctctg       2520
gtcatcaccc tgtattgcaa gcgaggccgg aagaaactgc tgtacatttt caaacagcct       2580
tttatgagac cagtgcagac tacccaggag aagacggct gcagctgtag gttccccgag       2640
gaagaggaag ggggatgtga gctgagggtc aagtttagcc gctccgctga tgcacctgcc       2700
tatcagcagg ggcagaatca gctgtacaac gagctgaatc tgggacggag agaggaatac       2760
gacgtgctgg ataaaaggcg aggacgagat ccagaaatgg gagggaagcc ccgacggaaa       2820
aaccctcagg agggcctgta taatgaactg cagaaggaca aaatggctga ggcatactct       2880
gaaatcggaa tgaagggcga gagaaggcgc ggaaaaggcc acgatgggct gtatcaggga       2940
ctgagtaccg ccacaaagga cacctacgat gcactgcata tgcaggccct gccacccgg       3000 tga                                                                     3003
```

<210> SEQ ID NO 32
<211> LENGTH: 3003

<212> TYPE: DNA
<213> ORGANISM: artificial
<220> FEATURE:
<223> OTHER INFORMATION: nt seq CAR20xCAR22

<400> SEQUENCE: 32
atggctctgc ctgtcaccgc tctgctgctg cccctggctc tgctgctgca cgccgcacgc      60
cccgaagtcc agctggtcga atctggggggc gggctggtgc agccaggaag atcactgagg     120
ctgagctgcg ccgcttccgg cttcaccttc aacgactatg ccatgcactg ggtgagacag     180
gctcccggaa agggcctgga gtgggtctct accatcagtt ggaattccgg gtctattgga     240
tatgccgaca gcgtgaaagg ccgcttcaca atctctcgag ataacgctaa gaaaagtctg     300
tacctgcaga tgaattcact gagggcagag gacactgccc tgtactattg cgccaaggat     360
attcagtacg gcaactacta ttacgggatg gacgtctggg ggcagggaac cacagtgacc     420
gtcagctccg gaggaggagg atccggagga ggaggaagcg gaggaggagg atccgagatc     480
gtgctgacac agagcccagc cactctgagt ctgtcacccg gcgaacgagc tacactgtcc     540
tgtcgggcaa gccagtccgt ctctagttat ctggcttggt accagcagaa gccaggacag     600
gcaccacgac tgctgatcta cgatgctagc aacagagcaa cagggattcc tgcaaggttc     660
tctggcagtg ggtcaggaac tgactttaca ctgactatct caagcctgga gcctgaagat     720
ttcgccgtgt attactgcca gcagcggtcc aattggccaa tcacctttgg ccaggggaca     780
cgcctggaga tcaagactac cacacctgct ccacgaccac ctactccagc acctaccatt     840
gcttctcagc ccctgagtct gcggcctgaa gcatgtagac agcagcagcag gaggagcagtg     900 cataccagag gactggactt tgcctgcgat atctatattt gggcaccact ggctggaact     960
tgtggagtgc tgctgctgtc tctggtcatc accctgtatt gcaagcgagg ccggaagaaa    1020
ctgctgtaca ttttcaaaca gccttttatg agaccagtgc agactaccca ggaggaagac    1080
ggctgcagct gtaggttccc cgaggaagag aaggggggat gtgagctgag ggtcaagttt    1140
agccgctccg ctgatgcacc tgcctatcag caggggcaga atcagctgta caacgagctg    1200
aatctgggac ggagagagga atacgacgtg ctggataaaa ggcgaggacg agatccagaa    1260
atgggaggga agccccgacg gaaaaaccct caggagggcc tgtataatga actgcagaag    1320
gacaaaatgg ctgaggcata ctctgaaatc ggaatgaagg gcgagagaag gcgcggaaaa    1380
ggccacgatg gctgtatca gggactgagt accgccacaa aggacaccta cgatgcactg    1440
catatgcagg ccctgccacc ccgaggaagc ggagctacta acttcagcct gctgaagcag    1500
gctggagacg tggaggagaa ccctggacct atggctctgc ccgtcaccgc tctgctgctg    1560
ccactggccc tgctgctgca cgcagcaaga ccacaggtgc agctgcagca gagcggccct    1620
ggcctggtga gccaagcca gacactgtcc ctgacctgcg ccatcagcgg cgattccgtg    1680
agctccaact ccgccgcctg gaattggatc aggcagtccc cttctcgggg cctggagtgg    1740
ctgggaagga catactatcg gtctaagtgg tacaacgatt atgccgtgtc tgtgaagagc    1800
agaatcacaa tcaaccctga cacctccaag aatcagttct ctctgcagct gaatagcgtg    1860
acaccagagg acaccgccgt gtactattgc gccaggagg tgaccggcgga cctggaggat    1920 gcctttgaca tctggggcca gggcacaatg gtgaccgtgt ctagcggagg aggaggatcc    1980
ggaggaggag gatctggcgg cggcggcagc gatatccaga tgacacagtc cccatcctct    2040
ctgagcgcct ccgtgggcga cagagtgaca atcacctgta gggcctccca gaccatctgg    2100
tcttacctga actggtatca gcagaggccc ggcaaggccc taatctgct gatctacgca    2160

-continued

```
gcaagctccc tgcagagcgg agtgccatcc agattctctg gcaggggctc cggcacagac    2220
ttcaccctga ccatctctag cctgcaggcc gaggacttcg ccacctacta ttgccagcag    2280
tcttatagca tcccccagac atttggccag ggcaccaagc tggagatcaa gaccacaacc    2340
ccagcaccaa ggccacctac acctgcacca accatcgcct ctcagcccct gagcctgaga    2400
cctgaggcat gtaggccagc agcaggagga gcagtccata caaggggtct ggattttgca    2460
tgcgacatct acatctgggc acctctggca ggaacatgtg gcgtgctcct gctcagcctg    2520
gtcatcaccc tgtactgcaa gagaggcagg aagaagctgc tgtatatctt caagcagccc    2580
ttcatgcgcc ccgtgcagac aacccaggag gaggatggct gctcctgtag gttcccagaa    2640
gaggaggagg aggatgtga gctgcgcgtg aagtttttccc ggtctgccga cgcacctgca    2700
taccagcagg gccagaacca gctgtataac gagctgaatc tgggccggag agaggagtac    2760
gatgtgctgg acaagaggcg cggcagagat ccagagatgg gcggcaagcc ccggagaaag    2820
aaccctcagg agggcctgta caatgagctg cagaaggata agatggccga ggcctattct    2880
gagatcggca tgaagggaga gaggcgccgg ggcaaggac acgacggact gtaccaggga    2940
ctgagcacag ccaccaagga tacctatgac gccctgcata tgcaggcact gcctccaagg    3000
tga                                                                  3003

<210> SEQ ID NO 33
<211> LENGTH: 49
<212> TYPE: DNA
<213> ORGANISM: artificial
<220> FEATURE:
<223> OTHER INFORMATION: TRAC_T01-target

<400> SEQUENCE: 33
ttgtcccaca gatatccaga accctgaccc tgccgtgtac cagctgaga                  49

<210> SEQ ID NO 34
<211> LENGTH: 49
<212> TYPE: DNA
<213> ORGANISM: artificial
<220> FEATURE:
<223> OTHER INFORMATION: CD52_T01-target

<400> SEQUENCE: 34
ttcctcctac tcaccatcag cctcctggtt atggtacagg taagagcaa                  49

<210> SEQ ID NO 35
<211> LENGTH: 49
<212> TYPE: DNA
<213> ORGANISM: artificial
<220> FEATURE:
<223> OTHER INFORMATION: CD22_T01 target

<400> SEQUENCE: 35
tctggttttc ttccagatcc tcccaagaag gtgaccacag tgattcaaa                  49

<210> SEQ ID NO 36
<211> LENGTH: 49
<212> TYPE: DNA
<213> ORGANISM: artificial
<220> FEATURE:
<223> OTHER INFORMATION: CD20_T01 target

<400> SEQUENCE: 36
tttgctgcca tttctggaat gattctttca atcatggaca tacttaata                  49
```

```
<210> SEQ ID NO 37
<211> LENGTH: 588
<212> TYPE: DNA
<213> ORGANISM: artificial
<220> FEATURE:
<223> OTHER INFORMATION: IRES

<400> SEQUENCE: 37
gcccctctcc ctcccccccc cctaacgtta ctggccgaag ccgcttggaa taaggccggt      60
gtgcgtttgt ctatatgtta ttttccacca tattgccgtc ttttggcaat gtgagggccc     120
ggaaacctgg ccctgtcttc ttgacgagca ttcctagggg tctttcccct ctcgccaaag     180
gaatgcaagg tctgttgaat gtcgtgaagg aagcagttcc tctggaagct tcttgaagac     240
aaacaacgtc tgtagcgacc ctttgcaggc agcggaaccc cccacctggc gacaggtgcc     300
tctgcggcca aaagccacgt gtataagata cacctgcaaa ggcggcacaa ccccagtgcc     360
acgttgtgag ttggatagtt gtggaaagag tcaaatggct ctcctcaagc gtattcaaca     420
aggggctgaa ggatgcccag aaggtacccc attgtatggg atctgatctg gggcctcggt     480
gcacatgctt tacatgtgtt tagtcgaggt taaaaaaacg tctaggcccc ccgaaccacg     540
gggacgtggt tttcctttga aaaacacgat gataatatgg ccacaacc                  588

<210> SEQ ID NO 38
<211> LENGTH: 21
<212> TYPE: PRT
<213> ORGANISM: artificial
<220> FEATURE:
<223> OTHER INFORMATION: T2A peptide

<400> SEQUENCE: 38

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 39
<211> LENGTH: 23
<212> TYPE: PRT
<213> ORGANISM: artificial
<220> FEATURE:
<223> OTHER INFORMATION: E2A peptide

<400> SEQUENCE: 39

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 40
<211> LENGTH: 25
<212> TYPE: PRT
<213> ORGANISM: artificial
<220> FEATURE:
<223> OTHER INFORMATION: F2A peptide

<400> SEQUENCE: 40

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 41
```

```
<211> LENGTH: 11
<212> TYPE: PRT
<213> ORGANISM: artificial
<220> FEATURE:
<223> OTHER INFORMATION: CAR22 H-CDR1

<400> SEQUENCE: 41

Ser Gly Asp Ser Val Ser Ser Asn Ser Ala Ala
1               5                   10

<210> SEQ ID NO 42
<211> LENGTH: 9
<212> TYPE: PRT
<213> ORGANISM: artificial
<220> FEATURE:
<223> OTHER INFORMATION: CAR22 H-CDR2

<400> SEQUENCE: 42

Thr Tyr Tyr Arg Ser Lys Trp Tyr Asn
1               5

<210> SEQ ID NO 43
<211> LENGTH: 13
<212> TYPE: PRT
<213> ORGANISM: artificial
<220> FEATURE:
<223> OTHER INFORMATION: CAR22 H-CDR3

<400> SEQUENCE: 43

Ala Arg Glu Val Thr Gly Asp Leu Glu Asp Ala Phe Asp
1               5                   10

<210> SEQ ID NO 44
<211> LENGTH: 6
<212> TYPE: PRT
<213> ORGANISM: artificial
<220> FEATURE:
<223> OTHER INFORMATION: CAR22 L-CDR1

<400> SEQUENCE: 44

Gln Thr Ile Trp Ser Tyr
1               5

<210> SEQ ID NO 45
<211> LENGTH: 3
<212> TYPE: PRT
<213> ORGANISM: artificial
<220> FEATURE:
<223> OTHER INFORMATION: CAR22 L-CDR2

<400> SEQUENCE: 45

Ala Ala Ser
1

<210> SEQ ID NO 46
<211> LENGTH: 9
<212> TYPE: PRT
<213> ORGANISM: artificial
<220> FEATURE:
<223> OTHER INFORMATION: CAR22 L-CDR3

<400> SEQUENCE: 46

Gln Gln Ser Tyr Ser Ile Pro Gln Thr
1               5

<210> SEQ ID NO 47
<211> LENGTH: 8
```

-continued

```
<212> TYPE: PRT
<213> ORGANISM: artificial
<220> FEATURE:
<223> OTHER INFORMATION: CAR20 H-CDR1

<400> SEQUENCE: 47

Gly Phe Thr Phe Asn Asp Tyr Ala
1               5

<210> SEQ ID NO 48
<211> LENGTH: 8
<212> TYPE: PRT
<213> ORGANISM: artificial
<220> FEATURE:
<223> OTHER INFORMATION: CAR20 H-CDR2

<400> SEQUENCE: 48

Ile Ser Trp Asn Ser Gly Ser Ile
1               5

<210> SEQ ID NO 49
<211> LENGTH: 15
<212> TYPE: PRT
<213> ORGANISM: artificial
<220> FEATURE:
<223> OTHER INFORMATION: CAR20 H-CDR3

<400> SEQUENCE: 49

Ala Lys Asp Ile Gln Tyr Gly Asn Tyr Tyr Tyr Gly Met Asp Val
1               5                   10                  15

<210> SEQ ID NO 50
<211> LENGTH: 6
<212> TYPE: PRT
<213> ORGANISM: artificial
<220> FEATURE:
<223> OTHER INFORMATION: CAR20 L-CDR1

<400> SEQUENCE: 50

Gln Ser Val Ser Ser Tyr
1               5

<210> SEQ ID NO 51
<211> LENGTH: 3
<212> TYPE: PRT
<213> ORGANISM: artificial
<220> FEATURE:
<223> OTHER INFORMATION: CAR20 L-CDR2

<400> SEQUENCE: 51

Asp Ala Ser
1

<210> SEQ ID NO 52
<211> LENGTH: 9
<212> TYPE: PRT
<213> ORGANISM: artificial
<220> FEATURE:
<223> OTHER INFORMATION: CAR20 L-CDR3

<400> SEQUENCE: 52

Gln Gln Arg Ser Asn Trp Pro Ile Thr
1               5
```

DUAL CAR-T CELLS

CROSS-REFERENCE TO RELATED APPLICATIONS

This application is a National Stage application under 35 U.S.C. § 371 of International Application No. PCT/EP2021/071400, having an International Filing Date of Jul. 30, 2021, which claims benefit of priority to DK Application Serial No. PA202070509, filed Jul. 31, 2020. The disclosures of the prior applications are considered part of (and are incorporated by reference in) the disclosure of this application.

SEQUENCE LISTING

This application contains a Sequence Listing that has been submitted electronically as an ASCII text file named "47246-0013US1.txt." The ASCII text file, created on Jul. 28, 2021, is 110,191 bytes in size. The material in the ASCII text file is hereby incorporated by reference in its entirety.

FIELD

The present invention relates to the field of cell immunotherapy and more particularly to new engineered immune cells expressing two CARs directed against two different targets, useful in the treatment of cancers.

BACKGROUND

Approximately every 3 minutes one person in the United States (US) is diagnosed with a blood cancer. An estimated combined total of 178,520 people in the US are expected to be diagnosed with leukemia, lymphoma or myeloma in 2020. New cases of leukemia, lymphoma and myeloma are expected to account for 9.9 percent of the estimated 1,806,590 new cancer cases diagnosed in the US in 2020 (Cancer Facts & Figures, 2020. American Cancer Society).

The development of chimeric antigen receptor (CAR) T-cell therapy for hematological malignancies represents one of the most remarkable therapeutic advances in the past decade (Holstein et al, 2020, Clin. Pharmacol. Ther. 107(1): 112-122). Indeed, as a rapidly progressing field in oncology, the adoptive transfer of CAR-T cells has shown striking efficacy in the management of hematological malignancies and has been reported in a number of clinical trials.

Chimeric antigen receptors ("CAR") expressing immune cells are cells which have been genetically engineered to express CARs usually designed to recognize specific tumor antigens and kill the cancer cells that express these tumor antigens. It is not excluded that the CAR immune cells can activate the immune system to eliminate tumors. These are generally T cells expressing CARs ("CAR-T cells") or Natural Killer cells expressing CARs ("CAR-NK cells") or macrophages expressing CARs.

CARs are synthetic receptors consisting of a targeting moiety that is associated with one or more signalling domains in a single fusion molecule. In general, the binding moiety of a CAR consists of an antigen-binding domain derived from a monoclonal antibody, consisting of a single chain variable fragment (scFv), which contains the light and heavy variable fragments of a monoclonal antibody joined by a flexible linker. Binding moieties based on receptor or ligand domains have also been used successfully. The signalling domains for first generation CARs are derived from the cytoplasmic region of the CD3zeta or the Fc receptor gamma chains. First generation CARs have been shown to successfully redirect T cell cytotoxicity, however, they failed to provide prolonged expansion and anti-tumor activity in vivo. Signalling domains from co-stimulatory molecules including CD28, OX-40 (CD134), ICOS and 4-1BB (CD137) have been added alone (second generation) or in combination (third generation) to enhance survival and increase proliferation of CAR modified T cells. CARs have successfully allowed T cells to be redirected against antigens expressed at the surface of tumor cells from various malignancies including lymphomas and solid tumors (Jena, Dotti et al. 2010, Blood 116(7):1035-44).

Adoptive immunotherapy, which involves the transfer of autologous or allogeneic antigen-specific T cells generated ex vivo, is a promising strategy to treat viral infections and cancer as confirmed by the increase in the number of CAR-T cells approved by the US Food and Drug Administration (FDA) (e.g. Novartis' anti-CD19 CAR-T tisagenlecleucel (Kymriah™) for the treatment of precursor B-cell acute lymphoblastic leukemia, Kite Pharma's anti-CD19 CAR-T axicabtagene ciloleucel (Yescarta™) for certain types of large B-cell lymphoma in adult patients).

Despite the progress in research and development of CAR-T cell therapy, there still remains a need for improved CAR-T cells which could target a wider range of cancers as well as recurrent cancers and/or cancers for which the expression of the cancer-associated antigens are very variable and evolve with the time or during or after the treatments.

SUMMARY

The inventors have developed new CAR-T cells targeting CD20 and CD22 antigens, which can be activated by the tumor cells expressing CD20 and CD22 at variable levels, and constitute an improvement over CAR-T cells of the prior art.

A first aspect relates to a genetically engineered immune cell expressing a Chimeric Antigen Receptor (CAR) specific for CD22 (CAR22) and a Chimeric Antigen Receptor specific for CD20 (CAR20) at its cell surface, a) wherein said CAR22 comprises:
   i) at least one extracellular domain comprising:
      an antigen binding domain specific for CD22 comprising the Variable Heavy chain (VH) of SEQ ID NO: 11 and the Variable Ught chain (VL) of SEQ ID NO: 12, optionally a leader sequence,
      a hinge domain from CD8alpha,
   ii) a transmembrane domain from CD8alpha, and
   iii an intracellular domain comprising a 4-1BB stimulatory domain and a CD3zeta signalling domain; and
b) wherein said CAR20 comprises:
   i) at least one extracellular domain comprising:
      an antigen binding domain specific for CD20 comprising the Variable Heavy chain (VH) of SEQ ID NO: 15 and the Variable Light chain (VL) of SEQ ID NO: 16, optionally a leader sequence,
      a hinge domain from CD8alpha,
   ii) a transmembrane domain from CD8alpha, and
   iii) an intracellular domain comprising a 4-1BB stimulatory domain and a CD3zeta signalling domain.

In a particular aspect, said genetically engineered immune cell is a TCR negative T-cell.

Another aspect concerns a pharmaceutical composition comprising said engineered immune cells or a population of cells comprising said engineered immune cells, and a pharmaceutically acceptable excipient.

A still other aspect relates to an isolated polynucleotide comprising:

a) a nucleic acid encoding a CAR22 comprising:
    i) at least one extracellular domain comprising:
        an antigen binding domain specific for CD22 comprising the Variable Heavy chain (VH) of SEQ ID NO: 11 and the Variable Light chain (VL) of SEQ ID NO: 12, optionally a leader sequence,
        a hinge domain from CD8alpha,
    ii) a transmembrane domain from CD8alpha, and
    iii) an intracellular domain comprising a 4-1BB stimulatory domain and a CD3zeta signalling domain; and
b) a nucleic acid encoding a CAR20 comprising:
    i) at least one extracellular domain comprising:
        an antigen binding domain specific for CD20 comprising the Variable Heavy chain (VH) of SEQ ID NO: 15 and the Variable Light chain (VL) of SEQ ID NO: 16, optionally a leader sequence,
        a hinge domain from CD8alpha,
    ii) a transmembrane domain from CD8alpha, and
    iii) an intracellular domain comprising a 4-1BB stimulatory domain and a CD3zeta signalling domain.

Other aspects concern a vector comprising said polynucleotides, as well as a host cell comprising said polynucleotides or vector.

A still further aspect relates to a method of preparing said engineered immune cells.

Other aspects concern said engineered immune cells or population of cells for use as a medicament.

Another aspect relies on said engineered immune cells for use in the treatment of a cancer or an inflammatory disorder, in particular a cancer or inflammatory disorder associated with CD20 and/or CD22 expression.

Figure 1:
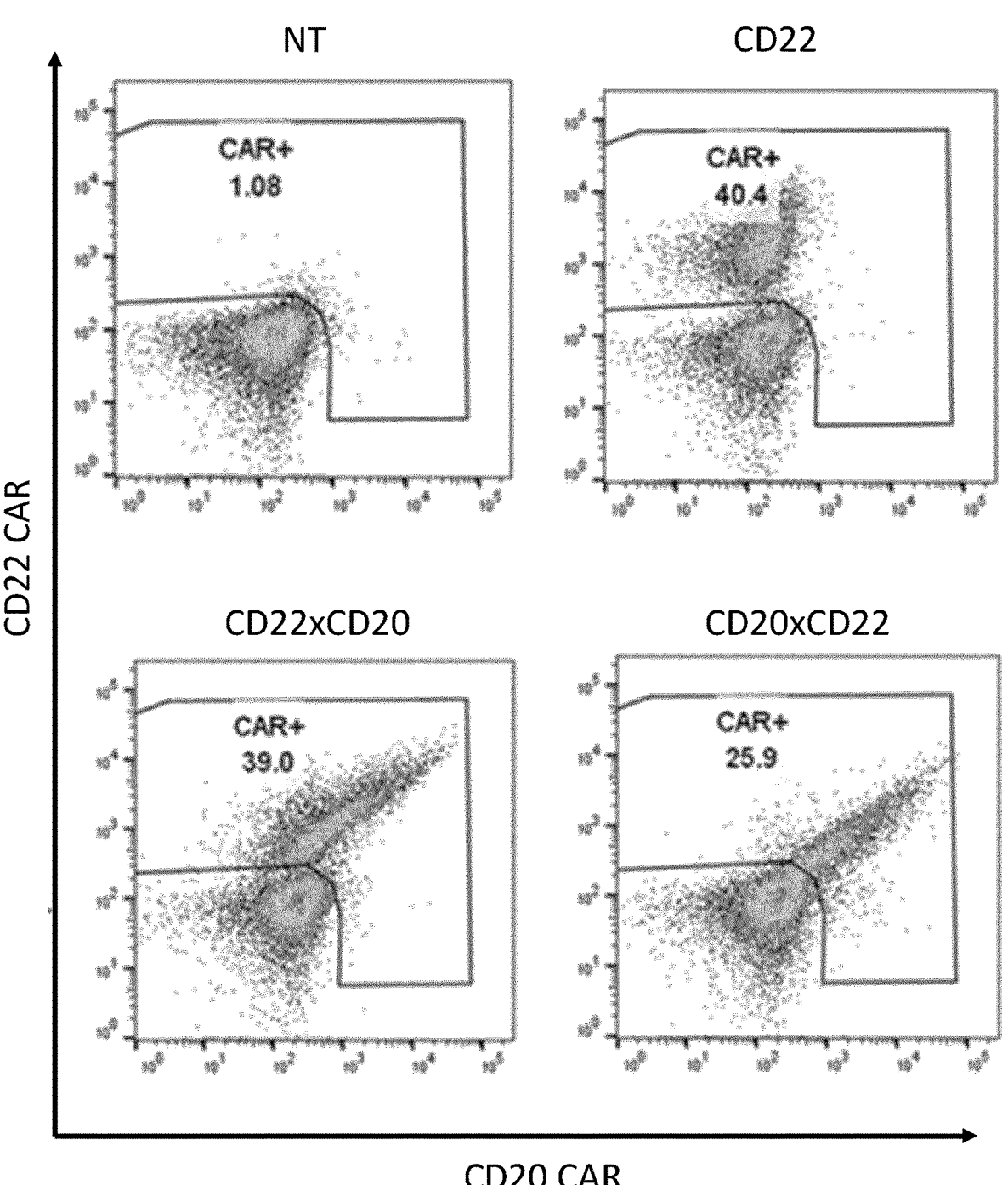
FIG. 1: CD20×CD22 or CD22×CD20 CAR detection. Flow cytometry analysis showing detection of CAR CD20 or CAR CD22 in non-transduced (NT), or T cells transduced with CD22 or CD22×CD20 or CD20×CD22 CAR constructs, using the protocol described in the Example.

Corresponding nomenclatures used along the specification and in the examples are as follows:
Anti-CD20 CAR=CAR20=CD20CAR
Anti-CD22 CAR=CAR22=CD22CAR
Anti-CD20 CAR/anti-CD22 CAR=CAR20×22 or CAR22×20=CD20×CD22 CAR or CD22×CD20CAR

DETAILED DESCRIPTION

Unless specifically defined herein, all technical and scientific terms used have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, New York: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

Definitions

As used herewith "an antigen associated with a disease state" refers to an antigen present or over-expressed in a given disease. In the case of the antigen being CD20 or CD22, a "CD20-associated disease" or a "CD22-associated disease" refers to a disease like a cancer or an inflammatory disorder for which the CD20 or CD22 antigen is generally present on the tumor cells or the cells provoking the inflammatory reaction (B-cells in particular). An antigen associated with a disease state, wherein said disease state is a cancer, i.e. "an antigen associated with a cancer" can be a tumor antigen as defined herewith.

As used herein, the term "CD20" refers to an antigenic determinant known to be detectable on B-cells. Human CD20 is also called membrane-spanning 4-domains, subfamily A, member 1 (MS4A1). The human and murine amino acid and nucleic acid sequences can be found in a public database, such as GenBank, UniProt and Swiss-Prot. For example, the amino acid sequence of human CD20 can be found at Accession Nos. NP_690605.1 and NP_068769.2, and the nucleic acid sequence encoding transcript variants 1 and 3 of the human CD20 can be found at Accession No. NM_152866.2 and NM_021950.3, respectively. In one aspect, the antigen-binding portion of the CAR recognizes and binds an antigen within the extracellular domain of the CD20 protein. In one aspect, the CD20 protein is expressed on a cancer cell. As used herein, "CD20" includes proteins comprising mutations, e.g., point mutations, fragments, insertions, deletions and splice variants of full length wild-type CD20.

As used herein, the term "CD22" refers to an antigenic determinant known to be detectable on leukemia precursor cells. The human and murine amino acid and nucleic acid sequences can be found in a public database, such as GenBank, UniProt and Swiss-Prot. For example, the amino acid sequences of isoforms 1-5 human CD22 can be found at Accession Nos. NP 001762.2, NP 001172028.1, NP 001172029.1, NP 001172030.1, and NP 001265346.1, respectively, and the nucleic acid sequence encoding variants 1-5 of the human CD22 can be found at Accession No. NM 001771.3, NM 001185099.1, NM 001185100.1, NM 001185101.1, and NM 001278417.1, respectively. In one aspect, the antigen-binding portion of the CAR recognizes and binds an antigen within the extracellular domain of the CD22 protein. In one aspect, the CD22 protein is expressed on a cancer cell. As used herein, "CD22" includes proteins comprising mutations, e.g., point mutations, fragments, insertions, deletions and splice variants of full length wild-type CD22.

The term "tumor antigen" is meant to cover "tumor-specific antigen" and "tumor associated antigen". Tumor-Specific Antigens (TSA) are generally present only on tumor cells and not on any other cell, while Tumor-Associated Antigens (TAA) are present on some tumor cells and also present on some normal cells. Tumor antigen, as meant herewith, also refers to mutated forms of a protein, which only appears in that form in tumors, while the non-mutated form is observed in non-tumoral tissues.

The term "extracellular antigen-binding domain" as used herein refers to an oligo- or polypeptide that is capable of binding a specific antigen. Preferably, the domain will be capable of interacting with a cell surface molecule. For example, the extracellular antigen-binding domain may be chosen to recognize an antigen that acts as a cell surface marker on target cells associated with a particular disease state. In a particular instance, said extracellular antigen-binding domain comprises a single chain antibody fragment (scFv) comprising the light ($V_L$) and the heavy ($V_H$) variable fragment of a target-antigen-specific monoclonal antibody joined by a flexible linker. The antigen binding domain of a CAR expressed on the cell surface of the engineered immune cells described herewith can be any domain that binds to the target antigen and that derives from, for instance, a monoclonal antibody, a recombinant antibody, a human antibody, a humanized antibody, and a functional fragment thereof.

By "chimeric antigen receptor" or "CAR" is generally meant a synthetic receptor comprising a targeting moiety that is associated with one or more signalling domains in a single fusion molecule. As defined herewith, the term "chimeric antigen receptor" covers single chain CARs as well as multi-chain CARs. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signalling domains for first generation CARs are derived from the cytoplasmic region of the CD3zeta or the Fc receptor gamma chains. First generation CARs have been shown to successfully redirect T cell cytotoxicity. However, they failed to provide prolonged expansion and anti-tumor activity in vivo. Signalling domains from co-stimulatory molecules including CD28, OX-40 (CD134), and 4-1BB (CD137) have been added alone (second generation) or in combination (third generation) to enhance survival and increase proliferation of CAR modified T cells. CARs are not necessarily only single chain polypeptides, multi-chain CARs are also possible. According to the multi-chain CAR architecture, for instance as described in VO2014039523, the signalling domains and co-stimulatory domains are located on different polypeptide chains. Such multi-chain CARs can be derived from FcɛRI, by replacing the high affinity IgE binding domain of FcɛRI alpha chain by an extracellular ligand-binding domain such as scFv, whereas the N- and/or C-termini tails of FcɛRI beta and/or gamma chains are fused to signal transducing domains and co-stimulatory domains respectively. The extracellular ligand binding domain has the role of redirecting T-cell specificity towards cell targets, while the signal transducing domains activate the immune cell response.

By "immune cell" is meant a cell of hematopoietic origin functionally involved in the initiation and/or execution of innate and/or adaptative immune response, such as typically CD45, CD3 or CD4 positive cells. The immune cell described herewith may be a dendritic cell, killer dendritic cell, a mast cell, macrophage, a natural killer cell (NK-cell), cytokine-induced killer cell (CIK cell), a B-cell or a T-cell selected from the group consisting of inflammatory T-lymphocytes, cytotoxic T-lymphocytes, regulatory T-lymphocytes or helper T-lymphocytes, gamma delta T cells, Natural killer T-cell ("NKT cell).

By "allogeneic" is meant that the cells originate from a donor, or are produced and/or differentiated from stem cells in view of being infused into patients having a different haplotype. Such immune cells are generally engineered to be less alloreactive and/or become more persistent with respect to their patient host More specifically, the method of engineering allogeneic immune cells can comprise the step of reducing or inactivating TCR expression into T-cells, or into the stem cells to be derived into T-cells. This can be obtained by different sequence specific-reagents, such as by gene silencing or gene editing techniques (nuclease, base editing, shRNA, RNAi . . . ).

"Originating from a donor" means that the T-cells do not necessarily come directly from the donor as fresh cells, but may derive from stem cells or cell lines obtained from initial donors, who are not the treated patient (i.e. different haplotypes).

By "primary cell" or "primary cells" are intended cells taken directly from living tissue (e.g. biopsy material) and established for growth in vitro for a limited amount of time, meaning that they can undergo a limited number of population doublings. Primary cells are opposed to continuous tumorigenic or artificially immortalized cell lines. Non-limiting examples of such cell lines are CHO-K1 cells; HEK293 cells; Caco2 cells; U2-OS cells; NIH 3T3 cells; NSO cells; SP2 cells; CHO-S cells; DG44 cells; K-562 cells, U-937 cells; MRC5 cells; IMR90 cells; Jurkat cells; HepG2 cells; HeLa cells; HT-1080 cells; HCT-116 cells; Hu-h7 cells; Huvec cells; Molt 4 cells.

Primary immune cells can be obtained from a number of non-limiting sources, including peripheral blood mononuclear cells (PBMC), bone marrow, lymph node tissue, cord blood, thymus tissue, tissue from a site of infection, ascites, pleural effusion, spleen tissue, and from tumors, such as tumor infiltrating lymphocytes. In some embodiments, said immune cell can be derived from a healthy donor, from a patient diagnosed with cancer or from a patient diagnosed with an infection. In another embodiment, said cell is part of a mixed population of immune cells which present different phenotypic characteristics, such as comprising CD4, CD8 and CD56 positive cells. Primary immune cells are provided from donors or patients through a variety of methods known in the art, as for instance by leukapheresis techniques as reviewed by Schwartz J. et al. (Guidelines on the use of therapeutic apheresis in clinical practice-evidence-based approach from the Writing Committee of the American Society for Apheresis: the sixth special issue (2013) *J Clin Apher.* 28(3):145-284).

The immune cells derived from stem cells are also regarded as primary immune cells according to the present invention, in particular those deriving from induced pluripotent stem cells (iPS) [Yamanaka, K. et al. (2008). "Generation of Mouse Induced Pluripotent Stem Cells Without Viral Vectors". *Science.* 322 (5903): 949-53]. Lentiviral expression of reprogramming factors has been used to induce multipotent cells from human peripheral blood cells [Staerk, J. et al. (2010). "Reprogramming of human peripheral blood cells to induced pluripotent stem cells". *Cell stem cell.* 7 (1): 20-4] [Loh, Y H. et al. (2010). "Reprogramming of T cells from human peripheral blood". *Cell stem cell.* 7 (1): 15-9].

The immune cells may be derived from human embryonic stem cells by techniques well known in the art that do not involve the destruction of human embryos [Chung et al. (2008) Human Embryonic Stem Cell lines generated without embryo destruction, *Cell Stem Cell* 2(2):113-117].

By "Genetic engineering" is meant any methods aiming to introduce, modify and/or withdraw genetic material from a cell. By "gene editing" is meant a genetic engineering allowing genetic material to be added, removed, or altered at specific locations (loci) in the genome, including punctual mutations. Gene editing generally involves sequence specific reagents.

By "identity", it is referred to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 80%, at least 85%, at least 90%, at least 95%, at least 98% or at least 99% identity to specific polypeptides described herein and preferably exhibiting substantially the same functions, as well as polynucleotide encoding such polypeptides, are contemplated. Unless otherwise stated, the present invention encompasses polypeptides and polynucleotides that have the same function and share at least 80%, generally at least 85%, preferably at least 90%, more preferably at least 95% and even more preferably at least 97% with those described herein.

The terms "patient" or "subject" and "donor" herein include all members of the animal kingdom including non-human primates and humans.

The invention is based on the surprising observation according to which a tumor cell expressing low levels of CD20 antigen and low levels of CD22 antigen, while not able to efficiently activate a CAR-T cell targeting either CD20 or CD22, could surprisingly activate a dual CAR-T cell expressing both a CAR targeting CD20 and a CAR targeting CD22.

Without willing to be bound by this theory, in these conditions, the total number of CD20 antigen molecules and CD22 antigen molecules per tumor site represents a threshold over which the dual CAR-T cell is activated, while a single CAR-T cell is not.

This could be represented as follows:

X=density of CD20 antigen molecules at the surface of the tumor, that are recognized by an anti-CD20 CAR (CAR20);

Y=density of CD22 antigen molecules at the surface of the tumor, that are recognized by an anti-CD22 CAR (CAR22);

X+Y=Z=density of CD20 antigen molecules and CD22 antigen molecules at the surface of the tumor;

T=density of antigen molecules bound to the T-cell that triggers said T-cell activation=threshold necessary for T-cell activation If Z>T, then T-cell activation occurs.

TABLE 1

Schematic representation of the relation between CAR T-cell activation and level of expression of the target antigens CD20 and CD22

| CAR-T cell | TUMOR | | | | | | | |
|---|---|---|---|---|---|---|---|---|
| | $CD20^{HIGH}$ | $CD22^{HIGH}$ | $CD20^{low}$ | $CD22^{low}$ | $CD20^{HIGH}$ $CD22^{HIGH}$ | $CD20^{low}$ $CD22^{HIGH}$ | $CD20^{HIGH}$ $CD22^{low}$ | $CD20^{low}$ $CD22^{low}$ |
| CAR20-T cell | X > T T-cell activation | X < T No T-cell activation | X < T No T-cell activation | X < T No T-cell activation | X > T T-cell activation | X < T No T-cell activation | X > T T-cell activation | X < T No T-cell activation |
| CAR22-T cell | Y < T No T-cell activation | Y > T T-cell activation | Y < T No T-cell activation | Y < T No T-cell activation | Y > T T-cell activation | Y > T T-cell activation | Y < T No T-cell activation | Y < T No T-cell activation |
| CAR20x22-T cell | Z > T T-cell activation | Z > T T-cell activation | Z < T No T-cell activation | Z < T No T-cell activation | Z > T T-cell activation | Z > T T-cell activation | Z > T T-cell activation | Z > T T-cell activation |

One of the advantages of the T cells expressing both CAR20 and CAR22 (dual "CAR20×22-T cell" or "CAR22× 20-T cell") of the invention is, thus, to be useful in immunotherapy to target an extended population of tumor cells having different levels of expression of the CD20 and/or CD22 antigens. Thus, not only the tumor cells having a low level of expression of the CD20 antigen and a high level of expression of the CD22 antigen, as well as those having a high level of expression of CD20 antigen and a low level of expression of the CD22 antigen would be targeted (and thus killed) by the dual CAR22×20-T cells of the invention but, surprisingly, also the cells having low levels of expression of the CD20 and the CD22 antigens would be targeted and, thus, killed.

Another advantage of the dual CAR-T cells of the invention relies on their utility in immunotherapy to treat a tumor that evolves by expressing more or less of the CD20 and CD22 antigens along time or during the treatment.

Another advantage of the dual CAR-T cells of the invention relies on their utility in immunotherapy to treat cancers characterized by a low expression of CD20 and CD22 antigens.

A still other advantage of the dual CAR-T cells of the invention is related to the synergistic effect of the two CARs, possibly by favouring and strengthening the immune synapse between the T-cells and their target tumor cells, possibly allowing a higher level of effector cytokines production.

On top of the above-mentioned advantages, the dual CAR-T cells of the invention are also useful to avoid CD20- and CD22-associated cancer relapse and/or antigen escape.

What has been observed and described herewith is likely to be generalizable so that dual CAR-T cells targeting two different tumor associated antigens could thus be useful in immunotherapy to target an extended population of tumor cells having different levels of expression of the tumor associated antigens as detailed above.

A further surprising effect of one aspect of the invention is related to the observation made by the inventors according to which an immune cell expressing a CAR20 and a CAR22 at its cell surface and having, integrated in the cell's genome, an exogenous nucleic acid comprising, from 5' to 3':

(i) a promoter,
(ii) a nucleic acid encoding said CAR20,
(iii) a nucleic acid encoding a self-cleaving peptide;
(iv) a nucleic acid encoding said CAR22,
whereby the same promoter controls the expression of said CAR20 and CAR22;
exhibits a higher tumor reduction in vivo compared to an immune cell expressing a CAR20 and a CAR22 at its cell surface and having, integrated in the cell's genome, an exogenous nucleic acid comprising, from 5' to 3':

(i) a promoter,
(ii) a nucleic acid encoding said CAR22,
(iii) a nucleic acid encoding a self-cleaving peptide;
(iv) a nucleic acid encoding said CAR20.

Immune Cells Expressing Anti-CD20 CAR and Anti-CD22 CAR

The immune cells described herewith are endowed with two synthetic chimeric antigen receptors (CARs) targeting the CD20 antigen and the CD22 antigen, respectively.

Anti-CD22 CAR (CAR22) and Anti-CD20 CAR (CAR20)

The immune cells described herewith are endowed with two synthetic CARs, which confers them a higher specificity toward a cell, such as a tumor comprising cells expressing the CD20 and/or CD22 antigen or toward inflammatory cells expressing the CD20 and/or CD22 antigen.

A recombinant chimeric antigen receptor is generally encoded by an exogenous polynucleotide which is introduced into the cell using viral vectors as per one of the transduction steps referred to elsewhere in the current application. A recombinant receptor encoded by an exogenous polynucleotide can also be introduced into the cell in the form of a plasmid or a PCR product.

In general, CAR polypeptides comprise an extracellular antigen-binding domain, a transmembrane domain, and an intracellular domain comprising a costimulatory domain and/or a primary signalling domain, wherein said antigen binding domain binds to the antigen associated with the disease state.

While the anti-CD20 and anti-CD22 CARs described herewith are not limited to a specific CAR structure, a nucleic acid that can be used to genetically engineer the immune cells generally encodes a CAR comprising: an extracellular antigen-binding domain that binds to an antigen associated with a disease state, a hinge, a transmembrane domain, and an intracellular domain comprising a stimulatory domain and/or a primary signalling domain. Generally, the extracellular antigen-binding domain is a scFv comprising a Heavy variable chain (VH) and a Light variable chain (VL) of an antibody binding to a specific antigen (e.g., to a tumor antigen) connected via a Linker. The transmembrane domain can be, for example, a CD8α transmembrane domain or a 4-1BB transmembrane domain. The stimulatory domain can be, for example, the 4-1BB stimulatory domain. The primary signalling domain can be, for example, the CD3ζ signalling domain.

In one embodiment, to avoid any recombination event within the construct comprising polynucleotides encoding two CARs comprising identical domains, the nucleotide acid sequences used to code for the same amino acid sequences present twice in the construct (e.g. the same transmembrane domain, the same stimulatory domain) are optimized using codon usage and code degeneracy so that the nucleotide sequences diverge.

TABLE 2

| Sequence of different domains typically present in a CAR | | |
|---|---|---|
| Functional domains | SEQ ID # | amino acid sequence |
| CD8α signal peptide (or sequence leader) | SEQ ID NO: 1 | MALPVTALLLPLALLLHAARP |
| Alternative signal peptide | SEQ ID NO: 2 | METDTLLLWVLLLWVPGSTG |

TABLE 2-continued

| Sequence of different domains typically present in a CAR | | |
| --- | --- | --- |
| Functional domains | SEQ ID # | amino acid sequence |
| FcγRIIIα hinge | SEQ ID NO: 3 | GLAVSTISSFFPPGYQ |
| CD8α hinge | SEQ ID NO: 4 | TTTPAPRPPTPAPTIASQPLSLRPEACRPAAGGAV HTRGLDFACD |
| IgG1 hinge | SEQ ID NO: 5 | EPKSPDKTHTCPPCPAPPVAGPSVFLFPPKPKDTL MIARTPEVTCVVVDVSHEDPEVKFNWYVDGVEVHN AKTKPREEQYNSTYRVVSVLTVLHQDWLNGKEYKC KVSNKALPAPIEKTISKAKGQPREPQVYTLPPSRD ELTKNQVSLTCLVKGFYPSDIAVEWESNGQPENNY KTTPPVLDSDGSFFLYSKLTVDKSRWQQGNVFSCS VMHEALHNHYTQKSLSLSPGK |
| CD8α transmembrane domain | SEQ ID NO: 6 | IYIWAPLAGTCGVLLLSLVITLYC |
| 4-1BB transmembrane domain | SEQ ID NO: 7 | IISFFLALTSTALLFLLFFLTLRFSVV |
| 4-1BB stimulatory domain | SEQ ID NO: 8 | KRGRKKLLYIFKQPFMRPVQTTQEEDGCSCRFPEE EEGGCEL |
| CD3ζ signalling domain | SEQ ID NO: 9 | RVKFSRSADAPAYQQGQNQLYNELNLGRREEYDVL DKRRGRDPEMGGKPRRKNPQEGLYNELQKDKMAEA YSEIGMKGERRRGKGHDGLYQGLSTATKDTYDALH MQALPPR |
| Linker | SEQ ID NO: 10 | GGGGSGGGGSGGGGS |

In one aspect, the antigen binding domain specific for CD20 comprises a Variable Heavy chain (VH) and a Variable Light chain (VL) linked by a linker, wherein said VH chain comprises the H-CDRs of SEQ ID NO: 47, SEQ ID NO: 48, and SEQ ID NO: 49, and said VL chain comprises the L-CDRs of SEQ ID NO: 50, SEQ ID NO: 51, and SEQ ID NO: 52.

For instance, the antigen binding domain specific for CD20 comprises a Variable Heavy chain (VH) and a Variable Light chain (VL) linked by a linker (forming the scFv of SEQ ID NO: 17), wherein said VH and VL chains comprise the H-CDRs of SEQ ID NO: 47, SEQ ID NO: 48, and SEQ ID NO: 49, and the L-CDRs of SEQ ID NO: 50, SEQ ID NO: 51, and SEQ ID NO: 52.

An anti-CD20 CAR as described herewith can comprise:

i) at least one extracellular domain comprising:

an antigen binding domain specific for CD20 comprising a Variable Heavy chain (VH) comprising an amino acid sequence having at least 80% identity, at least 90%, at least 95%, at least 97%, at least 99%, or 100% identity with SEQ ID NO: 15 and comprising the H-CDRs of amino acid sequences SEQ ID NO: 47, SEQ ID NO: 48, and SEQ ID NO: 49, and a Variable Light chain (VL) comprising an amino acid sequence having at least 80%, at least 90%, at least 95%, at least 97%, at least 99%, or 100% identity with SEQ ID NO: 16 and comprising the L-CDRs of amino acid sequences SEQ ID NO: 50, SEQ ID NO: 51, and SEQ ID NO: 52, optionally a leader sequence, a hinge domain from CD8alpha, ii) a transmembrane domain from CD8alpha, and iii) an intracellular domain comprising a 4-1BB stimulatory domain and a CD3zeta signalling domain.

In a particular aspect, the CAR targeting the CD20 antigen present on tumor cells, which is expressed by the genetically engineered immune cells described herewith, is as described in Tables 3 and 4.

TABLE 3

| Sequence of the VH and VL comprised in the scFv of an anti-CD20 CAR described herewith and illustrated in the Example section | | |
| --- | --- | --- |
| Region | SEQ ID # | amino acid sequence |
| Heavy variable region | SEQ ID NO: 15 | EVQLVESGGGLVQPGRSLRLSCAASGF TFNDYAMHWVRQAPGKGLEWVSTISWN SGSIGYADSVKGRFTISRDNAKKSLYL QMNSLRAEDTALYYCAKDIQYGNYYYG MDVWGQGTTVTVSS |
| Light variable region | SEQ ID NO: 16 | EIVLTQSPATLSLSPGERATLSCRASQ SVSSYLAWYQQKPGQAPRLLIYDASNR ATGIPARFSGSGSGTDFTLTISSLEPE DFAVYYCQQRSNWPITFGQGTRLEIK |

TABLE 4

| Structure of an anti-CD20 CAR described herewith and illustrated in the Example section | | | | | | | |
|---|---|---|---|---|---|---|---|
| CAR | CAR Structure | | | | | | |
| Designation CAR20 | signal peptide | VH | VL | CD8α hinge | CD8α TM | 4-1BB IC | CD3ζ CD |
| (SEQ ID NO: 18) | SEQ ID NO: 1 | SEQ ID NO: 15 | SEQ ID NO: 16 | SEQ ID NO: 4 | SEQ ID NO: 6 | SEQ ID NO: 8 | SEQ ID NO: 9 |

In one aspect, the antigen binding domain specific for CD22 comprises a Variable Heavy chain (VH) and a Variable Light chain (VL) linked by a linker, wherein said VH chain comprises the H-CDRs of SEQ ID NO: 41, SEQ ID NO: 42, and SEQ ID NO: 43, and said VL chain comprises the L-CDRs of SEQ ID NO: 44, SEQ ID NO: 45, and SEQ ID NO: 46.

For instance, the antigen binding domain specific for CD22 comprises a Variable Heavy chain (VH) and a Variable Light chain (VL) linked by a linker (forming the scFv of SEQ ID NO: 13), wherein said VH and VL chains comprise the H-CDRs of SEQ ID NO: 41, SEQ ID NO: 42, and SEQ ID NO: 43, and the L-CDRs of SEQ ID NO: 44, SEQ ID NO: 45, and SEQ ID NO: 48.

An anti-CD22 CAR as described herewith can comprise:

i) at least one extracellular domain comprising:

an antigen binding domain specific for CD22 comprising a Variable Heavy chain (VH) comprising an amino acid sequence having at least 80% identity, at least 90%, at least 95%, at least 97%, at least 99%, or 100% identity, with SEQ ID NO: 11 and comprising the H-CDRs of amino acid sequences SEQ ID NO: 41, SEQ ID NO: 42, and SEQ ID NO: 43, and a Variable Light chain (VL) comprising an amino acid sequence having at least 80%, at least 90%, at least 95%, at least 97%, at least 99%, or 100% identity, identity with SEQ ID NO: 12 and comprising the L-CDRs of amino acid sequences SEQ ID NO: 44, SEQ ID NO: 45, and SEQ ID NO: 46, optionally a leader sequence, a hinge domain from CD8alpha, ii) a transmembrane domain from CD8alpha, and iii an intracellular domain comprising a 4-1 BB stimulatory domain and a CD3zeta signalling domain.

In a particular aspect, the CAR targeting the CD22 antigen present on tumor cells, which is expressed by the genetically engineered immune cells described herewith, is described in Tables 5 and 6 below and in the Example section.

TABLE 5

| Sequence of the VH and VL comprised in the scFv of an anti-CD22 CAR described herewith and illustrated in the Example section | | |
|---|---|---|
| Region | SEQ ID # | amino acid sequence |
| Heavy variable region | SEQ ID NO: 11 | QVQLQQSGPGLVKPSQTLSLTCAISG DSVSSNSAAWNWIRQSPSRGLEWLGR TYYRSKWYNDYAVSVKSRITINPDTS KNQFSLQLNSVTPEDTAVYYCAREVT GDLEDAFDIWGQGTMVTVSS |
| Light variable region | SEQ ID NO: 12 | DIQMTQSPSSLSASVGDRVTITCRAS QTIWSYLNWYQQRPGKAPNLLIYAAS SLQSGVPSRFSGRGSGTDFTLTISSL QAEDFATYYCQQSYSIPQTFGQGTKL EIK |

TABLE 6

| Structure of an anti-CD22 CAR described herewith and illustrated in the Example section | | | | | | | |
|---|---|---|---|---|---|---|---|
| CAR | CAR Structure | | | | | | |
| Designation CAR22 | signal peptide | VH | VL | CD8α hinge | CD8α TM | 4-1BB IC | CD3ζ CD |
| (SEQ ID NO: 14) | SEQ ID NO: 1 | SEQ ID NO: 11 | SEQ ID NO: 12 | SEQ ID NO: 4 | SEQ ID NO: 6 | SEQ ID NO: 8 | SEQ ID NO: 9 |

15

Immune Cells Expressing CAR20 and CAR22

The engineered immune cells described herewith are endowed with the two synthetic chimeric antigen receptors (CARs) targeting the CD20 antigen and the CD22 antigen, respectively, as described herewith.

In a particular instance, said immune cells do not express any other CAR targeting another antigen than CD20 or CD22. More particularly, said immune cells do not express other CARs than the CAR22 and CAR20 described herewith.

The immune cell can be, for instance, a dendritic cell, killer dendritic cell, a mast cell, a macrophage, a NK-cell, a cytokine-induced Killer (CIK) cell, a B-cell or a T-cell selected from the group consisting of inflammatory T-lymphocytes, cytotoxic T-lymphocytes, regulatory T-lymphocytes or helper T-lymphocytes, gamma delta T cells, NKT cells and tumor infiltrating lymphocytes (TILL).

In a particular instance, the immune cell engineered to express the two CARs is selected from the group consisting of a T-cell, a NK-cell, and a macrophage.

In a more particular instance, the immune cell expressing the two CARs is a T-cell, for instance a cytotoxic T cell.

In a general instance, said immune cell is comprised in a population of cells, such as a population of immune cells, in particular a population of T-cells, a population of NK-cells, and/or a population of macrophages.

In a particular instance, said immune cell is a T-cell for use in off-the shelf immunotherapy.

In a particular instance, said engineered immune cell is a T-cell that is TCR negative (does not express TCR alpha at its cell surface).

In a particular instance said engineered T-cell expresses a short hairpin RNA (shRNA) or small interfering (siRNA) directed against a polynucleotide sequence encoding a component of TCR.

In another particular instance, said engineered T-cell is mutated in its TCR alpha and/or TCR beta alleles.

In particular, said engineered T-cell can have at least one allele encoding TCR alpha, TCR beta, and/or CD3 that has been inactivated by mutation.

In a still further instance, said engineered T-cell has at least one allele selected from β2m, PD1, CTLA4, dCK, CD52 and/or GR that has been inactivated.

In a still further instance, the engineered immune cell does not express the rituximab-specific mimotope of SEQ ID NO: 22.

A particular aspect concerns genetically engineered T-cells expressing a CAR22 and a CAR20 at their cell surface, wherein said CAR22 comprises the VH of SEQ ID NO: 11 and the VL of SEQ ID NO: 12, and said CAR20 comprises the VH of SEQ ID NO: 15 and the VL of SEQ ID NO: 16.

Still more particularly, are provided genetically engineered T-cells expressing a CAR22 and a CAR20 at their cell surface, wherein said CAR22 comprises the amino acid sequence of SEQ ID NO: 14, and wherein said CAR20 comprises the amino acid sequence of SEQ ID NO: 18.

A particular aspect concerns genetically engineered T-cells expressing a CAR22 and a CAR20 at their cell surface, wherein said CAR22 comprises the VH of SEQ ID NO: 11 and the VL of SEQ ID NO: 12, wherein said CAR20 comprises the VH of SEQ ID NO: 15 and the VL of SEQ ID NO: 16, and wherein said engineered T-cell has at least one allele encoding TCR alpha, TCR beta, and/or CD3 that has been inactivated by mutation.

A particular aspect concerns genetically engineered T-cells expressing a CAR22 and a CAR20 at their cell surface, wherein said CAR22 comprises the VH of SEQ ID NO: 11 and the VL of SEQ ID NO: 12, wherein said CAR20 comprises the VH of SEQ ID NO: 15 and the VL of SEQ ID NO: 16, and wherein said engineered T-cell has at least one allele encoding TCR alpha, TCR beta, and/or CD3 that has been inactivated by mutation and has at least one allele selected from CD52 and β2m that has been inactivated, in particular wherein said engineered T-cell has a TCR alpha and/or TCR beta and CD52 that have been inactivated by mutation.

Still more particularly, are provided genetically engineered T-cells expressing a CAR22 and a CAR20 at their cell surface, wherein said CAR22 comprises the amino acid sequence of SEQ ID NO: 14, wherein said CAR20 comprises the amino acid sequence of SEQ ID NO: 18, and wherein said engineered T-cell has at least one allele encoding TCR alpha, TCR beta, and/or CD3 that has been inactivated by mutation.

Still more particularly, are provided genetically engineered T-cells expressing a CAR22 and a CAR20 at their cell surface, wherein said CAR22 comprises the amino acid sequence of SEQ ID NO: 14, wherein said CAR20 comprises the amino acid sequence of SEQ ID NO: 18, and wherein said engineered T-cell has at least one allele encoding TCR alpha, TCR beta, and/or CD3 that has been inactivated by mutation and has at least one allele selected from CD52 and β2m that has been inactivated, in particular wherein said engineered T-cell has a TCR alpha and/or TCR beta and CD52 that have been inactivated by mutation.

Also provided herewith is a genetically engineered immune cell expressing a CAR22 and a CAR20 at its cell surface, as described above, wherein said CARs are encoded by an exogenous nucleic acid incorporated in said immune cell's genome and wherein said exogenous nucleic acid comprises, from 5' to 3':

(i) a promoter (such as the EF1alpha promoter)
(ii) a nucleic acid encoding said CAR20,
(iii) a nucleic acid encoding a self-cleaving peptide (such as P2A of SEQ ID NO: 19);
(iv) a nucleic acid encoding said CAR22,
whereby the same promoter controls the expression of said CAR20 and CAR22.

More particularly, is also provided a genetically engineered immune cell expressing a CAR22 and a CAR20 at its cell surface, as described above, wherein said exogenous nucleic acid comprises, from 5' to 3':

(i) a promoter (such as the EF1alpha promoter) that controls the expression of said CAR20;
(ii) a nucleic acid encoding said CAR20 comprising the signal peptide of SEQ ID NO: 1, the scFv of SEQ ID NO: 17, the CD8alpha hinge of SEQ ID NO: 4, the CD8alpha transmembrane domain of SEQ ID NO: 6, the 4-1BB co-stimulation domain of SEQ ID NO: 8, and the CD3 zeta signalisation domain of SEQ ID NO: 9);
(iii) a nucleic acid encoding a self-cleaving peptide (such as P2A of SEQ ID NO: 19);
(iv) a nucleic acid encoding said CAR22 comprising the signal peptide of SEQ ID NO: 1, the scFv of SEQ ID NO: 13, the CD8alpha hinge of SEQ ID NO: 4, the CD8alpha transmembrane domain of SEQ ID NO: 6, the 4-1BB co-stimulation domain of SEQ ID NO: 8, and the CD3 zeta signalisation domain of SEQ ID NO: 9;
whereby the same promoter controls the expression of said CAR20 and CAR22.

Alternatively, is also provided herewith a genetically engineered immune cell expressing a CAR22 and a CAR20 at its cell surface, as described above, wherein said CARs are encoded by an exogenous nucleic acid incorporated in said immune cell's genome and wherein said exogenous nucleic acid comprises, from 5' to 3':

(i) a promoter (such as the EF1alpha promoter)

(ii) a nucleic acid encoding said CAR22, (iii) a nucleic acid encoding a self-cleaving peptide (such as P2A of SEQ ID NO: 19);

(iv) a nucleic acid encoding said CAR20, whereby the same promoter controls the expression of said CAR20 and CAR22.

More particularly, is also provided a genetically engineered immune cell expressing a CAR22 and a CAR20 at its cell surface, as described above, wherein said exogenous nucleic acid comprises, from 5' to 3':

(i) a promoter (such as the EF1alpha promoter) that controls the expression of said CAR22;

(ii) the nucleic acid sequence encoding said CAR22 comprising the signal peptide of SEQ ID NO: 1, the scFv of SEQ ID NO: 13, the CD8alpha hinge of SEQ ID NO: 4, the CD8alpha transmembrane domain of SEQ ID NO: 6, the 4-1BB co-stimulation domain of SEQ ID NO: 8, and the CD3 zeta signalisation domain of SEQ ID NO: 9);

(iii) a nucleic acid encoding a self-cleaving peptide (such as P2A of SEQ ID NO: 19);

(iv) the nucleic acid encoding said CAR20 comprising the signal peptide of SEQ ID NO: 1, the scFv of SEQ ID NO: 17, the CD8alpha hinge of SEQ ID NO: 4, the CD8alpha transmembrane domain of SEQ ID NO: 6, the 4-1BB co-stimulation domain of SEQ ID NO: 8, and the CD3 zeta signalisation domain of SEQ ID NO: 9.

Methods of Preparation of the Genetically Engineered Immune Cells

The immune cells to be genetically engineered to express CAR20 and CAR22 as described herewith can be prepared by introducing one or more exogenous polynucleotides encoding said CARs. Said polynucleotide can be introduced into the cell using viral vectors via transduction. Said polynucleotide can also be introduced into the cell in the form of a plasmid or a PCR product.

Stable expression of CARs, in particular the CAR20 and CAR22 described herewith, in the above-described immune cells can be achieved using, for example, viral vectors (e.g., lentiviral vectors, retroviral vectors, Adeno-Associated Virus (AAV) vectors) or transposon/transposase systems or plasmids or PCR products integration. Other approaches include direct mRNA electroporation.

To deliver both CARs simultaneously into a cell, the polynucleotide(s) encoding anti-CD22 CAR (CAR22) and anti-CD20 CAR (CAR20) described herewith can have different structures such as:

(a) a polycistronic arrangement where both of the 2 transcription units are controlled by a unique promoter, have the same direction of transcription and are separated by a "self-cleaving" peptide such as a 2A peptide (e.g. P2A, T2A, E2A, F2A), (b) a bi-directional arrangement where each of the 2 transcription units is controlled by an independent promoter in a head to head configuration and are transcribed in opposite directions, and (c) a monocistronic arrangement with both scFV transcripts separated by a genomic spacer.

As used herein, a "polycistronic" mRNA refers to a single messenger RNA that comprises two or more coding sequences (i.e., cistrons) and encodes more than one protein. A polycistronic mRNA can comprise any element known in the art to allow for the translation of two or more genes from the same mRNA molecule including, but not limited to, a self-cleaving peptide like a P2A element, a T2A element, an E2A element, and an F2A element, or an IRES element.

A self-cleaving peptide to be comprised in the polynucleotides described herewith can be selected from a 2A peptide, a 2A like peptide, a P2A peptide, a E2A peptide, a F2A peptide, T2A peptide, in particular a 2A peptide, more particularly a P2A peptide of SEQ ID NO: 19, a T2A peptide of SEQ ID NO: 38, a E2A peptide of SEQ ID NO: 39, or a F2A peptide of SEQ ID NO: 40, still more particularly a P2A peptide of SEQ ID NO: 19.

An IRES states for "Internal ribosome entry sites", any IRES that allows the transcription and then translation of a coding sequence inserted in a gene could be used here. For example, an IRES comprised in the polynucleotides described herewith can have the SEQ ID NO: 37.

As described herewith the CAR20 and CAR22 can be encoded by two nucleic acids, wherein:

1) one nucleic acid encodes a CAR20 comprising:

i) at least one extracellular domain comprising:

an antigen binding domain specific for CD20 comprising a Variable Heavy chain (VH) comprising an amino acid sequence having at least 80%, at least 90%, at least 95%, at least 97%, at least 99%, or 100% identity with SEQ ID NO: 15 and comprising the H-CDRs of amino acid sequences SEQ ID NO: 47, SEQ ID NO: 48, and SEQ ID NO: 49, and a Variable Light chain (VL) comprising an amino acid sequence having at least 80%, at least 90%, at least 95%, at least 97%, at least 99%, or 100% identity with SEQ ID NO: 16 and comprising the L-CDRs of amino acid sequences SEQ ID NO: 50, SEQ ID NO: 51, and SEQ ID NO: 52, optionally a leader sequence, a hinge domain from CD8alpha, ii) a transmembrane domain from CD8alpha, and iii) an intracellular domain comprising a 4-1BB stimulatory domain and a CD3zeta signalling domain; and 2) another nucleic acid encodes a CAR22 comprising:

i) at least one extracellular domain comprising:

an antigen binding domain specific for CD22 comprising a Variable Heavy chain (VH) comprising an amino acid sequence having at least 80%, at least 90%, at least 95%, at least 97%, at least 99%, or 100% identity with SEQ ID NO: 11 and comprising the H-CDRs of amino acid sequences SEQ ID NO: 41, SEQ ID NO: 42, and SEQ ID NO: 43, and a Variable Light chain (VL) comprising an amino acid sequence having at least 80%, at least 90%, at least 95%, at least 97%, at least 99%, or 100% identity with SEQ ID NO: 12 and comprising the L-CDRs of amino acid sequences SEQ ID NO: 44, SEQ ID NO: 45, and SEQ ID NO: 46, optionally a leader sequence, a hinge domain from CD8alpha, ii) a transmembrane domain from CD8alpha, and iii) an intracellular domain comprising a 4-1BB stimulatory domain and a CD3zeta signalling domain.

In one instance, CAR22 and CAR20 are encoded by two independent nucleic acids a) and b) wherein:

(1) nucleic acid a) encodes a CAR22 comprising:

i) at least one extracellular domain comprising:

an antigen binding domain specific for CD22 comprising the Variable Heavy chain (VH) of SEQ ID NO: 11 and the Variable Light chain (VL) of SEQ ID NO: 12, optionally a leader sequence, a hinge domain from CD8alpha, ii) a transmembrane domain from CD8alpha, and iii) an intracellular domain comprising a 4-1BB stimulatory domain and a CD3zeta signalling domain; and (2) nucleic acid b) encodes a CAR20 comprising:

i) at least one extracellular domain comprising: –an antigen binding domain specific for CD20 comprising the Variable Heavy chain (VH) of SEQ ID NO: 15 and the Variable Light chain (VL) of SEQ ID NO: 16, optionally a leader sequence, a hinge domain from CD8alpha, ii) a transmembrane domain from CD8alpha, and iii) an intracellular domain comprising a 4-1BB stimulatory domain and a CD3zeta signalling domain.

In a particular instance, is provided an isolated polynucleotide comprising:

a) a nucleic acid encoding a CAR22 comprising:

i) at least one extracellular domain comprising:

an antigen binding domain specific for CD22 comprising the Variable Heavy chain (VH) of SEQ ID NO: 11 and the Variable Light chain (VL) of SEQ ID NO: 12, optionally a leader sequence, a hinge domain from CD8alpha, ii) a transmembrane domain from CD8alpha, and iii) an intracellular domain comprising a 4-1BB stimulatory domain and a CD3zeta signalling domain; and b) a nucleic acid encoding a CAR20 comprising:

i) at least one extracellular domain comprising:

an antigen binding domain specific for CD20 comprising the Variable Heavy chain (VH) of SEQ ID NO: 15 and the Variable Light chain (VL) of SEQ ID NO: 16, optionally a leader sequence, a hinge domain from CD8alpha, ii) a transmembrane domain from CD8alpha, and iii) an intracellular domain comprising a 4-1BB stimulatory domain and a CD3zeta signalling domain.

In a further instance, the nucleic acids of a) and b) are on a single nucleic acid molecule and the isolated polynucleotide comprises a nucleic acid sequence encoding a self-cleaving peptide (such as P2A, T2A, E2A, F2A) located between the nucleic acids of a) and b).

Thus, in a general aspect, disclosed herewith is a polynucleotide comprising, from 5' to 3':

(i) a promoter (such as the EF1alpha promoter)

(ii) a nucleic acid encoding a CAR20 as described herewith, (iii) a nucleic acid encoding a self-cleaving peptide (such as P2A of SEQ ID NO: 19);

(iv) a nucleic acid encoding a CAR22 as described herewith, whereby the same promoter controls the expression of said CAR20 and CAR22.

Also disclosed herewith is a polynucleotide comprising, from 5' to 3':

(i) a promoter (such as the EF1alpha promoter)

(ii) a nucleic acid encoding a CAR22 as described herewith, (iii) a nucleic acid encoding a self-cleaving peptide (such as P2A of SEQ ID NO: 19);

(iv) a nucleic acid encoding a CAR20 as described herewith, whereby the same promoter controls the expression of said CAR20 and CAR22.

In a particular instance, the isolated polynucleotide described herewith does not comprise a nucleic acid encoding a further CAR than said CAR22 and CAR20.

In a particular instance, the isolated polynucleotide described herewith does not comprise a nucleic acid encoding the rituximab-specific mimotope of SEQ ID NO: 22.

In one instance, the isolated polynucleotide encoding a CAR20 and CAR22 as described herewith comprises:

a) a promoter (such as the EF1alpha promoter) that controls the expression of said CAR20, followed by a nucleic acid encoding said CAR20, wherein said CAR20 comprises:

i) at least one extracellular domain comprising:

an antigen binding domain specific for CD20 comprising a Variable Heavy chain (VH) comprising an amino acid sequence having at least 80%, at least 90%, at least 95%, at least 97%, at least 99%, or 100% identity with SEQ ID NO: 15 and comprising the H-CDRs of amino acid sequences SEQ ID NO: 47, SEQ ID NO: 48, and SEQ ID NO: 49, and a Variable Light chain (VL) comprising an amino acid sequence having at least 80%, at least 90%, at least 95%, at least 97%, at least 99%, or 100% identity with SEQ ID NO: 16 and comprising the L-CDRs of amino acid sequences SEQ ID NO: 50, SEQ ID NO: 51, and SEQ ID NO: 52, optionally a leader sequence, a hinge domain from CD8alpha, ii) a transmembrane domain from CD8alpha, and iii) an intracellular domain comprising a 4-1BB stimulatory domain and a CD3zeta signalling domain; and b) a nucleic acid encoding a CAR22, wherein said CAR22 comprises:

i) at least one extracellular domain comprising:

an antigen binding domain specific for CD22 comprising a Variable Heavy chain (VH) comprising an amino acid sequence having at least 80%, at least 90%, at least 95%, at least 97%, at least 99%, or 100% identity with SEQ ID NO: 11 and comprising the H-CDRs of amino acid sequences SEQ ID NO: 41, SEQ ID NO: 42, and SEQ ID NO: 43, and a Variable Light chain (VL) comprising an amino acid sequence having at least 80%, at least 90%, at least 95%, at least 97%, at least 99%, or 100% identity with SEQ ID NO: 12 and comprising the L-CDRs of amino acid sequences SEQ ID NO: 44, SEQ ID NO: 45, and SEQ ID NO: 46, optionally a leader sequence, a hinge domain from CD8alpha, ii) a transmembrane domain from CD8alpha, and iii) an intracellular domain comprising a 4-1BB stimulatory domain and a CD3zeta signalling domain;

wherein said nucleic acids of a) and b) are on a single nucleic acid molecule and wherein a nucleic acid sequence encoding a self-cleaving peptide (such as P2A, T2A, E2A, or F2A) is located between said nucleic acids of a) and b).

In an alternative instance, the isolated polynucleotide encoding a CAR20 and CAR22 as described herewith comprises:

a) a promoter (such as the EF1alpha promoter) that controls the expression of said CAR22, followed by a nucleic acid encoding said CAR22, wherein said CAR22 is composed of:

i) at least one extracellular domain comprising:

an antigen binding domain specific for CD22 comprising a Variable Heavy chain (VH) comprising an amino acid sequence having at least 80%, at least 90%, at least 95%, at least 97%, at least 99%, or 100% identity with SEQ ID NO: 11 and comprising the H-CDRs of amino acid sequences SEQ ID NO: 41, SEQ ID NO: 42, and SEQ ID NO: 43, and a Variable Light chain (VL) comprising an amino acid sequence having at least 80%, at least 90%, at least 95%, at least 97%, at least 99%, or 100% identity with SEQ ID NO: 12 and comprising the L-CDRs of amino acid sequences SEQ ID NO: 44, SEQ ID NO: 45, and SEQ ID NO: 46, optionally a leader sequence, a hinge domain from CD8alpha, ii) a transmembrane domain from CD8alpha, and iii) an intracellular domain comprising a 4-1BB stimulatory domain and a CD3zeta signalling domain; and b) a nucleic acid encoding a CAR20, wherein said CAR20 comprises:

i) at least one extracellular domain comprising:

an antigen binding domain specific for CD20 comprising a Variable Heavy chain (VH) comprising an amino acid sequence having at least 80%, at least 90%, at least 95%, at least 97%, at least 99%, or 100% identity with SEQ ID NO: 15 and comprising the H-CDRs of amino acid sequences SEQ ID NO: 47, SEQ ID NO: 48, and SEQ ID NO: 49, and a Variable Light chain (VL) comprising an amino acid sequence having at least 80%, at least 90%, at least 95%, at least 97%, at least 99%, or 100% identity with SEQ ID NO: 16 and comprising the L-CDRs of amino acid sequences SEQ ID NO: 50, SEQ ID NO: 51, and SEQ ID NO: 52, optionally a leader sequence, a hinge domain from CD8alpha, ii) a transmembrane domain from CD8alpha, and iii) an intracellular domain comprising a 4-1BB stimulatory domain and a CD3zeta signalling domain;

wherein said nucleic acids of a) and b) are on a single nucleic acid molecule and wherein a nucleic acid sequence encoding a self-cleaving peptide (such as P2A, T2A, E2A, or F2A) is located between said nucleic acids of a) and b).

In a still further instance, the isolated polynucleotide encoding a CAR20 and CAR22 as described herewith comprises:

a) a nucleic acid encoding a CAR22, comprising a promoter (such as the EF1alpha promoter) that controls the expression of said CAR22 composed of the signal peptide of SEQ ID NO: 1, the scFv of SEQ ID NO: 13, the CD8alpha hinge of SEQ ID NO: 4, the CD8alpha transmembrane domain of SEQ ID NO: 6, the 4-1BB co-stimulation domain of SEQ ID NO: 8, and the CD3 zeta signalisation domain of SEQ ID NO: 9;

b) a nucleic acid encoding a CAR20 composed of the signal peptide of SEQ ID NO: 1, the scFv of SEQ ID NO: 17, the CD8alpha hinge of SEQ ID NO: 4, the CD8alpha transmembrane domain of SEQ ID NO: 6, the 4-1BB co-stimulation domain of SEQ ID NO: 8, and the CD3 zeta signalisation domain of SEQ ID NO: 9; and c) a nucleic acid encoding a self-cleaving peptide (such as P2A of SEQ ID NO: 19) placed between the nucleic acid of a) and the nucleic acid of b), allowing the simultaneous expression of said CAR20 and CAR22.

In a still further instance, is provided the isolated polynucleotide encoding a CAR20 and CAR22 as described herewith comprises:

a) a nucleic acid encoding a CAR20, comprising a promoter (such as the EF1alpha promoter) that controls the expression of said CAR20 composed of the signal peptide of SEQ ID NO: 1, the scFv of SEQ ID NO: 17, the CD8alpha hinge of SEQ ID NO: 4, the CD8alpha transmembrane domain of SEQ ID NO: 6, the 4-1BB co-stimulation domain of SEQ ID NO: 8, and the CD3 zeta signalisation domain of SEQ ID NO: 9;

b) a nucleic acid encoding a CAR22 composed of the signal peptide of SEQ ID NO: 1, the scFv of SEQ ID NO: 13, the CD8alpha hinge of SEQ ID NO: 4, the CD8alpha transmembrane domain of SEQ ID NO: 6, the 4-1BB co-stimulation domain of SEQ ID NO: 8, and the CD3 zeta signalisation domain of SEQ ID NO: 9; and c) a nucleic acid encoding a self-cleaving peptide (such as P2A of SEQ ID NO: 19) placed between the nucleic acid of a) and the nucleic acid of b), allowing the simultaneous expression of said CAR22 and CAR20.

In a still further instance is provided an isolated polynucleotide encoding a CAR20 and CAR22 comprising the nucleic acid sequence of SEQ ID NO: 31 (CAR22×CAR20 construct).

In another particular instance, is provided an isolated polynucleotide encoding a CAR20 and CAR22 comprising the nucleic acid sequence of SEQ ID NO: 32 (CAR20× CAR22 construct).

Also disclosed herewith is a vector comprising any of the isolated polynucleotides described herewith.

Also disclosed herewith is a host cell comprising the vector described herewith.

A population of immune cells to be engineered is generally extracted from a patient's or healthy donor's blood by apheresis and further engineered to express a chimeric antigen receptor at their surface. Alternatively, a population of immune cells to be engineered could derive from cord blood cells or from stem cells, which are further engineered to express a chimeric antigen receptor at their surface.

Said CAR-expressing immune cells may derive from a patient's or a compatible donor's immune cells which have been engineered to express a specific CAR at their surface.

Said CAR-expressing immune cells can also derive from stem cells, such as iPS cells, originating from such patient or compatible donor or from tumor infiltrating lymphocytes (TILL).

In other aspects, said CAR-expressing immune cells are so-called "off the shelf" immune cells compositions, whereby immune cells not specially belonging to the patient to be treated have been engineered to express a CAR and to become suitable for use in an allogeneic therapeutic treatment.

By "allogeneic" is meant that the cells originate from a donor, or are produced and/or differentiated from stem cells in view of being infused into patients having a different haplotype.

Such immune cells are generally engineered to be less alloreactive and/or become more persistent with respect to their patient host. More specifically, the method of engineering allogeneic immune cells can comprise the step of reducing or inactivating TCR expression into T-cells, or into the stem cells to be derived into T-cells. This can be obtained by different sequence specific-reagents, such as by gene silencing or gene editing techniques (nuclease, base editing, RNAi . . . ).

The applicant has formerly made available robust protocols and gene editing strategies to produce allogeneic therapeutic grade T-cells from PBMCs, especially by providing very safe and specific endonuclease reagents under the form of TALE-nucleases (TALEN®). The production of so-called "universal T-cells", which are [TCR]$^{negative}$ T-cells from donors was achieved and successfully injected to patients with reduced Graft versus Host Disease (GVhD) (Poirot et al. 2015, *Cancer. Res.* 75 (18): 3853-3864; Qasim et al., 2017, *Science Translational* 9(374)). Meanwhile, inactivation of TCR or β2m components in primary T-cells can be combined with the inactivation of further genes encoding checkpoint inhibitor proteins, such as described for instance in WO02014184744.

In further instances, the engineered immune cell can be further modified to confer resistance to at least one immune suppressive drug, such as by inactivating CD52 that is the target of anti-CD52 antibody (e.g.: alemtuzumab), as described for instance in WO2013176915.

In further instances, the engineered immune cell can be further modified to confer resistance to and/or a chemotherapy drug, in particular a purine analogue drug, for example by inactivating DCK as described in WO201575195.

In further instances, the engineered immune cell can be further modified to improve its persistence or its lifespan into the patient, in particular inactivating a gene encoding MHC-I component(s) such as HLA or β2m, such as described in WO2015136001 or by Liu et al. (2017, *Cell Res* 27:154-157).

In still further instances, the engineered immune cell is mutated to improve its CAR-dependent immune activation, in particular to reduce or suppress the expression of immune checkpoint proteins and/or their receptors thereof, such as PD1 or CTLA4 as described in WO2014184744.

Pharmaceutical Compositions

One aspect relates to a pharmaceutical composition comprising the genetically engineered immune cells expressing a Chimeric Antigen Receptor (CAR) specific for CD22 (CAR22) and a Chimeric Antigen Receptor specific for CD20 (CAR20) at their cell surface as described herewith, and a pharmaceutically acceptable excipient.

Also disclosed is a pharmaceutical composition comprising a population of immune cells comprising genetically engineered immune cells expressing a Chimeric Antigen Receptor (CAR) specific for CD22 (CAR22) and a Chimeric Antigen Receptor specific for CD20 (CAR20) at their cell surface as described herewith, and a pharmaceutical acceptable excipient.

A particular aspect concerns a pharmaceutical composition comprising the genetically engineered T-cells as described herewith and a pharmaceutically acceptable excipient.

A further particular aspect relates to a pharmaceutical composition comprising a population of T-cells comprising the genetically engineered T-cells as described herewith and a pharmaceutically acceptable excipient.

Another particular aspect concerns a pharmaceutical composition comprising genetically engineered T-cells expressing a CAR22 and a CAR20 at their cell surface and a pharmaceutical excipient, wherein said CAR22 comprises the VH of SEQ ID NO: 11 and the VL of SEQ ID NO: 12, and said CAR20 comprises the VH of SEQ ID NO: 15 and the VL of SEQ ID NO: 16.

Still more particularly, is provided a pharmaceutical composition comprising genetically engineered T-cells expressing a CAR22 and a CAR20 at their cell surface and a pharmaceutical excipient, wherein said CAR22 comprises the amino acid sequence of SEQ ID NO: 14, and wherein said CAR20 comprises the amino acid sequence of SEQ ID NO: 18.

A further particular aspect relates to a pharmaceutical composition comprising a population of T-cells comprising genetically engineered T-cells expressing a CAR22 and a CAR20 at their cell surface and a pharmaceutical excipient, wherein said CAR22 comprises the VH of SEQ ID NO: 11 and the VL of SEQ ID NO: 12, and said CAR20 comprises the VH of SEQ ID NO: 15 and the VL of SEQ ID NO: 16.

A further particular aspect relates to a pharmaceutical composition comprising a population of T-cells comprising genetically engineered T-cells expressing a CAR22 and a CAR20 at their cell surface and a pharmaceutical excipient, wherein said CAR22 comprises the amino acid sequence of SEQ ID NO: 14, and wherein said CAR20 comprises the amino acid sequence of SEQ ID NO: 18.

Another particular aspect concerns a pharmaceutical composition comprising genetically engineered T-cells expressing a CAR22 and a CAR20 at their cell surface and a pharmaceutical excipient, wherein said CAR22 comprises the VH of SEQ ID NO: 11 and the VL of SEQ ID NO: 12, and said CAR20 comprises the VH of SEQ ID NO: 15 and the VL of SEQ ID NO: 16, and wherein said T-cells have at least one allele encoding TCR alpha, TCR beta, and/or CD3 that has been inactivated by mutation, and/or wherein said engineered T-cells have at least one allele selected from β2m and CD52 that has been inactivated.

Still more particularly, is provided a pharmaceutical composition comprising genetically engineered T-cells expressing a CAR22 and a CAR20 at their cell surface and a pharmaceutical excipient, wherein said CAR22 comprises the amino acid sequence of SEQ ID NO: 14, wherein said CAR20 comprises the amino acid sequence of SEQ ID NO: 18, and wherein said T-cells have at least one allele encoding TCR alpha, TCR beta, and/or CD3 that has been inactivated by mutation.

Still more particularly, is provided a pharmaceutical composition comprising genetically engineered T-cells expressing a CAR22 and a CAR20 at their cell surface and a pharmaceutical excipient, wherein said CAR22 comprises the amino acid sequence of SEQ ID NO: 14, wherein said CAR20 comprises the amino acid sequence of SEQ ID NO: 18, and wherein said T-cells have at least one allele encoding TCR alpha, TCR beta, and/or CD3 that has been inactivated by mutation, and/or wherein said engineered T-cells have at least one allele selected from β2m and CD52 that has been inactivated.

A further particular aspect relates to a pharmaceutical composition comprising a population of T-cells comprising genetically engineered T-cells expressing a CAR22 and a CAR20 at their cell surface and a pharmaceutical excipient, wherein said CAR22 comprises the VH of SEQ ID NO: 11 and the VL of SEQ ID NO: 12, said CAR20 comprises the VH of SEQ ID NO: 15 and the VL of SEQ ID NO: 16, and wherein said T-cells have at least one allele encoding TCR alpha, TCR beta, and/or CD3 that has been inactivated by mutation, and/or wherein said engineered T-cells have at least one allele selected from β2m and CD52 that has been inactivated.

A further particular aspect relates to a pharmaceutical composition comprising a population of T-cells comprising genetically engineered T-cells expressing a CAR22 and a CAR20 at their cell surface and a pharmaceutical excipient, wherein said CAR22 comprises the amino acid sequence of SEQ ID NO: 14, wherein said CAR20 comprises the amino acid sequence of SEQ ID NO: 18, and wherein said T-cells have at least one allele encoding TCR alpha, TCR beta, and/or CD3 that has been inactivated by mutation.

A further particular aspect relates to a pharmaceutical composition comprising a population of T-cells comprising genetically engineered T-cells expressing a CAR22 and a CAR20 at their cell surface and a pharmaceutical excipient, wherein said CAR22 comprises the amino acid sequence of SEQ ID NO: 14, wherein said CAR20 comprises the amino acid sequence of SEQ ID NO: 18, and wherein said T-cells have at least one allele encoding TCR alpha, TCR beta, and/or CD3 that has been inactivated by mutation, and/or wherein said engineered T-cells have at least one allele selected from β2m and CD52 that has been inactivated.

Also provided herewith are genetically engineered immune cells expressing CAR20 and CAR22 as described herewith for use as a medicament.

Also provided herewith is a population of immune cells comprising the genetically engineered immune cells expressing CAR20 and CAR22 as described herewith for use as a medicament.

Methods of Treatment

Another aspect relates to methods of treatment of a cancer and/or an inflammatory disorder comprising administering, to a patient in need thereof, the genetically engineered immune cells expressing CAR20 and CAR22 as described herewith.

A similar aspect concerns the genetically engineered immune cells expressing CAR20 and CAR22 as described herewith, for use in a method of treatment of a cancer and/or inflammatory disorder.

A similar aspect concerns a population of immune cells comprising the genetically engineered immune cells expressing CAR20 and CAR22 as described herewith, for use in a method of treatment of a cancer and/or inflammatory disorder.

A similar aspect concerns the use of the genetically engineered immune cells expressing CAR20 and CAR22 as described herewith, or the population of immune cells comprising the genetically engineered immune cells expressing CAR20 and CAR22 as described herewith, for the preparation of a medicament.

A similar aspect concerns the use of the genetically engineered immune cells expressing CAR20 and CAR22 as described herewith, or the population of immune cells comprising the genetically engineered immune cells expressing CAR20 and CAR22 as described herewith, for the preparation of a medicament for treating a cancer and/or an inflammatory disorder.

The treatment may be for treating cancers including a hematological cancer such as a hematological cancer selected from (lymphoma, Hodgkin lymphoma (HL), non-Hodgkin lymphoma (NHL), leukemia, multiple myeloma (MM), B-chronic lymphocytic leukemia (B-CLL), hairy cell leukemia (HCL), acute lymphocytic leukemia (ALL) (also known as acute lymphoblastic leukemia), acute lymphocytic cancer, acute myeloid leukemia (AML), in particular a CD22- and/or CD20-associated hematological cancer, more particularly a relapse refractory CD22- and/or CD20-associated hematological cancer, even more particularly an aggressive form of said CD22- and/or CD20-associated hematological cancer.

The treatment may relate to the prevention or attenuation of an inflammatory disorder associated with CD20 and/or CD22.

In a particular aspect, the treatment is for treating patients with relapse refractory NHL.

In a further particular aspect, the treatment is for treating patients suffering from cancers where the expression of CD20 and CD22 antigens is low.

In a particular aspect, the treatment is for treating patients having been previously treated with Rituximab (anti-CD20 antibody that is a standard of care in the treatment of NHL).

"Non-Hodgkin lymphoma (NHL)" is the term for a diverse group of blood cancers that share a single characteristic: they all arise from lymphocytes. More than 60 specific NHL subtypes have been identified and assigned names, called "diagnostic designations," by the World Health Organization (WHO).

In particular, the term "Non-Hodgkin Lymphoma (NHL)" includes the following diagnostic designations for Non-Hodgkin Lymphoma (NHL):

1. Mature B-cell lymphomas (about 85%-90% of NHL cases):

Aggressive: Diffuse large B-cell lymphoma (DLBCL) (31%), Mantle cell lymphoma (MCL) (can present as aggressive or indolent) (6%), Lymphoblastic lymphoma (2%), Burkitt lymphoma (BL) (2%), Primary mediastinal (thymic) large B-cell lymphoma (PMBCL) (2%), Transformed follicular and transformed mucosa-associated lymphoid tissue (MALT) lymphomas, High-grade B-cell lymphoma with double or triple hits (HBL), Primary cutaneous DLBCL (leg type), Primary DLBCL of the central nervous system, Primary central nervous system (CNS) lymphoma, Acquired immunodeficiency syndrome (AIDS)-associated lymphoma Indolent: Follicular lymphoma (FL) (22%), Marginal zone lymphoma (MZL) (8%), Chronic lymphocytic leukemia/small-cell lymphocytic lymphoma (CLL/SLL) (6%), Gastric mucosa-associated lymphoid tissue (MALT) lymphoma (5%), Lymphoplasmacytic lymphoma (1%), Waldenström macroglobulinemia (WM), Nodal marginal zone lymphoma (NMZL) (1%), Splenic marginal zone lymphoma (SMZL), 2. Mature T-cell and natural killer (NK)-cell lymphomas (about 10%-15% of NHL cases)

Aggressive: Peripheral T-cell lymphoma (PTCL), not otherwise specified (6%), Systemic anaplastic large-cell lymphoma (ALCL) (2%), Lymphoblastic lymphoma (2%), Hepatosplenic gamma/delta T-cell lymphoma, Subcutaneous panniculitis-like T-cell lymphoma (SPTCL), Enteropathy-type intestinal T-cell lymphoma, Primary cutaneous anaplastic large-cell lymphoma Indolent: Cutaneous T-cell lymphoma (CTCL) (4%), Mycosis fungoides (MF), Sézary syndrome (SS), Angioimmunoblastic T-cell lymphoma (AITL), Adult T-cell leukemia/lymphoma, Extranodal NK/T-cell lymphoma (ENK/TCL), nasal type.

The above written description of the invention provides a manner and process of making and using it such that any person skilled in this art is enabled to make and use the same, this enablement being provided in particular for the subject matter of the appended claims, which make up a part of the original description.

Where a numerical limit or range is stated herein, the endpoints are included. Also, all values and subranges within a numerical limit or range are specifically included as if explicitly written out.

Having generally described this invention, a further understanding can be obtained by reference to certain specific examples, which are provided herein for purposes of illustration only, and are not intended to limit the scope of the claimed invention.

PARTICULAR EMBODIMENTS

1. A genetically engineered T-cell expressing a Chimeric Antigen Receptor (CAR) specific for CD22 (CAR22) and a Chimeric Antigen Receptor specific for CD20 (CAR20) at its cell surface,
    a) wherein said CAR22 comprises:
        i) at least one extracellular domain comprising:
            an antigen binding domain specific for CD22 comprising the Variable Heavy chain (VH) of SEQ ID NO: 11 and the Variable Light chain (VL) of SEQ ID NO: 12, optionally a leader sequence,
            a hinge domain from CD8alpha,
        ii) a transmembrane domain from CD8alpha, and
        iii an intracellular domain comprising a 4-1BB stimulatory domain and a CD3zeta signalling domain; and
    b) wherein said CAR20 comprises:
        i) at least one extracellular domain comprising:
            an antigen binding domain specific for CD20 comprising the Variable Heavy chain (VH) of SEQ ID NO: 15 and the Variable Light chain (VL) of SEQ ID NO: 16, optionally a leader sequence,
            a hinge domain from CD8alpha,
        ii) a transmembrane domain from CD8alpha, and
        iii) an intracellular domain comprising a 4-1BB stimulatory domain and a CD3zeta signalling domain; and
    c) wherein said engineered T-cell is TCR negative.

2. The genetically engineered T-cell according to embodiment 1, wherein said CAR22 comprises the amino acid sequence of SEQ ID NO: 14, and wherein said CAR20 comprises the amino acid sequence of SEQ ID NO: 18.

3. The genetically engineered T-cell according to any one of embodiments 1 to 2, wherein none of the extracellular domain of said CAR20 and CAR22 comprises a rituximab-specific mimotope of SEQ ID NO: 22.

4. The genetically engineered T-cell of any one of embodiments 1 to 3, wherein said engineered T-cell expresses a short hairpin RNA (shRNA) or small interfering (siRNA) directed against a polynucleotide sequence encoding a component of TCR.

5. The genetically engineered T-cell of any one of embodiments 1 to 3, wherein said engineered T-cell is mutated in its TCR alpha and/or TCR beta alleles.

6. The genetically engineered T-cell according to any one of embodiments 1 to 3, and 5, wherein said engineered T-cell has at least one allele encoding TCR alpha, TCR beta, and/or CD3 that has been inactivated by mutation.

7. The genetically engineered T-cell according to any one of embodiments 1 to 6, wherein said engineered T-cell has a CD52 allele that has been inactivated.

8. The genetically engineered T-cell according to any one of embodiments 1 to 7, wherein said engineered T-cell has a β2m allele that has been inactivated.

9. The genetically engineered T-cell according to any one of embodiments 1 to 8, wherein said engineered T-cell has a PD1 allele that has been inactivated.

10. The genetically engineered T-cell according to any one of embodiments 1 to 9, wherein said engineered T-cell has a CTLA4 allele that has been inactivated.

11. The genetically engineered T-cell according to any one of embodiments 1 to 10, wherein said engineered T-cell has a dCK allele that has been inactivated.

12. The genetically engineered T-cell according to any one of embodiments 1 to 11, wherein said engineered T-cell has a GR allele that has been inactivated.

13. The genetically engineered T-cell according to any one of embodiments 1 to 12, wherein said engineered immune cell is a cytotoxic T cell.

14. The genetically engineered T-cell according to any one of embodiments 1 to 13, wherein said engineered T-cell is comprised in a population of T-cells.

15. The genetically engineered T-cell according to any one of embodiments 1 to 14, wherein said engineered T-cell is a primary cell.

16. The genetically engineered T-cell according to any one of embodiments 1 to 15, wherein said T-cell is a mammalian cell, preferably a human cell.

17. The genetically engineered T-cell according to to any one of embodiments 1 to 16, wherein said engineered T-cell expresses no further CAR than said CAR22 and CAR20.

18. A population of T-cells comprising the engineered T-cells according to any one of embodiments 1 to 17.

19. A pharmaceutical composition comprising the engineered T-cells according to any one of embodiments 1 to 17, and a pharmaceutically acceptable excipient.

20. A pharmaceutical composition comprising a population of T-cells according to embodiment 18, and a pharmaceutically acceptable excipient.

21. An isolated polynucleotide comprising:
    a) a nucleic acid encoding a CAR22 comprising:
        i) at least one extracellular domain comprising:
            an antigen binding domain specific for CD22 comprising the Variable Heavy chain (VH) of SEQ ID NO: 11 and the Variable Light chain (VL) of SEQ ID NO: 12, optionally a leader sequence,
            a hinge domain from CD8alpha,
        ii) a transmembrane domain from CD8alpha, and
        iii) an intracellular domain comprising a 4-1BB stimulatory domain and a CD3zeta signalling domain; and
    b) a nucleic acid encoding a CAR20 comprising:
        i) at least one extracellular domain comprising:
            an antigen binding domain specific for CD20 comprising the Variable Heavy chain (VH) of SEQ ID NO: 15 and the Variable Light chain (VL) of SEQ ID NO: 16, optionally a leader sequence,
            a hinge domain from CD8alpha,
        ii) a transmembrane domain from CD8alpha, and
        iii) an intracellular domain comprising a 4-1BB stimulatory domain and a CD3zeta signalling domain.

22. The polynucleotide of embodiment 21, wherein the nucleic acids of a) and b) are on a single nucleic acid molecule and wherein a nucleic acid sequence encoding a self-cleaving peptide (such as P2A, T2A, E2A, or F2A) is located between the nucleic acids of a) and b).

23. The polynucleotide of embodiment 21 or 22, wherein said isolated polynucleotide does not comprise a nucleic acid encoding a further CAR than said CAR22 and CAR20.

24. The polynucleotide of embodiment 21 to 23, wherein said isolated polynucleotide does not comprise a nucleic acid encoding rituximab-specific mimotope of SEQ ID NO: 22.

25. The polynucleotide of any one of embodiments 21 to 24, wherein the nucleic acid of a) comprises a promoter (such as the EF1alpha promoter) that controls the expression of said CAR22 composed of the signal peptide of SEQ ID NO: 1, the scFv of SEQ ID NO: 13, the CD8alpha hinge of SEQ ID NO: 4, the CD8alpha transmembrane domain of SEQ ID NO: 6, the 4-1BB co-stimulation domain of SEQ ID NO: 8, and the CD3 zeta signalisation domain of SEQ ID NO: 9;

wherein the nucleic acid of b) encodes for said CAR20 composed of the signal peptide of SEQ ID NO: 1, the scFv of SEQ ID NO: 17, the CD8alpha hinge of SEQ ID NO: 4, the CD8alpha transmembrane domain of SEQ ID NO: 6, the 4-1BB co-stimulation domain of SEQ ID NO: 8, and the CD3 zeta signalisation domain of SEQ ID NO: 9; and wherein a nucleic acid encoding for a self-cleaving peptide (such as P2A of SEQ ID NO: 19) is present between the nucleic acid of a) and the nucleic acid of b), allowing the simultaneous expression of said CAR20 and CAR22.

26. The polynucleotide of any one of embodiments 21 to 24, wherein the nucleic acid of b) comprises a promoter (such as the EF1alpha promoter) that controls the expression of said CAR20 composed of the signal peptide of SEQ ID NO: 1, the scFv of SEQ ID NO: 17, the CD8alpha hinge of SEQ ID NO: 4, the CD8alpha transmembrane domain of SEQ ID NO: 6, the 4-1BB co-stimulation domain of SEQ ID NO: 8, and the CD3 zeta signalisation domain of SEQ ID NO: 9;

wherein the nucleic acid of a) encodes for said CAR22 composed of the signal peptide of SEQ ID NO: 1, the scFv of SEQ ID NO: 13, the CD8alpha hinge of SEQ ID NO: 4, the CD8alpha transmembrane domain of SEQ ID NO: 6, the 4-1BB co-stimulation domain of SEQ ID NO: 8, and the CD3 zeta signalisation domain of SEQ ID NO: 9; and wherein a nucleic acid encoding for a self-cleaving peptide (such as P2A of SEQ ID NO: 19) is present between the nucleic acid of a) and the nucleic acid of b), allowing the simultaneous expression of said CAR22 and CAR20.

27. The isolated polynucleotide of embodiment 25 comprising the nucleic acid sequence of SEQ ID NO: 31 (CAR22×CAR20 construct).

28. The isolated polynucleotide of embodiment 26 comprising the nucleic acid sequence of SEQ ID NO: 32 (CAR20×CAR22 construct).

29. A vector comprising the isolated polynucleotide of any one of embodiments 21 to 28.

30. A host cell comprising the vector of embodiment 29.

31. A method of preparing the engineered T-cells according to any one of embodiments 1 to 17, comprising introducing into an immune cell the polynucleotide according to any one of embodiments 21 to 28, or a vector according to embodiment 29.

32. The engineered T-cells according to any one of embodiments 1 to 17, for use as a medicament.

33. The engineered T-cells according to any one of embodiments 1 to 17, for use in the treatment of a cancer associated with CD20 and/or CD22 expression.

34. The engineered T-cells according to any one of embodiments 1 to 17, for use in the treatment of a hematological cancer, in particular a CD22- and/or CD20-associated hematological cancer, more particularly a relapse refractory CD22- and/or CD20-associated hematological cancer, even more particularly an aggressive form of said CD22- and/or CD20-associated hematological cancer.

35. The engineered T-cells for use according to embodiment 33 or 34, wherein said cancer is selected from the group consisting of lymphoma, Hodgkin lymphoma (HL), non-Hodgkin lymphoma (NHL), leukemia, multiple myeloma (MM), B-chronic lymphocytic leukemia (B-CLL), hairy cell leukemia (HCL), acute lymphocytic leukemia (ALL), acute lymphocytic cancer, acute myeloid leukemia (AML).

36. The engineered T-cells for use according to embodiment 35, wherein said cancer is non-Hodgkin lymphoma or acute lymphocytic leukemia.

37. The engineered T-cells for use according to any one of embodiments 33 to 36, wherein said cancer is associated with a low expression of CD20 and/or CD22.

38. The engineered T-cells for use according to any one of embodiments 33 to 37, wherein said cancer is a relapsing non-Hodgkin lymphoma.

39. A method of treating a patient suffering from a cancer associated with CD20 and/or CD22 expression, comprising administering to said patient an effective amount of an engineered T-cells according to any one of embodiments 1 to 17, or a population of T-cells according to embodiment 18.

40. The method of treatment according to embodiment 39, wherein said cancer is selected from the group consisting of lymphoma, Hodgkin lymphoma (HL), non-Hodgkin lymphoma (NHL), leukemia, multiple myeloma (MM), B-chronic lymphocytic leukemia (B-CLL), hairy cell leukemia (HCL), acute lymphocytic leukemia (ALL), acute lymphocytic cancer, acute myeloid leukemia (AML).

41. The method of treatment according to embodiment 39 or 40, wherein said cancer is non-Hodgkin lymphoma or acute lymphocytic leukemia.

42. The method of treatment according to any one of embodiments 39 to 41, wherein said cancer is associated with a low expression of CD20 and/or CD22.

43. The method of treatment according to any one of embodiments 39 to 42, wherein said cancer is a relapsing non-Hodgkin lymphoma.

EXAMPLES

The examples provided herewith describe how to generate dual CAR-T cells targeting CD20 and CD22 antigens ("CD20×CD22" or "CD20×CD22" CAR-T cells) and demonstrate their ability to lyse CD22 and/or CD20 low- or not-expressing tumor cells.

Example 1. Generation of the Dual CD20 and CD22 CAR Constructs and their Control Two orientations of the dual CAR were designed and constructed into recombinant lentiviral vector in order to be compared for expression, activity and efficiency. The first construct (CD22×CD20) contains the EF1alpha promoter that drives the expression of a first CD22 CAR composed of a signal peptide (SEQ ID NO: 1), the scFv of SEQ ID NO: 13, CD8alpha hinge (SEQ ID NO: 4) and TM domain (SEQ ID NO: 6), 4-1BB co-stimulation domain (SEQ ID NO: 8) and the CD3 zeta signalisation domain (SEQ ID NO: 9). This first CAR is followed by a self-cleaving peptide P2A (SEQ ID NO: 19) allowing the expression of the second CD20 CAR composed of signal peptide (SEQ ID NO:1), the anti-CD20 scFv of SEQ ID NO: 17, CD8alpha hinge (SEQ ID NO: 4) and TM domain (SEQ ID NO: 6), 4-1BB co-stimulation domain (SEQ ID NO: 8), and the CD3 zeta signalisation domain (SEQ ID NO: 9). In order to avoid any recombination event within the rLV construct, the nucleotide acid sequences used to code for the same amino acid sequences present twice in the construct were optimized using codon usage and code degeneracy so that the nucleotide sequences diverge. The second dual construct (CD20×CD22) contains exactly the same sequences (nucleotide acid and amino acid) but the CD20 CAR is located right after the EF1alpha promoter.

For comparison CD22 or CD20 CARs were constructed into recombinant lentiviral vector. Those constructs contain EF1alpha promoter driving the expression of the single CAR targeting CD22 (SEQ ID NO: 14) or CD20 (SEQ ID NO: 18).

Example 2: Generation of CD20×CD22 or CD22×CD20 Dual CAR-T Cells

Cryopreserved PBMC from at least 3 different donors were used. PBMCs were thawed at 37° C., washed and re-suspended in OpTmizer medium supplemented with AB human serum (5%) recombinant human interleukin-2 (rhIL-2, 350 IU/ml) for an overnight incubation at 37° C. in 5% $CO_2$ incubator. Then, the cells were activated with anti-CD3/CD28 coated beads in OpTmizer medium supplemented with AB human serum (5%) (and additional 5% CTS™ Immune Cell SR during the expansion phase) and recombinant human interleukin-2 (rhIL-2, 350 IU/ml) in a $CO_2$ incubator for 3 days. The amplified T-cells were then transduced with lentiviral particles expressing CD20×CD22 or CD22×CD20 CARs (SEQ ID NO: 31 and SEQ ID NO: 32, respectively) at MOI 15 (MOI stands for Multiplicity of Infection) in the presence of Lentiboost (Mayflower bioscience SB-P-LV-101-12). The amplified T-cells were also transduced with lentiviral particles expressing either CD20 CAR or CD22 CAR alone (SEQ ID NO: 14 and SEQ ID NO: 18) at MOI 5. Two days post transduction cells were electroporated with 4 mRNAs, two encoding of TRAC_T01 TALEN arms (SEQ ID NO: 23 and SEQ ID NO: 24) and two encoding CD52_T01 TALEN arms (SEQ ID NO: 25 and SEQ ID NO: 26) using AgilePulse Max system. Cells were resuspended in culture medium incubated 16 to 18 h at 30° C. and expanded at 37° C. after addition of fresh culture medium and adjusting cell concentration from time to time. On the final day of culture (18 days post thawing), T cells were used in different assays or frozen in freezing medium (FBS 90%, DMSO 10%). Cells were kept frozen at −150° C. until use.

Example 3. CD20 and CD22 Dual CAR-T Cells Detection

In order to detect the CD20 CAR, a recombinant protein CD20 fused to a His tag (Acro #CD0-H52H3, SEQ ID NO: 20) was used coupled to APC labelled anti-His antibody (BioLegend #362605). For the CD22 CAR detection, a CD22-Fc protein (SEQ ID NO: 21) was used coupled with an anti-Fcgamma sub class 1 tag Cy3 (Jackson ImmunoResearch #115-165-205).

The different CAR T cells (untransduced, CD20×CD22 CAR, CD22×CD20 CAR or CD22 CAR) produced in example 1 were incubated with 100 ng of CD22-Fc protein and 200 ng of CD20-His protein, washed and further incubated with anti-Fc gamma (50 ng) or anti-His (50 ng) then fixed in PFA 2%. Cells were then analysed by flow cytometry.

The results in FIG. 1 demonstrate that transduction with CD22 CAR alone led to 40% of CD22 CAR positive T cells whereas transduction with CD22×CD20 or CD20×CD22 CAR led to 39% and 25% of double CAR positive T cells, respectively. These results were reproduced using three different donors. Interestingly CD22×CD20 led to a higher MFI of the CD22 CAR staining whereas CD20×CD22 led to a higher MFI of the CD20 CAR staining.

Example 4. Cell Lines Used for Testing CD20 and CD22 Dual CAR-T Cells

Figure 2:
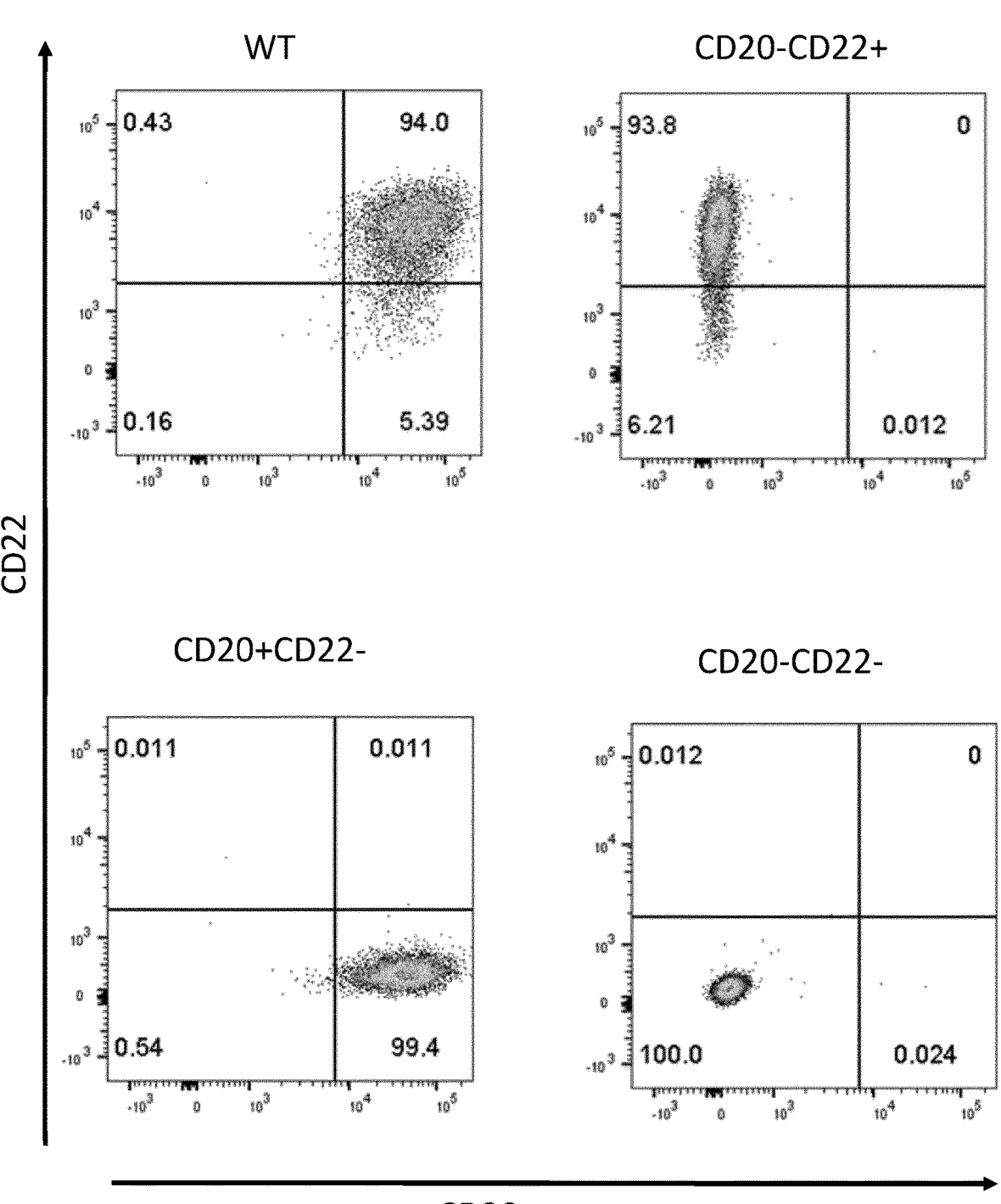
FIG. 2: Flow cytometry analysis of the different Raji cells obtained after CD20 and CD22 TALEN® treatment and cell sorting.

The Raji cell line expresses high level of CD20 and CD22. This cell line was modified to express Luciferase gene and was used as a positive control i.e. for target cells expressing both CD20 and CD22. In addition, Raji cell lines were treated with CD22 and/or CD20 TALEN. Briefly, Raji cells were electroporated with mRNAs encoding CD22 TALEN arms (SEQ ID NO: 27 and SEQ ID NO: 28) and mRNAs encoding CD20 TALEN (SEQ ID NO: 29 and SEQ ID NO: 30) using AgilePulse Max system. Cells were incubated at 30° C. for 16 to 18 hours in RPMI1640 10% Foetal Bovine Serum (FBS) and 1% Penicillin/Streptavidin (culture medium), and were grown in fresh culture medium at 37° C. in % CO2 incubator until sorting. Different cell populations were purified using anti-biotin microbeads and either anti-CD20-biotin, anti-CD22 biotin or both (Biolegend) to obtain distinct cell populations expressing i) CD20 but not CD22, ii) CD22 but not CD20, or iii) not expressing neither CD20 nor CD22. FIG. 2 illustrates the phenotype of these selected populations.

Example 5. Cytotoxicity of CD20 and CD22 Dual CAR T Cells

CD20×CD22, CD22×CD20 and CD22 CAR T cells as produced in example 1 and coming from three different donors were tested for their cytotoxicity capacity against the different Raji cells generated in example 4.

Figure 3:
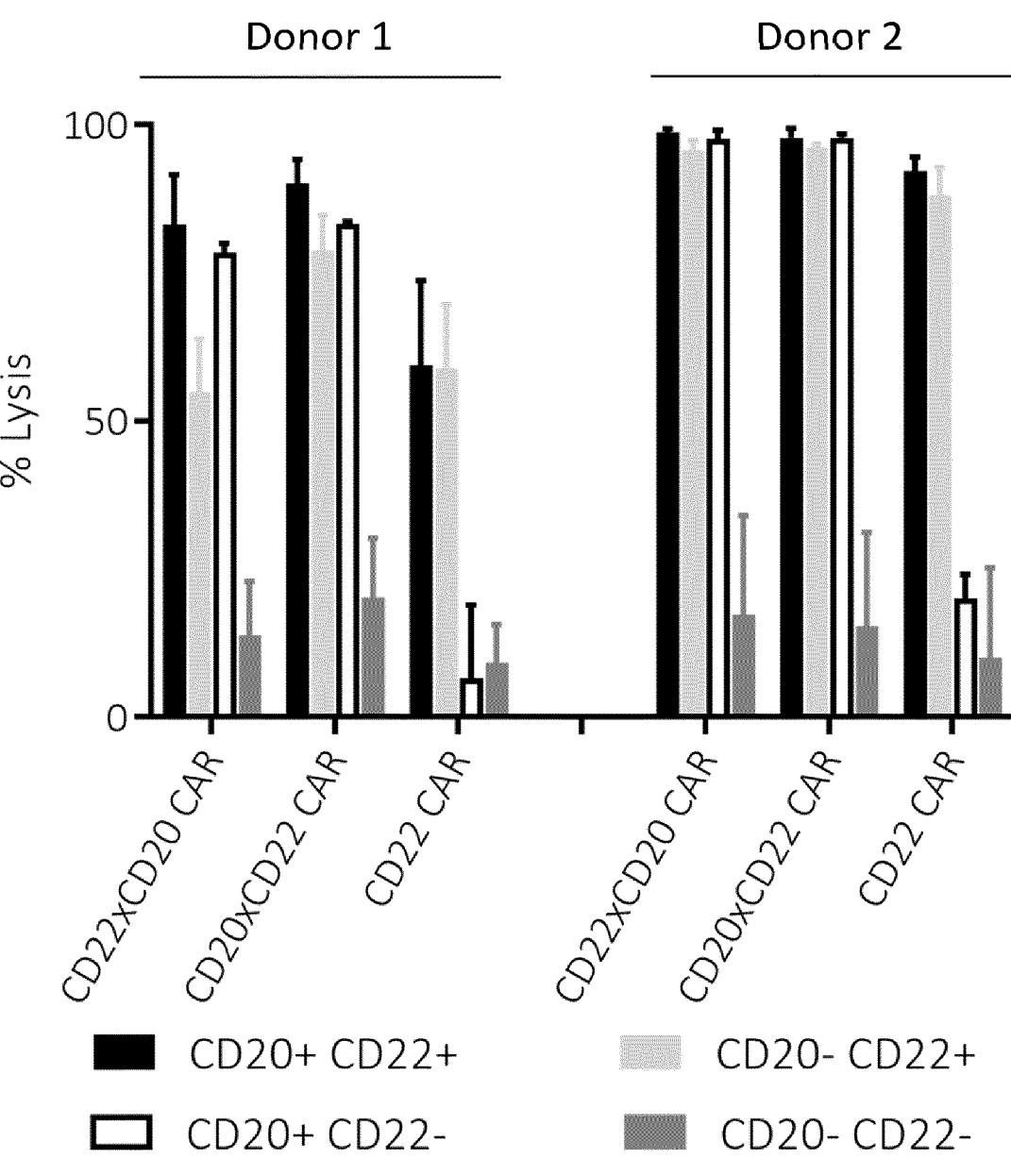
FIG. 3: Percentage of lysis of CD20×CD22, CD22×CD20 and CD22 CAR T cells from 2 different donors against Raji cells expressing, or not, CD20 and/or CD22 antigens.

The T cells were thawed and viable cells were counted using NucleoCounter® device (Chemometec NC-250). The different CAR T cells were co-cultured for 4 to 16 hours (at 37° C. in a 5% $CO_2$ incubator) with the different Raji cells (CD20+CD22+, CD20+CD22−, CD22−CD20+ and CD20−CD22−) expressing luciferase in 96 well plates at different Effector/Target ratio. At the end of the incubation period, the released luciferase was measured using One-Glo® kit (Promega #E6110) according to provider's protocol. FIG. 3 shows that for all donors used, CD22 CAR T cells could efficiently lyse CD20+CD22+ and CD20-CD22+ Raji clones while CD22×CD20 or CD20×CD22 CAR T cells add the same level of lysis than CD22 CAR but could also lyse to the same level CD20+CD22− Raji clones.

The killing ability of CD20×CD22, CD22×CD20 and CD22 CAR T cells as produced in example 1 was also tested in a rechallenge or serial killing assay. The different CAR T cells were thawed, counted and incubated with the different Raji cells at a 1:1 ratio of CAR positive T cells/Raji cells (CD20+CD22+, CD20-CD22+, CD20+CD22−). After 3 days of incubation, half of the wells were used to measure the release luciferase using One-Glo® kit (Promega #E6110), while the other half is transferred to new plates containing Raji cells for an additional incubation. Luciferase measurement was repeated at 7 days, 10 days, 14 days and 17 days.

Figure 4:
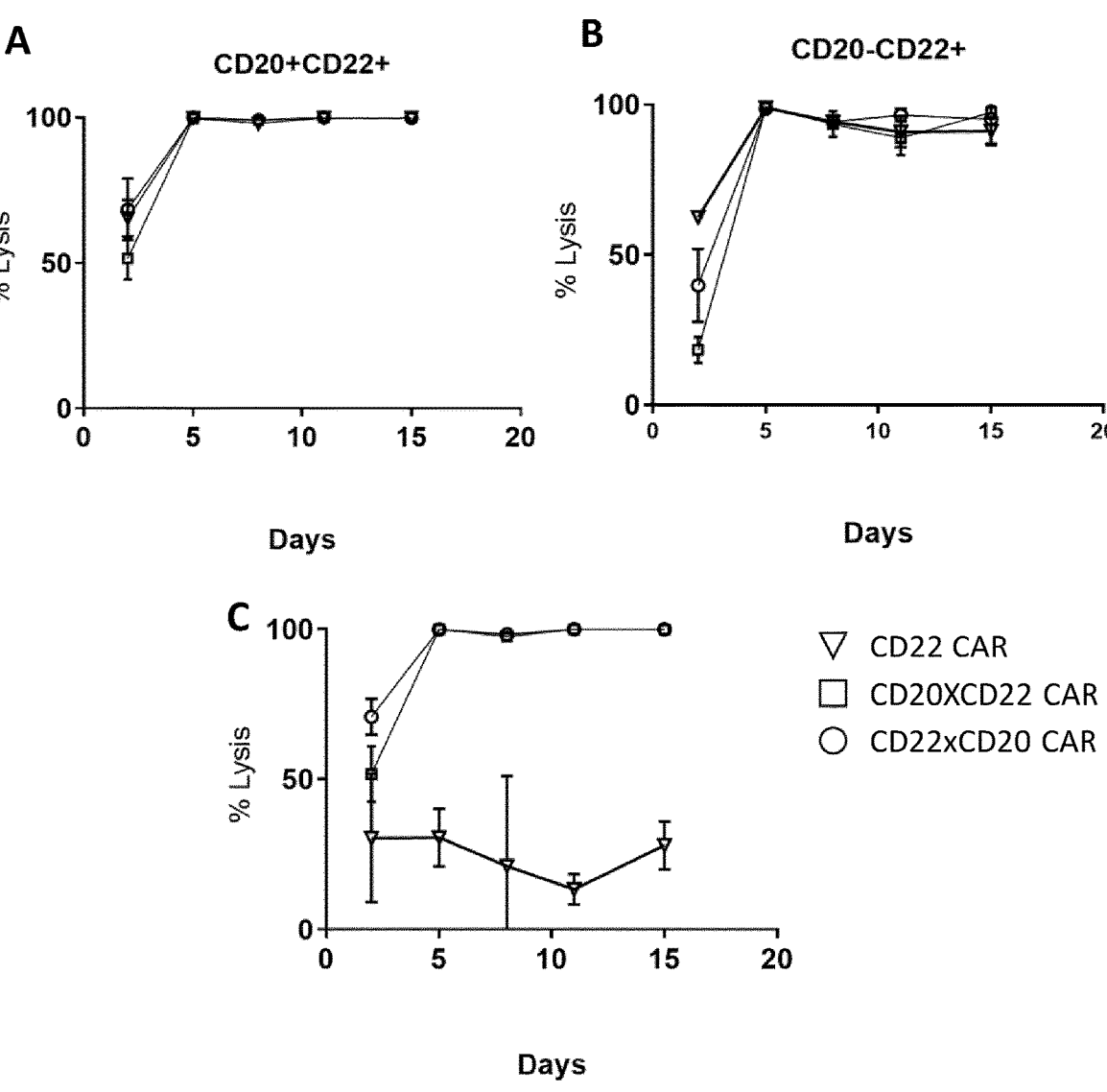
FIG. 4: Percentage of lysis, over time, of CD20×CD22, CD22×CD20 and CD22 CAR T cells against Raji cells either expressing CD20 and CD22 (A), expressing CD22 only (B), or expressing CD20 only (C).

FIG. 4 shows that CD22×CD20 or CD20×CD22 CAR Tcells were able to kill efficiently all Raji cells tested whereas CD22 CAR T cells were able to kill efficiently only CD20+CD22+ and CD20-CD22+ Raji cells. Surprisingly, CD22 CAR T had a low activity on CD20+CD22-Raji cells suggesting that CD22 expression was not totally abolished in this clone. This also suggests that dual CARs could efficiently kill targeted tumor cells that have low expression of both targeted antigens.

TABLE 7

List of TALENs used

| Target | Target sequence | TALE-nuclease arms |
|--------|-----------------|--------------------|
| TRAC_T01 | TTGTCCCACAGATATCC agaaccctgaccctg CCGTGTACCAGCTGAGA (SEQ ID NO: 29) | TRAC_T01-L TALEN (SEQ ID NO: 23) TRAC_T01-R TALEN (SEQ ID NO: 24) |
| CD52_T01 | TTCCTCCTACTCACCAT cagcctcctggttat GGTACAGGTAAGAGCAA (SEQ ID NO: 30) | CD52_T01-L TALEN (SEQ ID NO: 25) CD52_T01-R TALEN (SEQ ID NO: 26) |
| CD22_T01 | TCTGGTTTTCTTCCAGA tcctcccaagaaggt GACCACAGTGATTCAAA (SEQ ID NO: 35) | CD22_T01-L TALEN (SEQ ID NO: 27) CD22_T01-R TALEN (SEQ ID NO: 28) |
| CD20_T01 | TTTGCTGCCATTTCTGG aatgattctttcaat CATGGACATACTTAATA (SEQ ID NO: 36) | CD20_T01-L TALEN (SEQ ID NO: 29) CD20_T01-R TALEN (SEQ ID NO: 30) |

Figure 5:
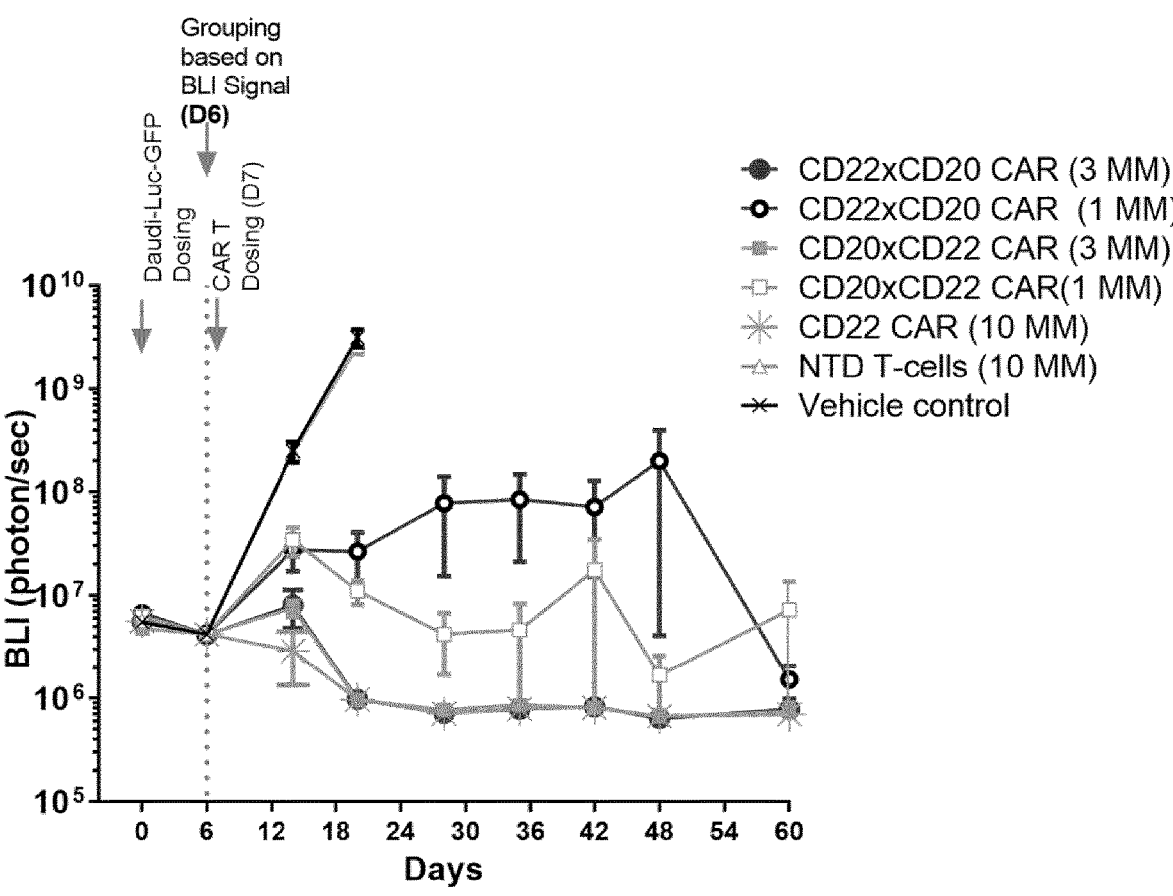
FIG. 5: Dose dependent control of in vivo tumor burden upon treatment with indicated dose of CD20×CD22, CD22×CD20 and CD22 CAR T cells measured by bioluminescence.

Example 6. Tumor Burden Control of a Disseminated In Vivo Model of B-Cell Lymphoma Daudi cells expressing CD20 and CD22 were modified to express luciferase and GFP. Daudi cells were intravenously injected in NSG immunodeficient mice (NOD.Cg-Prkdcscid II2rgtm1WjI/SzJ, Jackson laboratories). Seven days after tumor implantation, CD20×CD22 (1 and 3 millions), CD22×CD20 (1 and 3 millions) and CD22 (10 millions) CAR T-cells were intravenously injected in individual mice. Bioluminiscence signal (BLI) upon injection of D-luciferin was monitored bi-weekly until day 60 after CAR T-cell injection and values are represented in FIG. 5. For all conditions of treatment with CART-cells tested, BLI signal was reduced compared to vehicle control or non-transduced T cells. Surprisingly, at a low dose of 1 million CAR+ T-cells, CD20×CD22 CAR T-cells had a strong killing activity that was higher than that of CD22×CD20 CAR T-cells.

Figure 6:
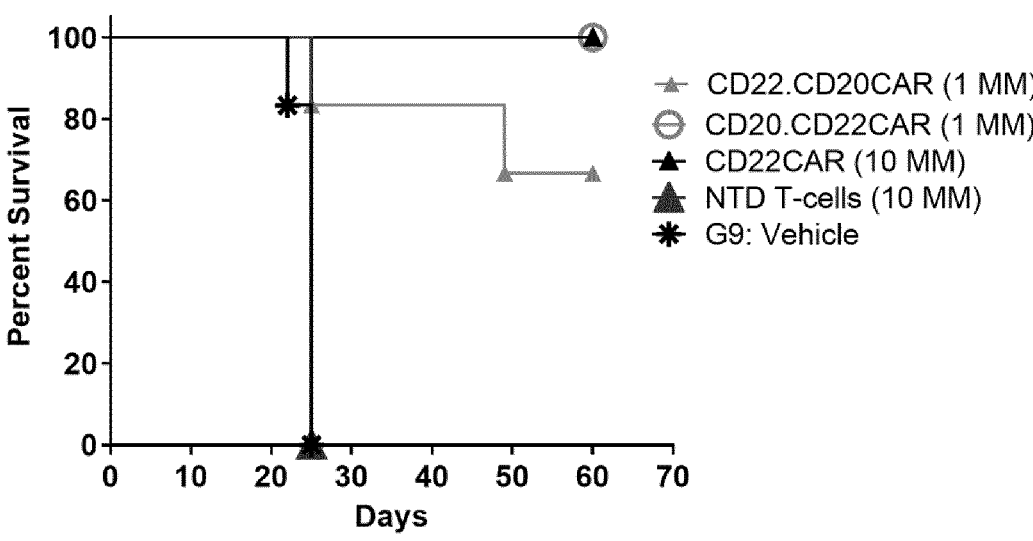
FIG. 6: Survival curve for animals treated with the indicated dose of CD20×CD22, CD22×CD20 and CD22 CAR T-cells in a disseminated model of B-cell lymphoma.

Example 7. Treatment Efficacy in a Disseminated In Vivo Model of B-Cell Lymphoma Animals injected with Daudi cells and subsequently intravenously injected with CD20×CD22 (1 million), CD22×CD20 (1 million) and CD22 (10 millions) CAR T-cells from Example 6 were monitored for survival during 60 days. As FIG. 6 shows, animals treated with any of the CART-cells tested survived longer than animals treated with either vehicle or non-transduced T cells (NTD). In addition, and surprisingly, animals treated with CD20×CD22 CAR T-cells survived longer than animals treated with CD22×CD20 CAR T-cells.

Figure 7:
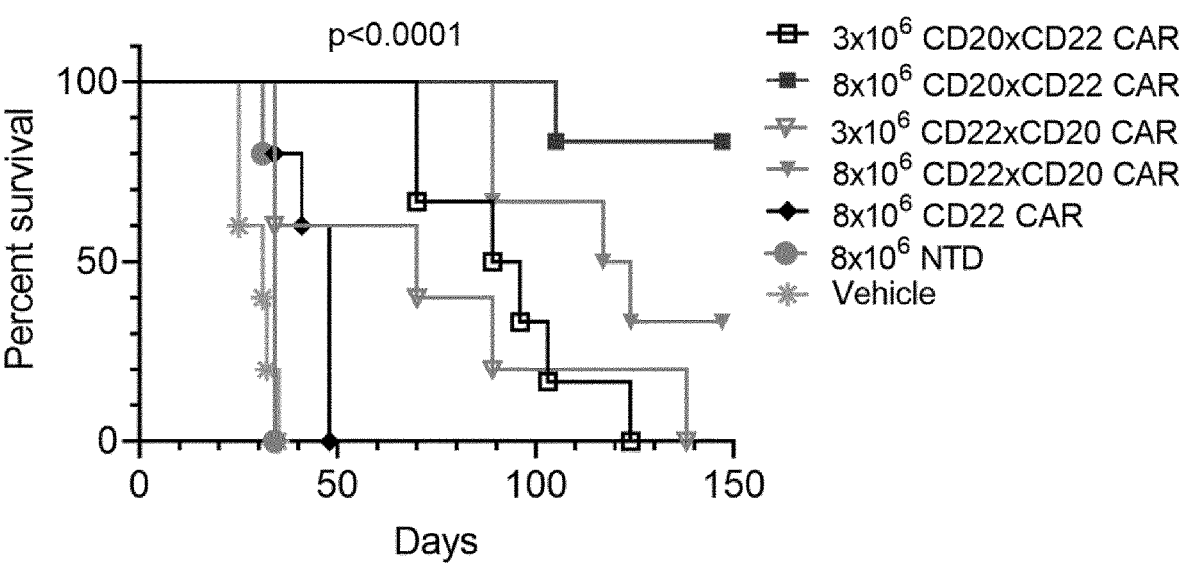
FIG. 7: Survival curve of animals treated with the indicated doses of CD20×CD22, CD22×CD20 and CD22 CAR T-cells in a subcutaneous model of B-cell lymphoma.

Example 8. Treatment Efficacy in a Disseminated In Vivo Model of B-Cell Lymphoma Raji cell lines described in Example 2 were injected subcutaneously in NSG immunodeficient mice (NOD.Cg-Prkdcscid II2rgtm1WjI/SzJ, Jackson laboratories). All three cell lines were injected simultaneously in each individual animal, specifically, Raji WT cells were injected in one flank, Raji CD22—cells were injected in another flank and CD20—cells in a third flank. One week after tumor injection, CD20×CD22 (3 and 8 millions), CD22×CD20 (3 and 8 millions) and CD22 (8 millions) CAR T-cells were injected intravenously and animals were monitored for survival. As depicted in FIG. 7, animals treated with CD22 CAR T-cells succumbed fast to the disease since they carried CD22—tumor cells, which can not be targeted by CD22 CAR T-cells. Treatment with three and eight millions of dual CAR T-cells shows that while both treatments are efficient, CD20×CD22 treated animals surprisingly survived for a longer time than animals treated with CD22×CD20.

Example 9. IFN Gamma Release of CD20 and CD22 Dual CAR T Cells

Figure 8:
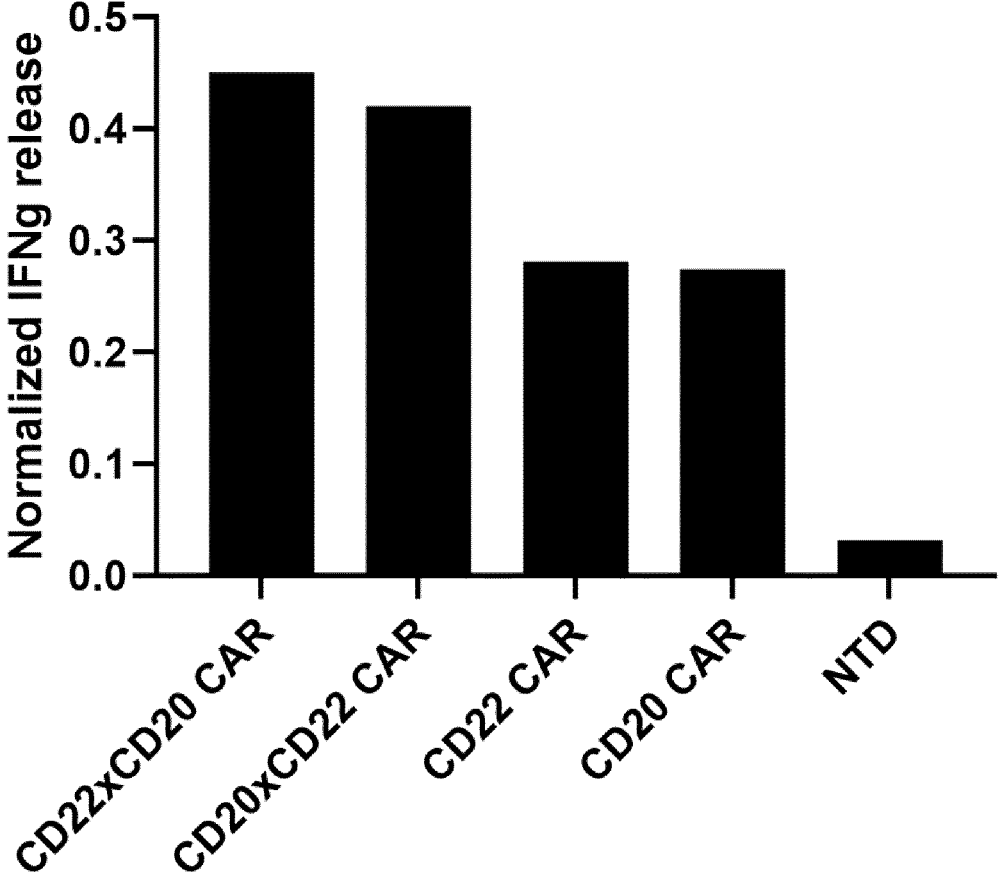
FIG. 8. Release of IFN gamma by CD20×CD22, CD22×CD20, CD20 and CD22 CAR T cells on Daudi cells.

Daudi cells expressing CD20 and CD22 were modified to express luciferase gene and GFP. Those Daudi cells were incubated overnight with CD20×CD22, CD22×CD20, CD22 or CD20 positive CAR T-cells at a ratio of 1:1 (effector-target). Next day, plate was centrifuged, and supernatant was collected. Levels of IFN gamma released upon incubation of tumor with CAR T-cells were quantified using the Human IFN-gamma Quantikine ELISA kit (R&D systems, DIF50C) following manufacturer's instructions. As positive control CAR-T-cells were incubated with phorbol myristate acetate (PMA, Sigma Aldrich P8139) and lonomycin (Sigma aldrich I0634). Final values of IFN gamma release were normalized to those of the positive control. FIG. 8 shows that dual CD20×CD22 CAR-T cells as well as CD22×CD20 CAR T cells were activated upon antigen recognition on tumor cells and released higher levels of IFN-gamma than the single CAR (CD20 or CD22) T cells. This observation points towards a synergistic benefit of using the dual CD20, CD22 CAR T cells.

The invention claimed is:

1. A genetically engineered immune cell expressing a Chimeric Antigen Receptor (CAR) specific for CD22 (CAR22) and a Chimeric Antigen Receptor specific for CD20 (CAR20) at its cell surface, wherein said CAR22 and said CAR20 are encoded by an exogenous nucleic acid incorporated in the genome of said immune cell, and wherein said exogenous nucleic acid comprises, from 5' to 3':

i) a promoter, ii) a nucleic acid encoding said CAR20, iii) a nucleic acid encoding a self-cleaving peptide, and iv) a nucleic acid encoding said CAR22, whereby the same promoter controls the expression of said CAR20 and said CAR22, and wherein said exogenous nucleic acid comprises the nucleotide sequence of SEQ ID NO: 32.

2. The genetically engineered immune cell of claim 1, wherein said CAR22 comprises the amino acid sequence of SEQ ID NO: 14, and wherein said CAR20 comprises the amino acid sequence of SEQ ID NO: 18, wherein the leader amino acid sequence set forth in SEQ ID NO: 1 is removed when said CAR20 and said CAR22 are at the cell surface.

3. The genetically engineered immune cell of claim 1, wherein said engineered immune cell is selected from the group consisting of a T-cell, a NK-cell, and a macrophage.

4. The genetically engineered immune cell of claim 1, wherein said engineered immune cell is a T-cell.

5. The genetically engineered immune cell of claim 4, wherein said engineered immune cell is a T-cell that is TCR negative.

6. The genetically engineered immune cell of claim 4, wherein said engineered T-cell has at least one allele encoding TCR alpha, TCR beta, and/or CD3 that has been inactivated by mutation.

7. The genetically engineered immune cell of claim 4, wherein said engineered T-cell has at least one inactivated allele, wherein said at least one inactivated allele is selected from the group consisting of β2m, PD1, CTLA4, dCK, CD52, GR, and a combination thereof.

8. The genetically engineered immune cell of claim 1, wherein said engineered cell expresses no further CAR than said CAR22 and CAR20.

9. A pharmaceutical composition comprising the genetically engineered immune cell of claim 1, and a pharmaceutically acceptable excipient.

10. An isolated polynucleotide comprising, from 5' to 3':

a) a promoter that controls the expression of a CAR20, followed by a nucleic acid encoding said CAR20; and b) a nucleic acid encoding a CAR22, wherein said nucleic acids of a) and b) are on a single nucleic acid molecule, and wherein a nucleic acid sequence encoding a self-cleaving peptide is located between said nucleic acids of a) and b), and wherein said single nucleic acid molecule comprises the sequence of SEQ ID NO: 32.

11. The polynucleotide of claim 10, wherein said polynucleotide does not comprise a nucleic acid encoding a further CAR than said CAR22 and CAR20.

12. A vector comprising the isolated polynucleotide of claim 10.

13. A method of preparing the genetically engineered immune cell of claim 1, said method comprising introducing into an immune cell the polynucleotide of claim 10, or the vector of claim 12.

14. A method of treating a patient having a cancer associated with CD20 expression, CD22 expression, or CD20 expression and CD22 expression, said method comprising administering to said patient an effective amount of the genetically engineered immune cell of claim 1.

15. The method of claim 14, wherein said cancer is selected from the group consisting of lymphoma, Hodgkin lymphoma (HL), non-Hodgkin lymphoma (NHL), leukemia, multiple myeloma (MM), B-chronic lymphocytic leukemia (B-CLL), hairy cell leukemia (HCL), acute lymphocytic leukemia (ALL), acute lymphocytic cancer, and acute myeloid leukemia (AML).

16. The method of claim 14, wherein said cancer is non-Hodgkin lymphoma or acute lymphocytic leukemia.

17. The genetically engineered immune cell of claim 1, wherein each of said CAR22 and said CAR20 do not comprise a leader sequence when said CAR22 and said CAR20 are at the cell surface.

18. A genetically engineered immune cell expressing a Chimeric Antigen Receptor (CAR) that specifically binds to CD20 (CAR20) and a CAR that specifically binds to CD22 (CAR22) at its cell surface, wherein:

(a) said CAR20 comprises the amino acid sequence of SEQ ID NO: 18, optionally without the leader sequence of SEQ ID NO: 1;

(b) said CAR22 comprises the amino acid sequence of SEQ ID NO: 14, optionally without the leader sequence of SEQ ID NO: 1;

(c) said genetically engineered immune cell comprises at least one allele encoding TCR alpha, TCR beta, or CD3 that has been inactivated;

(d) said genetically engineered immune cell has at least one inactivated CD52 allele; and (e) said CAR20 and said CAR22 are encoded by an exogenous nucleic acid incorporated in the genome of said genetically engineered immune cell, wherein said exogenous nucleic acid comprises SEQ ID NO: 32.

19. The genetically engineered immune cell of claim 18, wherein said genetically engineered immune cell comprises at least one allele encoding TCR alpha that was inactivated by mutation.

20. A population of T-cells comprising the genetically engineered immune cell of claim 18.

21. A pharmaceutical composition comprising a pharmaceutically acceptable excipient and the genetically engineered immune cell of claim 18.

22. A pharmaceutical composition comprising a pharmaceutically acceptable excipient and the population of T-cells of claim 20.

23. An ex vivo method of preparing the genetically engineered immune cell of claim 18, wherein said method comprises introducing, into a T cell, the polynucleotide of claim 10 or the vector of claim 12, wherein said T cell comprises at least one inactivated allele encoding TCR alpha, TCR beta, or CD3, and wherein said T cell comprises at least one inactivated CD52 allele.

24. A method of treating a patient having a cancer associated with CD20 expression, CD22 expression, or a combination of CD20 expression and CD22 expression, wherein said method comprises administering to said patient an effective amount of the genetically engineered immune cell of claim 18.

25. The method of claim 24, wherein said cancer is selected from the group consisting of lymphoma, Hodgkin lymphoma (HL), non-Hodgkin lymphoma (NHL), leukemia, multiple myeloma (MM), B-chronic lymphocytic leukemia (B-CLL), hairy cell leukemia (HCL), acute lymphocytic leukemia (ALL), acute lymphocytic cancer, and acute myeloid leukemia (AML).

26. The method of claim 24, wherein said cancer is NHL.

* * * * *